United States Patent
Cheng et al.

(10) Patent No.: US 9,655,914 B2
(45) Date of Patent: May 23, 2017

(54) COMPOSITIONS INCLUDING TRICIRIBINE AND EPIDERMAL GROWTH FACTOR RECEPTOR INHIBITOR COMPOUNDS OR SALTS THEREOF AND METHODS OF USE THEREOF

(71) Applicant: University of South Florida, Tampa, FL (US)

(72) Inventors: Jin Q. Cheng, Tampa, FL (US); Said M. Sebti, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 14/998,352

(22) Filed: Dec. 28, 2015

(65) Prior Publication Data

US 2016/0206644 A1 Jul. 21, 2016

Related U.S. Application Data

(63) Continuation of application No. 14/092,323, filed on Nov. 27, 2013, now Pat. No. 9,265,783, which is a continuation of application No. 13/453,789, filed on Apr. 23, 2012, now Pat. No. 8,673,867, which is a continuation of application No. 12/118,861, filed on May 12, 2008, now abandoned, which is a continuation-in-part of application No. 11/096,082, filed on Mar. 29, 2005, now Pat. No. 8,435,959.

(60) Provisional application No. 60/557,599, filed on Mar. 29, 4.

(51) Int. Cl.
| | | |
|---|---|---|
| A61K 31/70 | (2006.01) |
| A61K 31/7052 | (2006.01) |
| A61K 31/7064 | (2006.01) |
| A61K 31/7076 | (2006.01) |
| A61K 45/06 | (2006.01) |
| A61K 9/00 | (2006.01) |
| A61K 31/517 | (2006.01) |
| A61K 31/5377 | (2006.01) |

(52) U.S. Cl.
CPC ........ A61K 31/7064 (2013.01); A61K 9/0019 (2013.01); A61K 9/0053 (2013.01); A61K 31/517 (2013.01); A61K 31/5377 (2013.01); A61K 31/7076 (2013.01); A61K 45/06 (2013.01)

(58) Field of Classification Search
CPC ............ A61K 31/7064; A61K 31/7076; A61K 31/337; C07H 17/02
USPC ...................... 514/43, 42, 23; 536/27.1, 22.1
See application file for complete search history.

(56) References Cited

U.S. PATENT DOCUMENTS

| | | |
|---|---|---|
| 4,123,524 A | 10/1978 | Townsend |
| 5,334,374 A | 8/1994 | Hartley et al. |
| 5,541,287 A | 7/1996 | Yau et al. |
| 5,681,970 A | 10/1997 | Didier et al. |
| 5,759,837 A | 6/1998 | Kuhajda et al. |
| 5,859,065 A | 1/1999 | Brandes |
| 5,976,535 A | 11/1999 | Fritzberg et al. |
| 6,013,646 A | 1/2000 | Roder et al. |
| 6,017,514 A | 1/2000 | Epstein et al. |
| 6,020,179 A | 2/2000 | Goli |
| 6,067,491 A | 5/2000 | Takahashi |
| 6,080,877 A | 6/2000 | Swindell et al. |
| 6,143,765 A | 11/2000 | Tang et al. |
| 6,177,460 B1 | 1/2001 | Camden |
| 6,197,306 B1 | 3/2001 | Murali |
| 6,207,145 B1 | 3/2001 | Tovey |
| 6,258,582 B1 | 7/2001 | Acton |
| 6,388,076 B1 | 5/2002 | Mjalli et al. |
| 6,410,586 B1 | 6/2002 | Moller et al. |
| 6,541,468 B1 | 4/2003 | Roder et al. |
| 6,569,853 B1 | 5/2003 | Borisy et al. |
| 6,693,125 B2 | 2/2004 | Borisy et al. |
| 2002/0035090 A1 | 3/2002 | Zeldis et al. |
| 2002/0048813 A1 | 4/2002 | Gertler et al. |
| 2002/0128228 A1 | 9/2002 | Hwu |
| 2002/0169140 A1 | 11/2002 | Prendergast |
| 2002/0197639 A1 | 12/2002 | Shia et al. |
| 2003/0008886 A1 | 1/2003 | Goehring et al. |
| 2003/0017964 A1 | 1/2003 | Zerangue et al. |
| 2003/0018041 A1 | 1/2003 | Goehring et al. |
| 2003/0027834 A1 | 2/2003 | Goehring et al. |
| 2003/0036199 A1 | 2/2003 | Bamdad et al. |
| 2003/0119747 A1 | 6/2003 | Lanser |
| 2003/0158114 A1 | 8/2003 | Wallner et al. |
| 2003/0187052 A1 | 10/2003 | Muller et al. |
| 2003/0204090 A1 | 10/2003 | Ono et al. |

(Continued)

FOREIGN PATENT DOCUMENTS

| | | |
|---|---|---|
| EP | 0359347 A2 | 8/1989 |
| JP | 2007-530705 | 11/2007 |

(Continued)

OTHER PUBLICATIONS

Konecny, et al.: "Activity of the Dual Kinase Inhibitor Lapitinab (GW572016) Against HER-2 overexpressing and Trastuzumab-Treated Breast Cancer", Cancer Research, 66(3), pp. 1630-1639 (2006).

(Continued)

Primary Examiner — Shaojia Anna Jiang
Assistant Examiner — Michael C Henry
(74) Attorney, Agent, or Firm — Seyfarth Shaw LLP

(57) ABSTRACT

This application relates to combination therapies including triciribine compounds and epidermal growth factor receptor inhibitor compounds, particularly erlotinib-like compounds and compositions with reduced toxicity for the treatment and prevention of tumors, cancer, and other disorders associated with abnormal cell proliferation.

19 Claims, 28 Drawing Sheets

(56) References Cited

U.S. PATENT DOCUMENTS

Figure 3A:
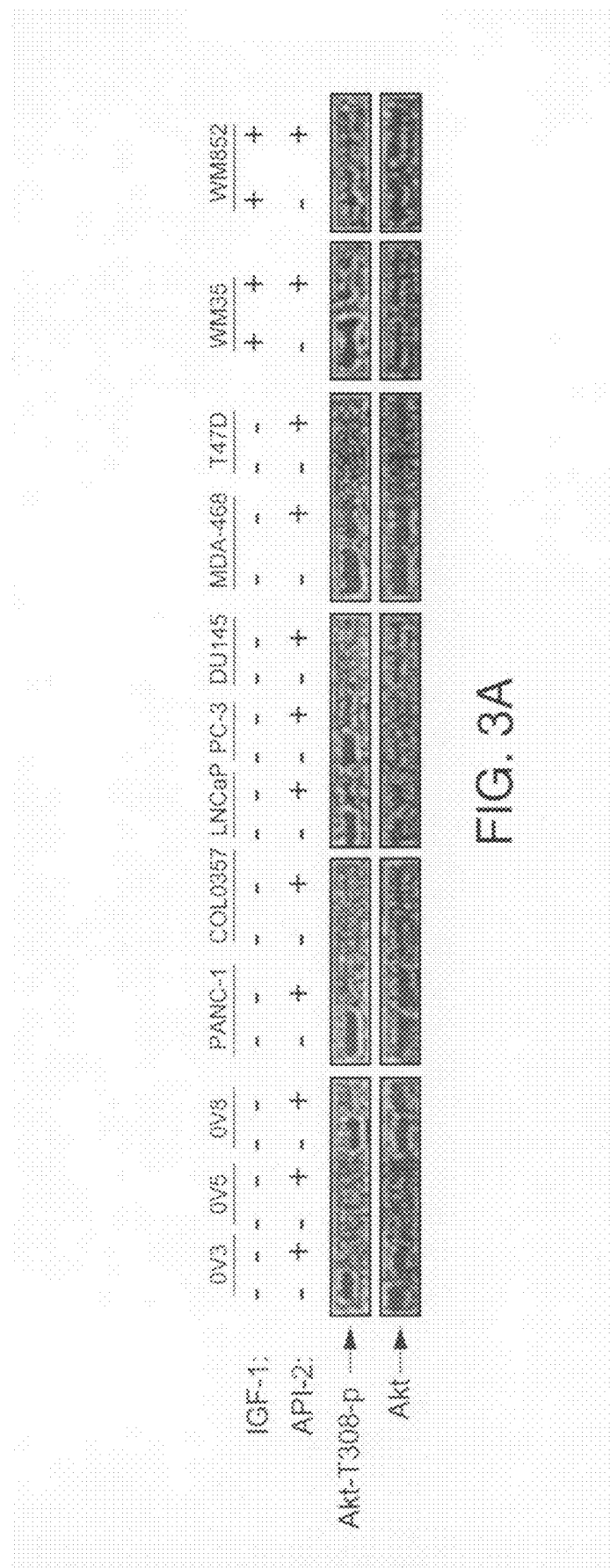

| | | |
|---|---|---|
| 2003/0216309 A1 | 11/2003 | Krag et al. |
| 2004/0001835 A1 | 1/2004 | Woessner et al. |
| 2004/0028685 A1 | 2/2004 | Kinch et al. |
| 2004/0029832 A1 | 2/2004 | Zeldis |
| 2004/0034084 A1 | 2/2004 | Zeldis |
| 2004/0058896 A1 | 3/2004 | Dietrich et al. |
| 2004/0067953 A1 | 4/2004 | Stein et al. |
| 2004/0072755 A1 | 4/2004 | Stennicke et al. |
| 2004/0072824 A1 | 4/2004 | Telerman et al. |
| 2004/0077601 A1 | 4/2004 | Adams et al. |
| 2004/0087531 A1 | 5/2004 | Telerman et al. |
| 2004/0087546 A1 | 5/2004 | Zeldis |
| 2004/0087641 A1 | 5/2004 | Goehring et al. |
| 2004/0091471 A1 | 5/2004 | Myette et al. |
| 2004/0091486 A1 | 5/2004 | Kinch et al. |
| 2004/0092572 A1 | 5/2004 | Renaud et al. |
| 2004/0102467 A1 | 5/2004 | Jaquith et al. |
| 2004/0126434 A1 | 7/2004 | Kumana et al. |
| 2004/0138263 A1 | 7/2004 | D'Angio et al. |
| 2004/0146514 A1 | 7/2004 | Smith et al. |
| 2004/0156828 A1 | 8/2004 | Xu et al. |
| 2004/0167199 A1 | 8/2004 | Muller et al. |
| 2004/0180949 A1 | 9/2004 | Shashoua et al. |
| 2005/0092583 A1 | 5/2005 | Meins et al. |

FOREIGN PATENT DOCUMENTS

| | | |
|---|---|---|
| WO | WO 92/00988 | 1/1992 |
| WO | WO 92/17185 | 10/1992 |
| WO | WO 00/18439 | 4/2000 |
| WO | WO 00/21506 | 4/2000 |
| WO | WO 01/35935 | 5/2001 |
| WO | WO 02/053138 A2 | 7/2002 |
| WO | WO 02/069949 A2 | 9/2002 |
| WO | WO 03/075917 A1 | 9/2003 |
| WO | WO 2004/043378 A2 | 5/2004 |
| WO | WO 2004/064826 A1 | 8/2004 |
| WO | WO 2004/065572 A2 | 8/2004 |
| WO | WO 2005/094322 | 10/2005 |
| WO | WO 2005/094322 A | 10/2005 |
| WO | WO 2005/110477 A | 11/2005 |
| WO | WO 2006/125539 A | 11/2006 |

OTHER PUBLICATIONS

Lan, et al.: "Mechanisms of Trastuzumab Resistance and Their Clinical Implications", Am. N.Y. Acad. Sci. 1059, pp. 70-75 (2005).
Li, Q.: "Recent Progress in the Discovery of Akt Inhibitors as Anticancer Agents", Expert Opinion on Therapeutic Patents (GB), 17(9)m oo 1077-1130 (2007).
Lu, et al.: "Preclinical Testing of Clinically Applicable Strategies for Overcoming Trastuzumab Resistance caused by PTEN Deficiency", Clinical Cancer Research: An Official Journal of the American Association for Cancer Research, 13(9), pp. 5883-5888 (2007).
Normanno, et al.: "Is the Gefitinib Plus Trastuzumab Combination Feasible in Breast Cancer Patients?", Annals of Oncology: Official Journal fo the European Society for Medical Oncoloy/ESMO, 16(10), pp. 1709 (2005).
Schram et al., The Synthesis of 6-Amino-4-Methyl-8-(β-D-Ribofuranosyl) (4-H. 8-H) Pyrrolo-[4,3,2-de]Pyrimido[4,5-c]Pyridazine, A New Tricyclic Nucleoside (1), Tetrahedron Letters No. 49, 1971, pp. 47-4760.
Plagemann, Transport, Phosphorylation, and Toxicity of a Tricyclic Nucleoside in Cultured Novikoff Rat Hepatoma Cells and Other Cell Lines and Release of Its Monophosphate by the Cells; J. National Cancer Institute, vol. 57 No. 6, Dec. 1976, pp. 1283-1295.
Bennett, Jr. et al., Biochemical Properties of the Nucleoside of 3-Amino-1.5-Dihydro-5-Methyl-1, 4, 5, 6, 8-Pentaazaacenaphthylene (NSC-154020), Biochemical Pharmacology, vol. 27, 1978, pp. 233-241.
Roti Roti et al., Studies of the Mechanism of Cytotoxicity of the Tricyclic Nucleoside NSC#154020 in 11210 Cells, AACR Abstracts, 1978, p. 40.
Schweinsberg, et al., Uptake and Metabolism of the Antitumor Tricyclic Nucleoside (TCN) by Human Red Blood Cells, AACR Abstracts, 1979, p. 168.
Schweinsberg, et al., Effects of the Anti-Tumor Tricyclic Nucleoside, Amino-1-5-Dihydro-5-Methyl-1-6-D-Ribofuranosyl-1, 4, 5, 6, 8-Pentaazaacenaphthylene (TCN, NSC-154020); AACR Abstracts, Mar. 1980. p. 33.
Ti Li Loo, Pharmacology of New Cancer Chemotherapy Agents, 1980, pp. 147-162.
Schweinsberg et al., Identification of the Metabolites of an Antitumor Tricyclic Nucleoside (NSC-154020)*, Biochemical Pharmacology, vol. 30, No. 18, 1981, pp. 2521-2526.
Paul David Schweinsberg, Uptake, Metabolism, and Metabolic Effects of the Antitumor Tricyclic Nucleoside, 3-Amino-1, 5-Dihydro-5-Methyl-I-Beta-D-Ribofuranosyl-1, 4, 5r, 6, 8 Pentaazaacenaphthylene; Dissertions Abstracts International, 1980.
Bodner et al., Induction of Differentiation of Human Promyelocytic Leukemia Cells (HL-60) by Nucleotides and Methotrexate; JNCI vol. 67, No. 5, Nov. 1981, pp. 1025-1030.
Basseches et al., High-Performance Liquid Chromatographic Assay of the Antineoplastic Agent Tricyclic Nucleoside 5'-Phosphate and Its Disposition in Rabbit; Journal of Chromatography 233, 1982, pp. 227-234.
Cobb et al., Activity of Phase I Drugs Homoharringtonine (HHT) and Tricyclic Nucleotide (TCN) Against Surgical Explants of Human Tumors in the 6-Day Subrenal Capsule (SRC) Assay; AACR Abstracts, 1982, p. 222.
Dickie et al., Preclinical Toxicity Study of Pentaazaacenaphthylene -5' Phosphate Ester (NSC-280594) in CD2F1 Mice and Beagle Dogs; AACR Abstracts, 1983, p. 296.
Mittelman et al., Phase I Study of Tricyclic Nucleoside Phosphate; Cancer Treatment Reports, vol. 67, No. 2, Feb. 1983, pp. 159-162.
Feun et al., Phase I Trial of 1, 4, 5, 6, 8-Pentaazaacenaphthylene, 3-Amino, 1, 5-Dihydro-5-Methyl-1-β-D-Ribofuranosyl-5'-Phosphate Ester (TCN-P), NSC 280594) on a 5-day Continuous Infusion Schedule; AACR Abstracts, 1983.
Spremulli, et al., Hemodynamic Effects of Potentially Useful Antineoplastic Agents; JNCI, vol. 70, No. 3, Mar. 1983, pp. 499-504.
Plagemann et al., Adenosine and Tubercidin Binding and Transport in Chinese Hamster Ovary and Novikoff Rat Hepatoma Cells; Journal of Cellular Physiology 116, 1983, pp. 247-255.
John M. Venditti, The National Cancer Institute Antitumor Drug Discovery Program, Current and Future Perspectives: A Commentary, Cancer Treatment Reports vol. 67. No. 9, Sep. 1983, pp. 767-772.
Plagemann et al, Adenosine Metabolism in Wild-Type and Enzyme-Deficient Variants of Chinese Hamster Ovary and Novikoff Rat Hepatoma Cells, Journal of Cellular Physiology 116, pp. 236-246, 19830.
Cobb et al., Activity of Two Phase I Drugs, Homoharringtonine and Tricyclic Nucleotide, Against Surgical Explants of human Tumors in the 6-Day Subrenal Capsule Assay; Cancer Treatments Reports vol. 67 No. 2, Feb. 1983, pp. 173-178.
Roshon et al., In Vitro Activity of Tricyclic Nucleotide 5'—Phosphate (TCN-P) Assayed by the Human Tumor Cloning Assay (HTCA); AACR Abstracts, 1983, p. 317.
Savaraj et al., Comparative Pharmacology of 3-Amino-1, 5-Dihydro-5-Methyl-1-β-D-Ribofuranosyl-1, 4, 5, 6, 8-Pentaazaacenaphthylene, (TCN, NSC-154020) and its 5'-Monophosphate (TCN-P, NSC-280594) in Dogs; AACR Abstracts, 1983, p. 290.
Johnson et al., Correlation of Cellular Tritiated Thymidine Incorporation with Soft Agar Clonogenicity in Chemosensitivity Testing of Human Neuroblastoma Cells; Cancer Treatment Reports vol. 67, No. 2, Feb. 1983, pp. 163-168.
Bennett et al., Phosphorylation of "tricyclic nuceloside" by Adenosine Kinases from L1210 Cells and HEp-2 cells; Biochemical Pharmacology, vol. 32, No. 17, 1983, pp. 2601-2602.
Alley et al., Activation and Inactivation of Cancer Chemotherapeutic Agents by Rat Hepatocytes Cocultured with Human Tumor Cell Lines; Cancer Research 44, Feb. 1984, pp. 549-556.

(56) References Cited

OTHER PUBLICATIONS

Gupta et al., Genetic and Biochemical Studies on Mutants of CHO Cells Resistant to 7-Deazapurine Nucleosides: Differences in the Mechanisms of Action of Toyocamycin and Tubercidin; Biochemical and Biophysical Research Communications, vol. 120, No. 1, Apr. 1984, pp. 88-95.
Feun et al., Phase I Study of Tricyclic Nucleoside Phosphate Using a Five-Day Continuous Infusion Schedule; Cancer Research vol. 44, Aug. 1984, pp. 3608-3612.
Basseches et al., Metabolism and Disposition of 3-Amino-1, 5-dihydro-5-methyl-1-β-D-ribofuranosyl-1,4,5,6,8-pentaazaacenaphthylene in the Rat; Cancer Research 44, Sep. 1984, pp. 3672-3678.
Wotring et al., Effects of the Tricyclic Nucleotside 6-Amino-4-methyl-8-(β-D-ribofuranosyl)-pyrrolo[4,3,2,-de]pyrimido[4,5,-c]pyridazine on the Viability and Cell Cycle Distribution of L1210 Cells in Vitro; Cancer Research vol. 45, Dec. 1985; pp. 6355-6361.
Schilcher et al., Reversed-Phase High-Performance Liquid Chromatographic Determination of Tricyclic Nucleoside and Tricyclic Nucleoside 5'-Phosphate in Biological Specimens; Journal of Chromatography, vol. 337, 1985, pp. 55-62.
Valeriote et al., MOPC-315 Murine Plasmacytoma as a Model Anticancer Screen for Human Multiple Myeloma; JNCI, vol. 76, No. 1, Jan. 1986, pp. 61-65.
Wotring et al., Mechanism of Activation of Tricirbine Phosphate (TCN-P) as a Prodrug Form of $TCN^{1,23}$, Cancer Treatment Reports vol. 70, No. 4, Apr. 1986, pp. 491-497.
Schilcher et al., Phase 1 Evaluation and Clinical Pharmacology of Tricyclic Nucleoside 5'-Phosphate Using a Weekly Intravenous Regimen; Cancer Research 46, Jun. 1986, pp. 3147-3151.
Grieshaber et al., Relation of Preclinical Toxicology to Findings in Early Clinical Trials; Cancer Treatment Reports Vo. 70, No. 1, Jan. 1986, pp. 65-72.
Collins et al., Potential Roles for Preclinical Pharmacology in Phase I Clinical Trials; Cancer Treatment Reports vol. 70, No. 1, Jan. 1986, pp. 73-80.
Moore et al., Mechanisms of Inhibition of Protein and Purine Biosynthesis by Tricyclic Nucleoside Phosphate (TCN-P), Triciribine Phosphate, NSC 280594); Proceedings of AACR vol. 27, Mar. 1986; p. 303.
Wotring et al., Studies on the Biochemical Mechanism of DNA Synthesis Inhibition by Triciribine (TCN); Proceedings of AACR vol. 27, Mar. 1986, p. 295.
Powis et al., Disposition of Tricyclic Nucleoside-5'-monophosphate in Blood and plasma of Patients During Phase I and II Clinical $Trials^{1,2}$; Cancer Treatment Reports, vol. 70, No. 3, Mar. 1986, pp. 359-362.
Estey et al., Therapeutic Response in Phase I Trials of Antineoplastic $Agents^{1}$; Cancer Treatment Reports vol. 70, No. 9, Sep. 1986, pp. 1105-1115.
Behrens et al., Activity of tricyclic nucleoside 5'-phosphate in model systems of human ovarian cancer, Investigational New Drugs 4, 1986, pp. 295-304.
Townsend et al., The synthesis and biological activity of certain pentaazaacenaphthylene, hexaazaacenaphthylenes and their corresponding nucleosides; Symposium Series No. 17, 1986; pp. 41-44.
Borysko et al., Dual Mechanisms of Inhibition of DNA Synthesis by Triciribine; Experimental Therapeutics, 1987.
Marsoni et al., Clinical Drug Development: An Analysis of Phase II Trials, 1970-$1985_1$; Cancer Treatment Reports, vol. 71, No. 1, Jan. 1987; pp. 71-80.
Wotring et al., Triciribine (TCN), A Novel Tricyclic adenosine Analog with Anitcancer Activity; Nucleosides & Nucleotides, 6(1&2), 1987, pp. 95-109.
O'Connell et al., Phase II Clinical Trial of Tricyclic Nucleoside Phosphate for Advanced Colorectal Cancer; Cancer Treatment Reports, vol. 71, No. 3, Mar. 1987, pp. 333-334.
Zee-Cheng et al., Screening and Evaluation of Anticancer Agents; Meth. and Find Exptl. Clinical Pharmacology; 1988, pp. 67-101.
Moore et al., Inhibition of CCRF-CEM Human Leukemic Lymphoblasts by Triciribine (Tricyclic Nucleoside, TCN, NSC-154020); Biochemical Pharmacology, vol. 38, No. 22, 1989; pp. 4037-4044.
Wotring et al., Dual Mechanisms of Inhibition of DNA Synthesis by Triciribine, 1989, p. 179.
Decoster et al., Responses and toxic deaths in Phase I clinical trials; Annals of Oncology 1: 1990, pp. 175-181.
Wotring et al., Dual Mechanisms of Inhibition of DNA Synthesis by Triciribine; Cancer Research 50, Aug. 15, 1990, pp. 4891-4899.
Waud et al., Antitumor Drug Cross-Resistance in Vivo in a Cisplatin-Resistant Murine P388 Leukemia; Cancer Chemotherapyand Pharmacology 27, 1991, pp. 456-463.
Lyss et al., Triciribine Phosphate (TCN-P) in Advanced Non-Small Cell Lung Cancer (NSCLC): Interim Analysis of Toxicity; Proceedings of ASCO vol. 10, Mar. 1991, p. 120.
Feun et al., A Phase II Trial of Tricyclic Nucleoside Phosphate in Patients with Advance Squamous Cell Carcinoma of the Cervix; Am J Clin Oncol (CCT) 16(6), 1993; pp. 506-508.
Kucera et al., Activity of Triciribine and Triciribine-5'-Monophosphate Against Human Immunodeficiency Virus Types 1 and 2; Aids Research and Human Retroviruses, vol. 9, No. 4, 1993, pp. 307-314.
Hoffman et al., Phase I-II study: Triciribine (Tricyclic Nucleoside Phosphate) for Metastatic Breast Cancer; Cancer Chemotherapy and Pharmacology 37, 1996, pp. 254-258.
Bellacosa et al., Molecular Alterations of the *AKT2* Oncogene in Ovarian and Breast Carcinomas; Int. J. Cancer (Pred. Oncol.) 64, 1995, pp. 280-285.
Porcari et al., The Design, Synthesis, and Evaluation of a Series of Acyclic Triciribine Analogs for Their Antiviral and Antineoplastic Activity.
Ptak et al., Phosphorylation of Triciribine Is Necessary for Activity against HIV Type 1; Aids Research and Human Retroviruses vol. 14, No. 15, 1998, pp. 1315-1322.
Porcari et al., Acyclic Sugar Analogs of Triciribine: Lack of Antiviral and Antiproliferative Activity Correlate with Low Intracellular Phosphorylation; Nucleoside and Nucleotides, 18(11&12), 1999, pp. 2475-2497.
Porcari et al., Deoxy sugar Analogues of Triciribine: Correlation of Antiviral and Antiproliferative Activity with Intracelluar Phosphorylation; J. Med. Chem. 2000, 43, pp. 2438-2448.
Porcari et al., 6-*N*-Acyltriciribine Analogues: Structure-Activity Relationship between Acyl Carbon Chain Length and Activity against HIV-1; J. Med. Chem., 43, 2000, pp. 2457-2463.
Wotring et al., Metabolism of Triciribine in L1210 cells; 1989.
Sun ct al., AKT1/PKBα Kinase Is Frequently Elevated in Human Cancers and Its Constitutive Activation Is Required for Oncogenic Transformation in NIH13T3 Cells; American Journal of Pathology, vol. 159, Aug. 2001; pp. 431-437.
Gudmundsson et al., Synthesis of Carbocyclic Analogs of 2', 3'-Dideoxysangivamycin, 2',3'-Dideoxytoyocamycin, and 2',3'-Dideoxytriciribine; Nucleosides, Nucleotides & Nucleic Acids, 20(10&11), 2001, pp. 1823-1830.
Shedden et al., A Rational Approach to Personalized Anticancer Therapy: Chemoinformatic Analysis reveals Mechanistic Gene-Drug Associations; Pharmaceutical Research vol. 20, No. 6, Jun. 2006, pp. 843-847.
Shedden et al., Expulsion of Small Molecules 1 vesicles Shed by Cancer Cells: Association with Gene Expression and Chemosensitivity Profiles; Cancer Research 63, Aug. 1, 2003; pp. 4331-4337.
Porcari et al., Synthesis and Antiviral Activity of 2-Substituted Analogs of Triciribine; Nucleosides, Nucleotides & Nucleic Acids, vol. 22, No. 12, 2003, pp. 2171-2193.
Porcari et al., An Improved Total Synthesis of Triciribine: A Tricyclic Nucleoside with Antineoplastic and Antiviral Properties; Nucleosides, Nucleotides & Nucleic Acids, vol. 23, Nos. 1 & 2, pp. 31-39.
Ren et al., Anticancer Agents: Tumor Cell Growth Inhibitory Activity and Binary QSAR Analysis; Current Pharmaceutical Design, 2004, pp. 1399-1415.

(56) References Cited

OTHER PUBLICATIONS

Smith et al., Synthesis of new 2'-β-C-methyl related triciribine analogues as anti-HCV agents; Bioorganic & Medicinal Chemistry Letters 14, 2004, pp. 3517-3520.
Yang et al., Akt/Protein Kinase B Signaling Inhibitor-2, a Selective Small Molecule Inhibitor of Akt Signaling with Antitumor Activity in Cancer Cells Overexpressing Akt; Cancer Research 64, Jul. 1 2004, pp. 4394-4399.
Westwell et al., Selective Small-Molecule Inhibitor of Akt-Signalling; Drug Discover Today, vol. 9, No. 19, Oct. 2004, p. 855.
Schilcher, at al., Journal of Chromatography, v. 337(1), pp. 55-562, Abstract only, 1985.
Gura, Science, 278 (45340), pp. 1041-1042, 1997.
Database STN Abstract: Accession No. 1985-124969 Caplus, Document No. 102:124969, "Reversed-phase high-performance liquid chromatographic determination of tricyclic nucleoside and 1 tricyclic nucleoside 5'-phosphate in biological specimens". Schilcher et al., 1 Chromatography, 1985, 337(1), 55-62.
Database STN Abstract: Accession No. 1984:603807 Caplus, Document No. 101-203807, "Metabolism and disposition of 3-amino-1,5-dihydro-5-methyl-1-beta-D-ribofuranosyl-1,4,5,6,8-pentaazaacenaphthylene in the rat". Basseches et al., Cancer Research 1984, 44(9), 3672-8.
Adachi, M. et al. "Mammaliam SH2-containing protein tyrosis phosphatases" Cell, 1996, 85, pp. 15.
Alexander, J. et al. "Endogenous IL-4 is necessary for effective drug therapy against visceral leishmaniasis" Eur. J. Immunol., 2000, 30, pp. 2935-2943.
Almeida, R. et al. "Randomized, double-blind study of stibogluconate plus human granulocyte macrophage colony-stimulating factor versus stibogluconate alone in the treatment of cutaneous Leishmaniasis" J. Infect. Dis., 1999, 180(5), pp. 1735-1737.
Aoki, N. et al. "A cytosolic protein-tyrosine phosphatase PTP1B specifically dephosphorylates and deactivates prolactin-activated STAT5a and STAT5b"J. Biol. Chem., 2000, 275, pp. 39718-39726.
Ayub, M. et al. "Inhibition of testicular 17 alpha-hydrosylase and 17,20-lyase but not 3 beta-hydroxysteroid dehydrogenase-isomerase or 17 beta-hydroxysteroid oxidoreductase by ketoconazole and other imidazole drugs" J. Steroid Biochem., 1987, 28, pp. 521-523.
Badaro, R. et al. "Granulocyte-macrophage colony-stimulating factor in combination with pentavalent antimony for the treatment of visceral Leishmaniasis" Eur J Clin Microbiol Infect Dis., 1994, 13 Suppl 2, pp. S23-S28.
Baer, H. P. et al. "Pentamidine does not interfere with nitrite formation in activated raw 264.7 macrophages but inhibits constitutive brain nitric oxide synthase" Life Sciences, 1995, 57, pp. 1973-1980.
Bailly, C. et al. "Sequence-selective binding to DNA of bis(amidinoplienoxy)alkanes related to propamidine and pentamidine" Biochem. J., 1997, 323, pp. 23-31.
Bennett, J. M. et al. "Criteria for the diagnosis of acute leukemia of megakaryocyte lineage (M7). A report of the French-American-British Cooperative Group" Ann. Intern. Med., 1985, 103, pp. 460-462.
Bennett, J. M. et al. "Proposal for the recognition of minimally differentiated acute myeloid leukaemia (AML-MO)" Br. J. Haematol., 1991, 78, pp. 329.
Bergamaschi, G. et al. "Tumor necrosis factor alpha down-regulates c-myc mRNA expression and induces in vitro monocytic differentiation in fresh blast cells from patients with acute myeloblastic leukemia" Leukemia, 1990, 4, pp. 426-430.
Berman J.D. and Wyler, DJ. "An in vitro model for investigation of chemotherapeutic agents in leishmaniasis" J. Infect. Dis., 1988, 142, pp. 83-86.
Berman, J. et al. "Gastroincstinal stromal tumor workshop" Hum. Pathol., 2001, 32, pp. 578-582.
Berman, J.D. "Chemotherapy for leishmaniasis: biochemical mechanisms, clinical efficacy, and future strategies" Rev. Infect. Dis., 1988, 10, pp. 560-586.

Berman, J.D. et al. "Leishmania mexicana: chemistry and biochemistry of sodium stibogluconate (Pentostam)" Exp. Parasitol., 1988, 67, pp. 96-103.
Berman, J.D., G. Holz Jr. and D.H. Beach. Effects of ketoconazole on growth and sterol biosynthesis of Leishmania Mexicana promastigotes in culture, Mol Biochem Parasitol, 1984, 12, pp. 1-13.
Berndt, A. et al. Expression of the transmembrane protein tyrosine phosphatase RPTPalpha in human oral squamous cell carcinoma. Histochem. Cell. Biol., 1999, 111, pp. 399-403.
Bittorf, T. et al. "SHP1protein tyrosine phosphatase negatively modulates erythroid differentiation and suppression of apoptosis in J2E erythroleukemic cells" Biol. Chem., 1999, 380, pp. 1201-1209.
Blanchette, J. et al. "Leishmania-induced increases in activation of macrophage SHP-1 tyrosine phosphatase are associated with impaired IFN-gamma-triggered JAK2 activation" Eur. J. Immunol., 1999, 29, pp. 3737-3744.
Bleumer, I. E. et al. "Immunotherapy for renal cell carcinoma" Eur. Urol., 2003, 44, pp. 75.
Bloomfield, C.D. et al. "The revised French-American-British classificatio of acute myeloid leukemia: is new better?"Ann. Intern. Med., 1985, 103, pp. 61.1-616.
Blume Jensen, P. et al. "Oncogenic kinase signaling" Nature, 2001, 411, pp. 355-365.
Bok, R. A. et al. "The treatment of advanced prostate cancer with ketoconazole: safety issues" Drug Saf., 1999, 20, pp. 451-158.
Borden E. C. "Reducing primary melanoma mortality" Curr. Oncol. Rep., 2000, 2, pp. 289-291.
Borden, E. C., et al. "Second-generation interferons for cancer: clinical targets" Semin. Cancer Biol., 2000, 10, pp. 125-144.
Bradbury, J., "Metastasis in colorectal cancer associated with phosphatase expression" Lancet, 2001, 358, pp. 1245.
Breitman, T.R. et al. "Induction of differentiation of the human promyelocytic leukemia cell line (HL-60) by retinoic acid" Proc. Natl. Acad. Sci. USA, 1980, 77, pp. 2936-2940.
Bronner, U. et al. "Pentaminidine concentrations in plasma, whole blood and cerebrospinal fluid during treatment of *Trypanosoma gambiense* infection in Cote d'lvoire" Transactions of the Royal Society of Tropical Medicine and Hygiene, 1991, 85: 608-611.
Brotvu-Shimer, S. et al. "Effect of protein tyrosine phosphatase 1B expression on transformation by the human reu oncogene" Cancer Research, 1992, 52, pp. 478-482.
Buchdunger, E., et al. "Inhibition of the Abl Protein-Tyrosine Kinase in Vitro an in Vivo by a 2-phenylaminopyrimidine derivative" Cancer Res., 1996, 56, pp. 100-104.
Buick, R. N. et al. "Comparative properties of live human ovarian adenocarcinoma cell lines" Cancer Res., 1985, 45, pp. 3668-3676.
Burke, T., Jr. et al. "Protein-tyrosine phosphatases: structure, mechanism, and inhibitor discovery" Biopolymers 1998, 47, pp. 225.
Burshtyn D. N. et al. "Recruitment of tyrosine phosphatase HCP by the killer cell inhibitor receptor" Immunity, 1996, 4, pp. 77-85.
Burshtyn, D. N. et al. "A novel phosphotyrosine motif with a critical amino acid at position-2 for the SH2 domain-mediated activiation of the tyrosine phosphatase SHP-1"J. Biol. Chem., 1997, 272, pp. 13066-13072.
Caillcau, R. et al. "Breast tumor cell lines from pleund effusions" J. Natl. Cancer Inst., 1974, 53, pp. 661-674.
Carini, C., Hudspith, B.N. and Brostolf, J. "Effect of prostaglandins and cyclic nucleotides on growth and immunoglobulin secretion of two IgE myeloma cell lines" Br J Cancer, 1981, 43, pp. 257-260.
Carter, David A. "Expression of a novel rat protein tyrosine phosphatase gene" Bichimica et Biophysica Acta, 1998, 1442, pp. 405-408.
Carter, J. D., B.G. Neel and U. Lorenz. "The tyrosine phosphatase SHP-1 influences thymocyte selection by setting TCR signaling thresholds" Int. Immunol., 1999, 11: 1999-2014.
Castrucci, M. R et al. "Attenuation of influenza A virus by insertion of a foreign epitope into the neuraminidase" J. Virol., 1992, 66, pp. 4647-4653.
Cates, C.A. et al., "Prenylation of oncogenic human PTPcaax protein tyrosine phosphatases" Cancer Lett., 1996, 110, pp. 49-55.

(56) References Cited

OTHER PUBLICATIONS

Chakravortty, D., Kato, Y., Sugiyama, T., Koicle, N., Mu, M. M., Yoshida, T. and Yokochi, T. "The inhibitory action of sodium arsenite on lipopolysaccharide-induced nitric oxide production in RAW 267.4 macrophage cells: a role of Raf-1 in lipopolysacclaride signaling" J. Immunol., 2001, 166, pp. 2011-2017.

Chawla-Sarkar, M., Leaman, D.W.,Jacobs, B.S., Tuthill, R.J., Charrerjee-Kishore, M., Stark, G.R., Borden, E.C., "Resistance to interferons in melanoma cells does not correlate with the expression or activation of signal transducer activator of transcription 1 (stat 1)" J. Interferon Cytokine Res., 2002, 22, pp. 603-613.

Chen, G.Q. et al. "In Vitro Studies on Cellular and Molecular Mechanisms of Arsenic Trioxide (As2O3) in the Treatment of Acute Promyelocytic Leukemia: As2O3 induces NB4 Cell Apoptosis with Downregulation of BCl-2 Expression and Modulation of PML-RAR alpa/PML proteins" Blood, 1996, 88, pp. 1052-1061.

Chen, H., Chang, S., Trub, T. and Neel, B.G. "Regulation of colony-stimulating factor 1 receptor signaling by the SH2 domain-containing tyrosine phosphatase SHPTP1" Mol. Cell. Biol., 1996, 16, pp. 3685-3697.

Chen, Y-T., Holcomb, C., Moore, H-P. H. "Expression and localization of two low molecular weight GTP-binding proteins, Rab8 and Rab10, by epitope tag" Proc. Nat. Acad. Sci USA, 1993, 90, pp. 6508-6512.

Chiarugi, P. et al. "Insight into the role of low molecular weight phosphotyrosine phosphatase (LMW-PTP) on platelet-derived growth factor receptor (PDGF-r) signaling" J. Biol. Chem. 2002, 277 (40), pp. 37331-37338.

Chou, T.C. and Talalay, P. "Quantitative analysis of dose-effect relationships: the combined effects of multiple drugs or enzyme inhibitors" Adv. Enzyme Regul., 1984, 22, pp. 27-55.

Church, D., Zhang, Y., Rago, R. and Wilding, G. "Efficacy of suramin against human prostate carcinoma DU145 xenografts in nude mice" Cancer Chemother Pharmacol, 1999, 43, pp. 198-204.

Clore, C. M. and A. M. Gronenboni. "Structures of larger proteins, protein-ligand and protein-DNA complexes by multidimensional heteronuclear NMR" Protein Science, 1991, 3, pp. 374-390.

Collins, S.J., Ruscetti, F.W., Gallagher, R.E. and Gallo, R.C. "Normal functional characteristics of cultured human promyelocytic leukemia cells (HL-60) after induction of differentiaition by dimethylsulfoxide" J. Exp Med, 1979, 149, pp. 969-974.

Cyster, J. G. and Goodnow, C. C. "Protein tyrosine phosphatase IC negatively regulates antigen receptor signaling in B lymphocytes and determines thresholds for negative selection" Immunity, 1995, 2, pp. 13-24.

Damen, J.E. Cutler, R.L., Jiao, H., Yi, T. and Krystal, G. "Phosphorylation of tyrosine 503 in the crythropoietin receptor (EpR) is essential for binding the P85 subunit of phosphatidylinositol (PI) 3-kinase and for EpR-associated PI 3-kinase activity" J. Biol. Chem., 1995, 270, pp. 23402-23408.

Darnell, Jr. "Studies of IFN-induced transcriptional activation uncover the Jak-Stat pathway" J. Interferon Cytokine Res., 1998, 18, pp. 549-554.

David, M., Chen, H.E., Goetz, S., Lanier, A.C. and Neel, B.G. "Differential regulation of the alpha/beta interferon-stimulated Jak/Stat pathway by the SH2 domain-containing tyrosine phosphatase SHPTP1" Mol. Cell Biol., 1995, 15, pp. 7050-7058.

De Bruijn P. Kehrer Df, Verweij J. Sparreboom A. "Liquid chromatographic determination of ketoconazole, a potent inhibitor of CYP3A4-mediated metabolism" J. Chromatogr. B biomed Sci. Appl. 2001, 753(2), pp. 395-400.

De Veer, M.J., Holko, M. Frevel, E. Walker, S. Der,J.m. Paranjape, R.H. silverman and B.R. Williams "Functional classification of interferon-stimulated genes identified using microarrays" J. Leukoc Biol., 2001, 69, pp. 912-920.

De, B.P. et al. "Specific Interaction in Vitro and in Vivo of glyceraldehycle-e-phosphate Dehydrogenase and LA Protein with Cis-acting RNAs of Human Parainfluenze Virus Type 3" J. Biol. Chem., 1996, 271, pp. 24738-24735.

Denu, J.M. and dixon, J.E. "Protein tyrosine phosphatases: mechanisms of catalysis and regulation" Curr Opin Chem Biol, 1998, 2, pp. 633-641.

Diamond, R. H. et al. "PRL-1, A Unique Nuclear Protein Tyrosine Phosphatase, Affects Cell Growth" Mol. Cell Biol., 1994, 14, pp. 3752-3762.

Donkor, I. A. and A. M. Clark. "In vitro antimicrobial activity of aromatic diamidines and diimidazolines related to pentamidine" Eur.J. Med. Chem., 1999, 34, pp. 639-643.

Drewinko, B. et al. "Establishment of a human carcinoembryonic antigen-producing colon adenocarcinoma cell line" Cancer Res., 1976, 36, pp. 467-475.

Druker, B. J. et al. "Activity of a specific inhibitor of the BCR-ABL tyrosine kinase in the blast crisis of chronic myeloid leukemia and acute lymphoblastic leukemia with the Philadelphia chromosome" N Engl. J. Med., 2001, 344, pp. 1038-1042.

Druker, B. J. et al. "Efficacy and safety of a specific inhibitor of the BCR-ABL tyrosine kinase in chronic myeloid leukemia" N Engl. J Med., 2001, 344, pp. 1031-1037.

Eckstein, J. "Cdc25 as a potential target of anticancer agents" Investigational New Drugs, 2000, 18, pp. 149-156.

Ellery, J. M. et al. "Activation of the interleukin 2 receptor: a possible role for tyrosine phosphatases" Cell Signal, 2000, 12, pp. 367.

Elson, A., Leder, P. "Identification of a cytoplasmic, phorbol ester-inducible isoform of protein tyrosine phosphatase epsilon" Proc. Natl. Acad. Sci. USA, 1995, 92, pp. 12235-12239.

Espinoza-Delgado, I., M.C. Bosco, T. Musso, G.L. Gusella, D.L. Longo, and L. Varesio. "Interleukin-2 and human monocyte activation" J. Leukoc. Biol., 1995, 57, pp. 13.

Farinotti, R. et al. "Comparison of tissular disposition of pentamidine mesylate in the rat after aerosol or parenteral administration" J. Infect. Dis., 1989, 160, pp. 507-512.

Fauman, E. B. et al. "Structure and function of the protein tyrosine phosphatases" Trends Biochem. Sci, 1996, 21, pp. 413-417.

Fenaux, P., Chastang, C., Chevret, S., Sanz, M., Dombret, H., Archimbaud, E., Fey, M., Rayon, C., Huguet, F., Sotto, J.J., Gardin, C., Makhoul, P.C., Travade, P., Solary, E., Fegueux, N., Bordes-soule, D., Miguel, J.S., Link, H., Desablens, B., Stamatoullas, A., Deconinck, E., Maloisel, F., Castaigue, S., Preudhomme, C. and Degos, L. "A randomized comparison of all transretinoic acid (ATRA) followed by chemotherapy and ATRA plus chemotherapy and the role of maintenance therapy in newly diagnosed acute promyelocytic leukemia" The European APL Group. Blood, 1999, 94, pp. 1192-1200.

Fiaschi, T. et al. "Low molecular weight protein-tyrosine phosphatase is involved in growth inhibition during cell differentiation" J. Biol. Chem., 2001, 276, pp. 49156-49163.

Forget, G., K. A. Siminovitch, S. Brochu, S. Rivest, D. Radzioch, and M. Olivier. "Role of host phospholtyrosine phosphatase SHP-1 in the development of murine leishinaniasis" Eur. J. Immunol., 2001, 31, pp. 3185.

Forsberg, K., Valyi-Nagy, I., Heidin, C. H., Herlyn, M. and Westermark, B. "Platelet-derived growth factor (PDGF) in oncogenesis: development of a vascular connective tissue stroma in xenotransplanted human melanoma producing PDGF-BB" Proc. Natl. Acad. Sci. USA, 1993, 90, pp. 393-397.

Frank, D. A. and Sartorelli, A. C. "Alterations in tyrosine phosphorylation during the granulocytic maturation of HL-60 leukemia cells" Cancer Res., 1988, 48, pp. 52-58.

Frearson, J. A., Yi, T. and Alexander, D.R. "A tyrosine-phosphorylated 110-120-kDa protein associates with the C-terminal SH2 domain of phosphotyrosine phosphatase-1D in T cell receptor-stimulated T cells" Eur. J. Immunol., 1996, 26, pp. 1539-1543.

Gallagher, R., collins, S., Trujillo, J., Ruscetti, F. Gallo, R. "Characterization of the continuous, differentiating myeloid cell line (HL-60) from a patient with acute promyelocytic leukemia" Blood, 1979, 54: 713-733.

Gangneux, J. et al. "Experimental evaluation of second-line oral treatments of visceral leishmaniasis caused by Leishmania infantum" Antimicrob Agents Chemother., 1999, 43(1), pp. 172-174.

(56) References Cited

OTHER PUBLICATIONS

Gianni, M., Terao, M., Zanotta, S., Barbui, T., Rambaldi, A. and Garattini, E. "Retinoic acid and granulocyte colony-stimulating factor synergistically induce leukocyte alkaline phosphatase in acute promyelocytic leukemia cells" Blood, 1994, 83, pp. 1909-1921.
Gianni, M., Zanotta, S., Terao, M., Rambaldi, A. and Garattini, E. "Interferons induce normal and aberrant retinoic-acid receptors type alpha in acute promyelocytic leukemia cells: potentiation dale induction of retinoid-dependent, differentiation markers" Int. J. Cancer, 1996, 68, pp. 75-83.
Gianni, M., Kalac, Y., Ponzanelli, I., Rambaldi, A., Terao, M. and Garattini, E. "Tyrosine kinase inhibitor STI571 potentiates the pharmacologic activity of retinoic acid in acute promyelocytic leukemia cells: effects on the degradation of RARalpha and PML-RARalpha" Blood, 2001, 97, pp. 3234-3243.
Giard, D. J. et al. "In vitro cultivation or human tumors establishment of cell lines derived from a series of solid tumors" J. Natl. Cancer Inst., 1973, 51, pp. 1417-1423.
Gillis, S. et al."Biochemical and biological characterization of lymphocyte regulatory molecules. V. Identification of an interleukin 2-producing human leukemia T cell line" J. Exp. Med., 1980, 152, pp. 1709.
Goldman et al. "Principles of cancer therapy" Cecil's Textbook of medicine, W. B. Saunders Company, 2000, pp. 1060-1074.
Goldman, J. M. et al. "Targeting the BCR-ABL tyrosine kinase in chronic myeloid leukemia" N. Engl. J. Med., 2001, 344, pp. 1084-1086.
Goodwin. J. G. and Page, J. E. "A study of the excretion of organic antibonials using a polarographic procedure" Biochem. J., 1943, 37, pp. 198-209.
Goodwin, L.G. "Pentostam (sodium stibugluconate); a 50-year personal reminiscence" Trans. R Soc Trop. Med. Hyg., 1995, 89, pp. 339-341.
Gore, S. D., Weng, L. J., Jones, R. J., Cowan, K., Zilcha, M., Piantadosi, S. and Burke, P. J. "Impact of in vivo administration of interleukin 3 on proliferation, differentiation, and chemosensitivity of acute myeloid leukemia" Clin. Cancer Res., 1995, 1, 295-303.
Gorre, M. E., M. Mohammed, K. Ellwood, N. Hsu, R. Paquette, P. N. Rao and C. L. Sawyers. "Clinical Resistance to STI-571 Cancer Therapy Caused by BCR-ABL Gene Mutation or Amplification" Science, 2001, 293, pp. 876-880.
Green, M. C. et al. "Motheaten, an immunodeficient mutant of the mouse. I. Genetics and pathology" J. Hered., 1975, 66, pp. 250.
Greenlee, R. T. et al. "Cancer statistics" CA Cancer J. Clin., 2001, 51, pp. 15.
Guan, K-L, Dixon, J.E. "Evidence for Protein-tyrosine-phosphatase Catalysis Proceeding via a Cystein-Phosphate Intermediate" J. Biol. Chem., 1991, 266, pp. 17026-17030.
Hague, S. J. et al. "Protein-tyrosine phosphatase Shp-1 is a negative regulator of IL-4- and IL-13-dependent signal transduction" J. Biol. Chem., 1998, 273, pp. 33893-33896.
Haque, S. J. et al. "Roles of protein-tyrosine phosphatases in Stat I alpha-mediated cell signaling" J. Biol. Chem., 1995, 270, pp. 25709-25714.
He, L. Z., Merghoub, T. and Pandolfi, P. O. "In vivo analysis of the molecular pathogenesis of acute promyelocytic leukemia in the mouse and its therapeutic implications" Oncogene, 1999, 18, pp. 5278-5292.
Heffetz, D., Bushkin, I., Dror, R. and Zick, Y. "The insulinomimetic agents $H_2O_2$ and vanadate stimulate protein tyrosine phosphorylation in intact cells" J. Biol. Chem., 1990, 265, pp. 2896-2902.
Helson, L. et al. "Human neuroblastoma in nude mice" Cancer Res., 1975, 35, pp. 2594-2599.
Herwaldt, B. L. and Berman, J. D. "Recommendations for treating leishmaniasis with sodium stibugluconate (Pentostam) and review of pertinent clinical studies" Am. J. Trop. Med. Hyg., 1992, 46, pp. 296-306.

Herwaldt, B. L., Kaye, E. T., Lepore, T.J., Berman, J.D. and Baden, H. P. "Sodium stibogluconate (Pentostam) overdose during treatment of American cutaneous leishmaniasis" J. Infect. Dis., 1992, 165, pp. 968-971.
Hirai, H., Shimazaki, C., Yamagata, N., Goto, H., Inaba, T., Kikuta, T., Sumikuma, T., Sudo, Y., Ashihara, E., Fujita, N., Hibi, S., Imashuku, S., Ito, E. and Nakagawa, M. "Effects of thrombopoietin (c-mpl ligand) on growth of blast cells from patients with transient abnormal myclopoiesis and acute mycloblastic leukemia" Eur. J. Haematol, 1997, 59, pp. 38-46.
Holloway, A. F. et al. "Regulation of cytokine gene transcription in the immune system" Mol. Immunol., 2001, 38, pp. 567-580.
Hooft Van Huijsduijnen, R. "Protein tyrosine phosphatases: counting the trees in the forest" Gene, 1998, 225, pp. 1-8.
Hsu, H. C., Tsai, W. H., Hsu, M. L., Ho, C. H. and Wang, S. Y. "Effects of colony-stimulating factors on the all-trans retinoic acid-induced differentiation of acute promyelocytic leukemic cells" Chung Hua I Hsuch Tsa Chih, 1996, 57, pp. 93-99.
Hunter, T. "The role of tyrosine phosphorylation in cell growth and disease" Harvey Lect., 1998, 94: 81-119.
Huyer, G., S. et al. "Mechanism of inhibition of protein-tyrosine phosphatases by vanadate and pervanadate" J. Biol. Chem., 1997, 272, pp. 813-851.
Idres, N., Benoit, G., Flexor, M.A., Lanotee, M. and Chabot, G.G. "Granulocytic differentiation of human NB4 promyelocytic leukemia cells induced by all-trans retinoic acid metabolites" Cancer Res., 2001, 61, pp. 700-705.
Ihle, J. N., Thierfelder, W., Teglund, S., Stravapodis, D., Wang, D., Feng, J. and Parganas, E. "Signaling by the cytokine receptor superfamily" Ann. NY Acad. Sci., 1998, 865, pp. 1-9.
Irie-Sasaki, J., Sasaki, T., Matsumoto, W., Opaysky, A., Cheng, M., Welstead, G., Griffiths, E., Krawczyk, C., Richardson, C.D., Aitken, K., Iscove, N., Koretzky, g., Johnson, P., Liu, P., Rothstein, D.M. and Penninger, J. "CD45 is a JAK phosphatase and negatively regulates cytokine receptor signaling" Nature, 2001, 409, 349-354.
James, S. Y., Williams, M. A., Kelsey, S. M., Newland, A. C. and Colston, K. W. "Interaction of vitamin D derivatives and granulocyte-macrophage colony-stimulating factor in leukacmic cell differentiation. Lukemia" 1997, 11, pp. 1017-1025.
Jennings, C. D., Foon, K. A. "Recent Advances in Flow Cytometry: Application to the Diagnosis of Hematologic Malignancy" Blood, 1997, 90, pp. 2863-2892.
Jiang, Y et al. "Inhibition of anchorage-independent growth and lung metastasis of A549 lung carcinoma cells by I kappa B beta" Oncogene, 2001, 20, pp. 2254-2263.
Jiao, H., Berrada, K., Yang, W., Tabrizi, M., Platanias, L. C. and Yi, T. "Direct association and dephosphorylation of Jak2 kinase by SH2 domain-containing protein tyrosine phosphatasc SHP-1" Mol. Cell. Biol., 1996, 16, pp. 6985-6992.
Jiao, H., Yang, W., Berrada, K., Tibrizi, M., Shultz, L. and Yi, T. "Macrophages from motheaten viable motheaten mutant mice show increased proliferative response to GM-CSF: detection or potential HCP substrates in GM-CSF signal transduction" Exp. Hematol., 1997, 25, pp. 592-600.
Johnson, K. G., LeRoy, F. G., Borysiewicz, L. K. and Matthews, R.J. "TCR signaling thresholds regulating T cell development and activation are dependent upon SHP-1" J. Immunol., 1999, 162, pp. 3802-1383.
Joliat, M. J. et al. "Absence of CD5 dramatically reduces progression of pulmonary inflammatory lesions in SHP-1 protein-tyrosine phosphatase-deficient viable motheaten mice" J. Autoimmun., 2002, 18, pp. 105.
Kemp, M., Kurtzhals, J. A., Kliarazmi, A. and Theander, T. G. "Interferon-gamma and interleukin-4 in human Leishmania donovani infections" Immunol. Cell Biol., 1993, 71, pp. 583-587.
Kikawa, K. D. et al. "Regulation or the EphA2 kinase by the low molecular weight tyrosine phosphatase induces transformation" J. Biol. Chem., 2002, 277, pp. 39274-39279.
Kitamura, Y et al. "Inhibition of constitutive nitric oxide synthase in the brain by pentamidine, a calmodulin antagonist" Eur. J. Pharm., 1995, 289, pp. 299-304.
Klimp, A. H. et al. "A potential role of macrophage activation in the treatment or cancer" Crit. Rev. Oncol. Hematol. 2002, 44, pp. 143.

(56) References Cited

OTHER PUBLICATIONS

Klingmuller, U., Lorenz, U., Cantley, L.C., Neel, B. G. and Lodish, H. F. "Specific recruitment or SH-PTPI to the erythropoietin receptor causes inactivation ofJAK2 and termination of proliferative signals" Cell, 1995, 80, pp. 729-738.

Kogan, S. C. and Bishop, J. M. "Acute promyelocytic leukemia: from treatment to genetics and back" Oncogene, 1999, 18, pp. 5261-5267.

Kong, W. et al. "PRL PTPase Expression is Developmentally Regulated With Tissue-Specific Patterns in Epithelial Tissues" Am. J. Physiol. Gastrointest Liver Physiol., 2001, 279, pp. G613-G621.

Kumar, V. "Melatonin: A master hormone and a candidate for universal panacea" Indian Journal of Experimental Biology, 1996, 34, pp. 391-402. (Abstract only).

Lanotte, M., Martin-Thouvenin, V., Najman, S., Balerini, P., Valensi, F. and Berger, R. "NB4, A maturation inducible cell line with t(15;17) marker isolated from a human acute promyelocytic leukemia (M3)" Blood, 1991, 77, pp. 1080-1086.

Lee, T. et al. "Acquisition of high-affinity, SH2-targeted ligands via a spatially focused library" J. Med. Chem., 1999, 42(5), pp. 784-787.

Leibovitz, A., Stinson, J. C., McCombs, W. R., McCoy, C. E., Mazur, K. C., mabry, N. D. "Classification of human colorectal adenocarcinoma cell lines" Cancer Res., 1976, 36, pp. 4562.

Li, J. et al. "Successful therapy of chronic, nonhealing murine cutaneous leishmaniasis with sodium stibogluconate and gamma interferon depends on continued interleukin-12 production" Infect. Immun., 1997, 65(8), pp. 3225-3230.

Lindner, D. J., Borden, E. C. and Kalvakolanu, D. V. "Synergistic antitumor effects of a combination of interferons and retinoic acid on human tumor cells in vino and in vivo" Clin. Cancer Res., 1997, 3, pp. 931-937.

Liu, J. et al. "Mediation of the DCC apoptotic signal by DIP13 alpha" J. Bio. Chem., 2002, 277, pp. 26281.

Liu, Y. et al. "Inhibition of in vitro splicing of a group I intron of *Pneuocyctis carinii*" J. Euk. Microbiol., 1994, 41, pp. 31-38.

Lorenz, U. et al. "Lek-dependent tyrosyl phosphorylation of the phosphotyrosinc phosphatase SH-PTP1 in murine T cells" Mol. Cell. Biol., 1994, 14, pp. 1824-1834.

Lowenberg, B., Downing, J. R. and Burnett, A. "Acute myeloid leukemia" N Engl. J. Med., 1999, 341, pp. 1051-1062.

Lu, C., Rak, J. W., Kobayashi, H. and Kerbel, R. S. "Increased resistance to oncostatin M-induced growth inhibition of human melanoma cell lines derived from advanced-stage lesions" Cancer Res., 1993, 53, pp. 2708-2711.

Mahmoud, A.A. and Warren, K. S. "Algorithms in the diagnosis and management of exotic disease. XXIV. Leishmaniases" J. Infect. Dis., 1977, 136, pp. 160-163.

Margolin, K.A. "Interleukin-2 in the treatment of renal cancer" Semin. Oncol., 2000, 27, pp. 194.

Martiny, A., Vannicr-Santos, M.A., Borges, V.M., Meyer-Fernandes, J.R., Assreuy, J., Cunha e Silva, N.L. and de Souza, W. "Leishmania-induced tyrosine phosphorylation in the host macrophage and its implication to infection" Eur. J. Cell Biol., 1996, 71, pp. 206-215.

Masztalerz, A., N. Van Rooijen, W. Den Otter, and L.A. Everse. 2003. "Mechanisms of macrophage cytotoxicity in IL-2 and IL-12 mediated tumor regression" Cancer Immunol Immunother, 2003, 52, pp. 235.

Matin, S.F., Rackley, R.R., Sadhukhan, P.C., Kim, M.S., Novick, A.C., Bandyopadhyay, S.K. "Impaired alph-Interferon Signaling in Transitional Cell Carcinoma: Lack of p18 Expression in 5637 Cells" Cancer Res., 2001, 61, pp. 2261-2266.

Matte, C., Marquis, J.F., Blanchette, J., Gros, P., Faure, R., Posner, B.I. and Olivier, M. "Peroxovanadium-mediated protection against murine leishmaniasis: role of the modulation of nitric oxide" Eur. J. Immunol., 2000, 30, 2555-2564.

Matter, W.F., et al., Biochem Biophys Res Cummun, 2001, 283, pp. 1061-1068.

Mattison, C.P., S.S. Spencer, K.A. Kresge, J. Lee and I.M. Ota. "Differential regulation oldie cell wall integrity mitogen-activated protein kinase pathway in budding yeast by the protein tyrosine phosphatases Ptp2 and Ptp3" Mol. Cell. Biol., 1999, 19, pp. 7651-7660.

Mauro, M.J. and Druker, B.J. "Chronic myelogenois leukemia" Curr. Opin. Oncol., 2001, 13, pp. 3-7.

Melnick, A. and Lieht, J.D. "Deconstructing a disease: RARalpha, its fusion partners, and their roles in the pathogensis of acute promyelocytic leukemia" Blood, 1999, 93, pp. 3167-3215.

Metcalf, D. "Cellular hematopoiesis in the twentieth century" Semin Hematol, 1999, 36, pp. 5-12.

Meurs, E. and Hovanessian, A.G. "Alpha-interferon inhibits the expression of heavy chain mu messenger RNA in Daudi cells" Embo. J., 1988, 7, pp. 1689-1696.

Mickey, D.D., Stone, K.R., Wunderli, H., Mickey, G.H., Vollmer, R.T. and Paulson, D.F. "Heterotransplantation of a human prostatic adenocarcinoma cell line in nude mice" Cancer Res., 1977, 37, pp. 4049-4058.

Miletti, K.E. and MJ. Leibowitz, "Pentamidine inhibition of group I intron splicing in Candida albicans correlates with growth inhibition" Antimicrob. Agents Chemother., 2000, 44, pp. 958-966.

Miyagishi, M., Taira, K. "U6 promoter-driven siRNAs with four uriding 3' overhangs efficiently suppress targeted gene expression in mammalian cells" Nature Biotech., 2002, 19, 497-500.

Montagna, M., O. Serova, B.S. Sylla, J. Feuteun, and G.M. Lenoir, "A 100-kb physical and transcriptional map around the EDH17β2 gene: identification of three novel genes and a pseudogene of a human homologue of the rate PRL-I tyrosine phosphatase" Hum. Genet., 1995, 96, 532-528.

Mossmann, T., "Rapid calorimetric assay for cellular growth and survival: application to proliferation and cytoxicity assays" J. Immunol. Methods, 1983, 65, pp. 55-63.

Motzer, RJ., and P. Russo, "Systemic Therapy for renal cell carcinoma" J. Urol., 2000, 163, pp. 408.

Mulders, P., R. Figlin, J.B. deKenion, R. Wiltrout, M. Linehan, D. Parkinson, W. deWolf, and A. Belldegrun. "Renal cell carcinoma: recent progress and future directions" Cancer Res., 1997, 57, pp. 5189.

Murphy, G.P., and W.J. Hrushesky. "Amurine renal cell carcinoma" J. Natl. Cancer Inst., 1973, 50, pp. 1013.

Murray, H. W. et al. "Treatment of experimental visceral Leishmaniasis in a T-cell-deficient host: response to Amphotericin B and pentamidine" Antimicrobial Agents and Chemotherapy, 1993, 37, pp. 1504.

Murray, H.W. and S. Delph-Etienne. "Roles of endogenous gamma interferon and macrophage microbicidal mechanisms in host response to chemotherapy in experimental visceral leishmaniasis" Infect. Immun., 2000, 68, pp. 288-293.

Murray, H.W. et al., "Interleukin-12 Regulates the Response to Chemotherapy in Experimental Visceral Leishimaniasis" J. Infect Dis., 2000, 182, pp. 1497.

Murray, H.W., et al., Immunochemotherapy for Intracellular Leishmania donovani Infection: Gamma Interferon Plus Pentavalent Antimony. J. Infect. Dis., 1988, 157, pp. 973-978.

Murray, H.W., Mj. Oca, A.M. Granger, and R.D. Schreiber, "Requirement for T cells and effect of lymphokines in successful chemotherapy for an intracellular infection. Experimental visceral leishmaniasis" J. Clin. Invest., 1989, 83, pp. 1253.

Myers, M. P. et al. "TYK2 and JAK2 are substrates of protein-tyrosine phosphatase 1B" J. Biol. Chem., 2001, 276, pp. 47771-47774.

Naftalovich, S., E. Yefenof and Y. Eilam, "Antitumor effects of ketoconazole and trifluoperazine in murine T-cell lymphomas" Cancer Chemother Pharmacol, 1991, 28, pp. 384-390.

Nagatsuka, I. et al. "Inhibitory effect of a selective cyclooxygenase-2 inhibitor on liver metastasis of colon cancer" Int. J. Cancer, 2002, 100, pp. 515-519.

Nandan, D. and Reiner, N.E. "Attenuation of gamma interferon-induced tyrosine phosphorylation in mononuclear phagocytes infected with leishmania donovani: selective inhibition of signaling through Janus kinases and Stat1" Infect Immun., 1995, 63, pp. 4495-4500.

(56) References Cited

OTHER PUBLICATIONS

Nandan, D., Knutson, K.L., Lo, R. and Reiner, N.E. "Exploitation of hose cell signaling machiner: activation of macrophage phosphotyrosine phosphates as a novel mechanism of molecular microbial pathogenesis" J. Leukoc. Biol., 2000, 67, pp. 464-470.

Nandan, D., Lo, R. and Reiner, N.E. "Activation of phosphotyrosine phosphatase activity attenuates mitogen-activated protein kinase signlaing and inhibits c-FOS and nitric oxide synthase expression in macrophages infected with Leishmania donovai" Infect. Immun., 1999, 67, pp. 4055-4063.

Nanden, D., T. Yi, M. Lopez, C. Lai, and N.E. Reiner, "Leishmania EF-lalpha activates the Src homology 2 domain containing tyrosine phosphatase SHP-I leading to macrophage deactivation"J. Biol Chem., 2002, 277, pp. 50190.

Nilsson, I and I. Hoffmann. "Cell cycle regulation by the Cdc25 phophatase family" Progress in Cell Cycle Research, 2000, 4, pp. 107-114.

O'Dwyer, M.E. and Druker, BJ. "Status of bcr-abl tyrosine kinase inhibitors in chronic myelogenous leukemia" Curr. Opin. Oncol., 2000, 12, pp. 594-597.

Oka, T. et al. "Immunosuppression in organ transplantation" Jpn. J. Pharmacol., 1996, 71, pp. 89-100 (Abstract only).

Olivier, M., Romero-Gallo, B. J., Matte, C., Blanchette, J., Posner, B.I., Tremblay, M.J. and Faure, R. "Modulation of Interferon-gamma-induced macrophage activation by phosphotyrosinc phosphatases inhibition. Effect on murine Leishmaniasis progression" J. Biol. Chem., 1998, 273, pp. 13944-13949.

Osol, A. "Chapter 27: Structure-activity relationship and drug design" Remington's Pharmaceutical Sciences (16th Edition), Mack Publishing, 1980, pp. 420-425.

Pallen, C.J. The receptor-like protein tyrosine phosphatase alpha: a role in cell proliferation and oncogenesis. Cell Biology, 1998:4:403-408.

Parmiani, G., Rivoltini, L., Andreola, G. and Carrabba, M. "Cytokines in cancer therapy" Immunol. Lett., 2000, 74, pp. 41-44.

Parsons, R. "Phosphatases and tumorigenesis" Current Opinion in Oncology, 1998, 10, pp. 88-91.

Pathak, M. K. "Sodium stibogluconate anti-cancer activity: targeting PRL family PTPase" (submitted for publication).

Pathak, M. K. et al. "Pentamidine is an in hibitor of PRL phophatases with anticancer activity" Molecular Cancer Therapeutics, 2002, 1, pp. 1255.

Pathak, M.P. and T. Yi, "Sodium Stibogluconate is a Potent Inhibitor of Protein Tyrosine Phosphatases and Augments Cytokine Response in Hemopoietic Cell Lines" The Jounal of Immunology, 2001, 167, pp. 3391-3397.

Pathak, Mk, X. Hu and T.Yi, "Effects of Sodium Stibogluconate on Differentiation Proliferation of Human Myeloid Leukemia Cell Lines in Vitro" Leukemia, 2002, 16, pp. 2285-2291.

Patrick, D. A. "Synthesis and anti-Pneumocystis carinii pneumonia activity of novel dicationic and dibenzothiophenes and orally active prodrugs" Eur. J. Med. Chem., 1999, 34, pp. 575.

Perez, J.M., J.M. Requena, d. Craciunescu, J.C. Domino and c. Alonso. "Binding of Pt-pentamidine to nucicosomal DNA. Studies of the antiproliferative activity of the drug against human cancer cells" Chem. Biol. Interact., 1993, 89, pp. 61-72.

Perez, J.M., M.C. Navarro-Ranninger,J.M. Requena, A. Jimenez-Ruiz, E. Parrondo, D. Craciunescu, M.C. Lopez and C. Alonso. "DNA binding properties and antileukemic (L1210) activity of a Pt-pentamidine complex" Chem. Biol. Interact., 1991, 77, pp. 311-355.

Peters, C.S., Liang, X., Li, S., Kannan, Sl, Peng, Y., Taub, R., Diamond, R.H. "ATF-7, a Novel bZIP Protein, Interacts with the PRL-1 Protein-tyrosine Phospatase" J. Biol. Chem., 2001, 275, pp. 13718-13726.

Platanias, L.C., Fish, E.N., "Signaling pathways activated by interferons" Exp. Hematol., 1999, 27, pp. 1583.

Platanias, L.C., P. Domanski, O.W. Nadeau, T. Yi, S. Uddin, E. Fish, B.G. Neel and O.R. Colamonici. "Identification of a domain in the beta subunit of the type I interferon (IFN) receptor that exhibits a negative regulatory effect in the growth inhibitory action of type I IFNs" J. Biol. Chem., 1993, 273, pp. 5577-5581.

Puri, R.K. and Seigel, J.P. "Interleukin-4 and cancer therapy" Cancer Invest., 1993, 11, pp. 473-479.

Qin, Z., J. Schwartzkopff, F. Pradera, T. Kammertoens, b. Seliger, H. Pircher, and T. Blakenstein. "A critical requirement of interferon gamma-medicated angiostasis for tumor rejection by CD8+T cells" Cancer Res., 2003, 63, pp. 4095.

Raelson, J.V., Nervi, C., Rosenauer, A., Benedetti, L., Monczak, Y., Pearson, M., Pelicci, P.G. and Miller, W., Jr. "The PML/RAR alpha oncoprotein is a direct molecular target of retinoic acid in acute promyelocytic leukemia cells" Blood, 1996, 88, pp. 2826-2832.

Ramesh, R. et al. "Successful treatment of primary and disseminated human lung cancers by systemic delivery of tumor suppressor genes using an improved liposome vector" Molecular Therapy, 2001, 3, pp. 337-350.

Rees, P.H., M.I. Keating P. A. Kager and W.T. Hockmeyer, "Renal clearance of pentavalent antimony (sodium stibogluconate)" Lancet, 1980, 2, pp. 226-229.

Rice, G.P., Oger, J., Duquette, P., Fransie, G.S., Belanger, M., Laplante, S., Grenier, J.F., "Treament with interferon beta-lb improves quality of life in multiple sclerosis" Can. J. Neural. Sci., 1999, 26, pp. 276.

Rickets, K. et al. "The clinical presentation of generalized anxiety in primary-care settings: practical concepts of classification and management" J. Clin. Psychiatry., 1997, 58, pp. 4-10 (Abstract only).

Roberts, W.L. and P.M. Rainey. "Antileishmanial activity of sodium stibogluconate fractions" Antimicrob. Agents Chemother., 1993, 37, pp. 1842-1846.

Roberts, W.L.J. Hariprashad, P.M. Rainey and H.W. Murray. "Pentavalent antimony-mannan conjugate therapy of experimental visceral leishmaniasis" Am. J. Trop. Med. Hyg., 1996, 55, pp. 444-446.

Rochiltz, D.F., L.E. Damon, M.B. Russi, A. Geddes and E.C. Cadman. "Cytotoxicity of ketoconazole in malignant cell lines" Cancer Chemother. Pharmacol, 1988, 21, pp. 319-322.

Rosenberg, S.A. "Progress in human tumor immunology and immunotherapy" Nature, 2001, 411, pp. 380-384.

Rosenberg, S.A. "Interleukin-2 and the development of immunotherapy for the treatment of patients with cancer" Cancer J. Sci. Am., 2000, pp. S2.

Safai, B., Sarngadharan, M.G., Groopman, J.E., Arnett, K., Popovic, M., Sliski, A., Schupbach, J. and Gallo, R.C. "Seroepidemiological studies of human T-lymphotropic retrovirus type III in acquired immunodeficiency syndrome" Lancet, 1984, 1, pp. 1438-1440.

Saha, S., Bardclli, A., Buckhaults, P., Veleulescu, V.E., Rago, C., St. Croix, B., Romans, K.E., Choti, M.A., Lengauer, C., Kinzler, K.W., Vogelstein, B. "A phosphatase associated with metastasis of colorectal cancer" Science, 2001, 294, pp. 1343-1346.

Salem, M., Delwel, R., Mahmoud, L.A., Clark, S., Elbasousy, E.M. and Lowenberg, B. "Maturation of human acute myeloid leukaemia in vitro: the response to five recombinant haematopoietic factors in a serum-free system" Br. J. Haematol., 1989, 71, pp. 363-370.

Samlowski, W.E., R. Petersen, S. Cuzzocrea, H. Macarthur, D. Burton, J.R. McGregor, and D. Salvermini, 2003. "A nonpeptidyl mimic of superoxide dismutase, M40403, inhibits dose-limiting hypotension associated with interleukin-2 and increases its antitumor effects" Nat. Med., 9, pp. 750.

Sands, M. et al. "Pentamidine: a Review" Reviews of Infectious Diseases, 1985, 7, pp. 625-634.

Schlesinger, M., Rabinowitz, R., Kertes, T., Ravid, Z. and Goldblum, N. "Antibodies to human T lymphocytes in xenoantisera elicited with a new immature T-cell line (Peer)" Thymus, 1981, 2, pp. 235-243.

Schultz, L.D., D.R. Coman, C.L. Bailey, W.G. Beamer, and C.L. Sidman. "'Viable motheaten' a new allele at the motheaten locust" I. Pathology. Am. J. Pathol., 1984, 116, pp. 179.

Schultz, L.D., P.A. Schweitzer, T.V. Rajan, T.Yi,J.N. Ihle, R.J. Matthews, M.L. Thomas, and D.R. Beier, 1993. "Mutations at the murine motheaten locust are within the hematopoietic cell protein-tyrosine phosphatase (Hcph) gene" Cell, 1993, 73, pp. 1445.

(56) References Cited

OTHER PUBLICATIONS

Shen, K. et al. "Acquisition an specific and potent PTP1B inhibitor from a novel combinatorial library and screening procedure" J. Biol. Chem., 2001, 276, pp. 47311-47319.

Si, X. et al. "Interaction of Farnesylated PRL-2, a protein-tyrosine phosphatase, with the beta-subunit of geranylgertmyltransferase II" J. Biol. Chem., 2001, 276, pp. 32875-32882.

Smith, H. et al. "Hormone replacement therapy in the menopause: a pro opinion" CA Cancer J. Clin., 1996, 46, pp. 343-363 (Abstract only).

Snapper, I. "Stilbamidine and pentamidine in multiple myeloma" JAMA, 1947, 133, pp. 157-161.

Sonouchi, K., T.A. Hamilton, C.S. Tannenbaum, R.r. Tubbs, R. Bukowski, and J.H. Finke. "Chemokine gene expression in the murine renal cell carcinoma, RENCA, following treatment in vivo with interleukin-alpha and interleukin-2" Am. J. Pathol., 1994, 144, pp. 747.

Squires, K.E., Schreiber, R.D., McElrath, M.J., Rubin, B.Y., Anderson, S.L., Murray, H.W., "Experimental visceral leishmaniasis: role of endogenous IFN-gamma in hose defense and tissue granulomatous response" J. Immunol., 1989, 143, pp. 4244.

Stanhope-Baker, P. and Williams, B.R. "Identification of connective tissue growth factor as a Large of WTI transcriptional regulation" J. Biol. Chem., 2000, 275, pp. 38139-38150.

Stark, G.R. "Genetic analysis of interfercon and other mammalian signaling pathways" Harvey Lect., 1997, 93, pp. 1-16.

Steck, E.A. "The leishmaniases" Prog. Drug Res., 1974, 18, pp. 289-351.

Sun, H. et al. "Inhibition of Ras induced DNA synthesis by expression of the phosphatase MKP-1" Science, New Series, 1994, 266, pp. 285-288.

Sundar, S., P.R. Shiba, N.K. Agrawal, R. Srivastava, P.N. Rainey, J.D. Berman, H.W. Murray and V.P. Singh. "A cluster of cases of sever cardiotoxicity among kala-azar patients treated with a high-osmolarity lot of sodium antimony gluconate" Am. J. Trop Med. Hyg., 1998, 59, pp. 139-143.

Sundstrom, C. and Nilsson, K. "Establishment and characterization of a human histiocytic lymphoma cell line (U-937)" Int. J. Cancer., 1996, 17, 565-577.

Tabiti, K., D.R. Smith, H.S. Goh and C.I. Pallen. "Increased mRNA expression of the receptor-like protein tyrosine phosphatase alpha in late stage colon carcinomas" Cancer Lett., 1995, 93, pp. 239-248.

Tabrizi, M. et al. "Reduced Tyk2/SHP-1 interaction and lack of SHP-1 mutation in a hundred of familial hemophagocytic lymphohistiocytosis" Leukemia, 1998, 12, pp. 200-206.

Tallman, M.S., Anderson, J.W. Schiffer, C.A., Applebaum, F.R., Feusner, J.H., Ogden, A., Shepherd, L., Rowe, J.M., Francois, C., Larson, R.S. and Wiemik, P.H. "Clinical description 44 patients with acute promyelocytic leukemia who developed the retinoic acid syndrome" Blood, 2000, 95, pp. 90-95.

Tanuma, N., K. Nakamura, H. Shima and K. Kikuchi. "Protein-tyrosine phosphatase PTPepsilon C inhibits Jak-STAT signaling and differentiation induced by interleukin-6 and leukemia inhibitory factor in M1 leukemia cells" J. Biol. Chem., 2000, 275, pp. 28216-28221.

Tbakhi, A. et al. "Fixation conditions for DNA and RNA in situ hybridization: a reassessment of molecular morphology dogma" Am. J. Pathol., 1998, 152, pp. 35-41.

Thomasson, M.J., Yi, T., Raychaudhuri, B., Malur, A. and Kavuru, M.S. "Pulmonary alveolar proteinosis is a disease of decreased availability of GM-CSF rather than an intrinsic cellular defect" Clin. Immunol., 2000, 95, pp. 85-92.

Tidwell, R. R. et al. "Development of pentamidine analogues as new agents for the treatment of *Pneumocystis carinii* pneumonia" Annals NY Acad. Sci., 1990, 616, pp. 421-441.

Tolida, S., Yang, G.s., Ashman, L.K., McCulloch, E.A. and Minden, M.D. "Relationship between c-Kit expression and proliferation in acute myeloblastic leukemia cell lines" J. Cell Physiol., 1993, 154, pp. 410-418.

Tonks, N.K. and B.G. Neel. "Combinatorial control of-the specificity of protein tyrosine phosphatases" Curr Opin. Cell Biol, 2001, 13, pp. 182-195.

Trowbridge, I.S. and M.L. Thomas, "CD45: an emerging role as a protein tyrosine phosphatase required for lymphocyte activation and development" Ann. Rev. Immunol., 1994, 12, pp. 85-116.

Tsui, H.W., Siminovitch, K. A., de Souze, L. and Tsui, F.W. "Motheaten and viable motheaten mice have mutations in the haematopoietic cell phosphatase gene" Nature Genetics, 1993, 4, pp. 124-129.

Uddin, S., Grumbach, I.M., Yi, T., Colamnoici, O.R. and Plantanias, L.C. "Interferon alpha activates the tyrosine kinase Lyn in haemopoietic cells" Br. J. Haematol., 1998, 101, pp. 446-449.

Van Haelst-Pisani, et al., "A phase II study of recombinant human alpha-interferon in advanced hormone-refractory prostate cancer" Cancer, 1992, 70, pp. 2310-2312.

Van Moorsclaar, R.J., P. van Stratum, C. Borm, F.M. Debruyne and J.A. Schalken. "Differential antiproliferative activities of alpha- and gamma-interferon and tumor necrosis factor alone or in combinations against two prostate cancer xenografts muisplanted in nude mice" Prostate, 1991, 18, pp. 331-344.

Wang, C., Curtis, J.E., Minden, M.D. and McCulloch, E.A. "Expression of a retinoic acid receptor gene in myeloid leukemia cells" Leukemia, 1989, 3, pp. 264-269.

Wang, Q. et al. "Analysis of stromal-epithelial interactions in prostate cancer identifies PTPCAAX2 as a potential oncogene". Cancer Letters, 2002, 175, pp. 63-69.

Wick, W. et al. "Transforming growth factor-beta: a molecular target for the future therapy of glioblastoma" Curr. Pharm. Des., 2006, 12(3), pp. 341-349.

Wickrema, A., F. chen, F. Namin, T. Yi, S. Ahmad, s. Uddin, Y.H. Chen, L. Feldman, W. Stock, R. Hoffman and L. C. Platanias, "Defective expression of the SHP-1 phosphatase in polycythemia vera" Exp. Hematol., 1999, 27, pp. 1124-1132.

Williams and Wilkins, "Myeloma" and "Multiple myeloma" Stedman's Medical Dictionary, 1990, pp. 1013.

Wolf, N. G. et al. "Analysis of ovarian borderline tumors using comparative genomic hybridization and fluorescence in situ hybridization" Genes, Chromosomes & Cancer, 1999, 25, pp. 307-315.

Wu, D.W., Stark, K.C., Dunnington, D., Dillon, S.B., Yi, T., Jones, C. and Pelus, L.M. "SH2-Containing protein tyrosine phosphatase-1 (SHP-1) association with Jak2 in UT-7/Epo cells" Blood Cells Mol. Dis., 2000, 26, pp. 15-24.

Wu, H-C. et al. "Derivation of androgen-independent human LNCaP prostatic cancer cell sublines: role of bone stromal cells" Int. J. Cancer, 1994, 57, 406-412.

Yamazaki, T. et al. "Secondary structure and signal assignments of human-immunodeficiency-virus-1 protease complexed to a novel, structure-based inhibitor" Eur. J. Biochem., 1994, 219, pp. 707-712.

Yang, W. et al. "SHP-1 deficiency in B-lineage cells is associated with heightened lyn protein expression and increased lyn kinase activity" Experimental Hematology, 1998, 26, pp. 1126-1132.

Yang, W., Tabrizi, M., Berrada, K. and Yi, T. "SHP-1 C-terminus interacts with novel substrates p32/p30 during Epo and IL-3 mitogenic response" Blood, 1998, 91, pp. 3746-3755.

Yetter, A., Uddin, S., Krolewski,J.J.,Jiao, H., Yi, T. and Platanias, L.C. "Association of the interferon-dependent tyrosine kinase Tyk-2 with the hematopoietic cell phosphatase" J. Biol. Chem., 1995, 270, pp. 18179-18182.

Yi, T. and Ihle,J.N. "Association of hematopoictic cell phosphatase with c-Kit after stimulation with c-Kit ligand" Molecular & Cellular Biology, 1993, 13, pp. 3350-3358.

Yi, T., Cleveland, J.L., Ihle, J.N., "Identification of novel protein tyrosine phosphatases of hematopoictic cells by polymerase chain reaction amplification" Blood, 1991, 78, pp. 2222-2228.

Yi, T., Gilbert, D.J., Jenkins, N.A., Copeland, N.G. and Ihle, J.N. "Assignment of a novel protein tyrosine phosphatase gene (Hcph) to mouse chromosome 6" Genomics, 1992, 14, pp. 793-795.

Yi, T., M. Pathak, D. Lindner, M. Zhou, K. Fan. "SHP-1 Protein tyrosine phosphatase as a target molecule in anti-tumor immune therapies: SHP-1 Inhibitor SSG interacts with IL-2 to increase anti-murine renal tumor immunity" 16th EORTC-NCI-AACR Sym-

(56) References Cited

OTHER PUBLICATIONS posium on Molecular Targets and Cancer Therapeutics, Geneva, Switzerland, Sep. 28-Oct. 1, 2004.
Yi, T., M.K. Pathak, d.J. Lindner, and E.C. Borden. "PtPase Inhibitor Sodium Stibogluconate Inhibits the Growth of Human cancer Cell Lines in Vitro and in Vivo and Synergizes with IFNa/b" Blood, 2001, 98(11) pp. 301a.
Yi, T., M.K. Pathak, d.J. Lindner, M.E. Ketterer, C. Farver, and E.C. Borden. "Anticancer activity of sodium subogluconate in synergy with IFNs" J. Immunol., 2002, 169, pp. 5978.
Yi, T., Mui, A.L., Krystal, G. and Ihle, J.N. "Hematopoietic cell phosphatase associates with the interleukin-3 (IL-3) receptor beta chain and down-regulates IL-3-induced tyrosine phosphorylation and mitogenesis" Molecular & Cellular Biology, 1993, 13, pp. 7577-7586.
Yi, T., Zhang,J., Miura, O. and Ihle, J.N. "Hematopoictic cell phosphatase associates with erythropoietin (Epo) receptor after Epo-induced receptor tyrosine phosphorylation: identification of potential binding sites" Blood, 1995, 85, pp. 87-95.
Yi, T.L., Cleveland,J.L. and Ihle, J.N. "Protein tyrosine phosphatase containing SH2 domains: characterization, preferential expression in hematopoietic cells and localization to human chromosome 12p12-p13" Molecular & Cellular Biology, 1992, 12, pp. 836-846.
Yoshida, J., N. Shibuya, T. Kobayashi, and N. Kageyama. "Sensitivity to 1-(4-amino-2-methyl-5-pyrimidinyl)methyl-3-(2-chloroethyl)-3-nitrosourea hydrochloride (ACNU) of glioma cells in vivo and in vitro" Cancer, 1982, 50, pp. 410-418.
You, M., D.H. 'Yu and g.s. Geng. "Shp-2 tyrosine phosphatase functions as a negative regulator of the interferon-stimulated Jak/Stat pathway" Mol. Cell Biol., 1999, 19, pp. 2416-2424.
Zanke, B., Squire, J., Griesser, H., Henry, M., Suzuki, H., Patterson, B., Minden, M. and Mak, T.W. "A hematopoietic protein tyrosine phosphatase (HePTP) gene that is amplified and overexpressed in myeloid malignancies maps to chromosome 1q32.1" Leukemia, 1994, 8, pp. 236-244.
Zeng, Q., Si, X., Horstmann, H., Xu, Y., Hong, W., Pallen, C.J. "Prenylation-dependent Association of Protein-tyrosine Phosphatases PRL-1, -2, and -3 with the Plasma Membrane and the Early Endosome" J. Biol. Chem., 2000, 275, 21444-21452.
Zeng, Q., W. Hong, and Y.H. Tan. "Mouse PRL-2 and PRL-3, two potentially prenylated protein tyrosine phosphatases homologous to PRL-1" Biochem. Biophys. Res. Commun., 1998, 244, pp. 421-427.
Zhang., J. Somani, A.K. an dSiminovitch, K.A. "Roles of the SHP-1 tyrosine phosphatase in the negative regulation of cell signaling" Semin. Immunol, 1999, 12, pp. 361-378.
Zhang, Q., P.N. Raghunath, E. Vonderheid, N. Odum and M.A. Wasik. "Lack of phosphotyrosine phosphatase SHP-1 expression in malignant T-cell lymphoma cells results from methylation of the SHP-1 promoter" Am. J. Pathol., 2000, 157, pp. 1137-1146.
Zhang, Y.L., Keng, Y.F., Zhao, Y., Wu, L. and Zhang, Z.Y. "Suramin is an active site-directed, reversible, and tight-binding inhibitor of protein-tyrosine phosphateses" J. Biol. Chem., 1998, 273, pp. 12281-12287.
Zhang, Zhong-Yin. "Protein tyrosine phosphases: structure and function, substrate specificity, and inhibitor development" Ann. Rev. Pharmacol. Tex. Col., 2002, 42, pp. 209-235.
Zhang, Zhong-Yin. "Protein tyrosine phosphatases: prospects for therapeutics" Current Opinion in Chemical Biology, 2001, 5, pp. 416-423.
Zhao, Z., Shen, S.H. and Fischer, E.H. "Phorbol ester-induced expression, phosphorylation, and translocation of protein-tyrosine-phosphatase in 1C in HL-60 cells" Proc. Natl. Acad. Sci. USA, 1994, 91, pp. 5007-5011.
Dou, et al.: (IDrugs (2002), 5(8), 828-834) (Abstract).
Goldenberg: (Clinical Therapeutics (1999), 21(2), 309-319).
Sridhar, et al.: (The Lancet Oncology (2003), 4, 397-406).
Office Action in related co-pending U.S. Appl. No. 12/118,828 mailed Mar. 17, 2011.
Office Action in related co-pending U.S. Appl. No. 12/118,834 mailed Mar. 1, 2011.
Office Action in related co-pending U.S. Appl. No. 12/118,861 mailed Mar. 4, 2011.
Office Action in related co-pending U.S. Appl. No. 12/118,870 mailed Mar. 4, 2011.
Barnett, Stanley F., et al.: "The Akt/PKB Family of Protein Kinases: A Review of Small Molecule Inhibitors and Progress Towards Target Validation", Current Topics in Medicinal Chemistry, vol. 5, pp. 109-125, 2005.
Feun, Lynn G., et al.: "Phase I Study of Tricyclic Nucleoside Phosphate Using a Five-Day Continuous Infusion Schedule", Cancer Research, vol. 44, pp. 3608-3612, 1984.
Feun, Lynn G., et al.: "A Phase II Trial of Tricyclic Nucleoside Phosphate in Patients with Advanced Squamous Cell Carcinoma of the Cervix: A Gynecologic Oncology Group Study", American Journal of Clinical Oncology (Cancer Clinical Trials), vol. 16(6), pp. 506-508, 1993.
Hoffman, Karen, et al.: "Phase I-II Study: Triciribine (Tricyclic Nucleoside Phosphate) for Metastatic Breast Cancer", Cancer Chemotherapy and Pharmacology, vol. 37(3), pp. 254-258, 1996.
Mittelman, Abraham, et al.: "Phase I Study of Tricyclic Nucleoside Phosphate [1,2]", Cancer Treatment Reports, vol. 67(2), pp. 159-162, 1983.
O'Connell, Michael J., et al.: "Phase II Clinical Trial of Tricyclic Nucleoside Phosphate for Advanced Colorectal Cancer [1,2]", Cancer Treatment Reports, vol. 71(3), pp. 333-334,1987.
Schilcher, Rudolf B., et al.: "Phase I Evaluation and Clinical Pharmacology of Tricyclic Nucleoside 5'-Phosphate Using a Weekly Intravenous Regimen", Cancer Research, vol. 46, pp. 3147-3151, 1986.
Sun, Mei, et al.: "AKT1/PKBα Kinase is Frequently Elevated in Human Cancers and its Constitutive Activation is Required for Oncogenic Transformation in NIH3T3 Cells", American Journal of Pathology, vol. 159(2), pp. 431-437, 2001.
Yang, Lin, et al.: "Akt/Protein Kinase B Signaling Inhibitor-2, a Selective Small Molecule Inhibitor of Akt Signaling with Antitumor Activity in Cancer Cells Overexpressing Akt", Cancer Research, vol. 64, pp. 4394-4399, 2004.
Cheng, et al.: (Oncogene (1997), 14, 2793-2801).
Feun, et al.: (Cancer Research (1984), 44, 3608-3612).
Hoffman, et al.: (Cancer Chemother Pharmacol (1996), 37, 254-258).
Jetzt, et al.: (Cancer Research (2003), 63, 6697-6706).
Mittelman, et al.: (Cancer Treatment Reports (1983), 67(2), 159-162).
Schilcher, et al.: (Cancer Research (1986), 46, 3147-3151).
Shedden, et al.: (Pharmaceutical Research (2003), 20, 843-847).
Sun, et al.: (American Journal of Pathology (2001), 159(2), 431-437).
Japanese Office Action in the Japanese language in corresponding Japanese Patent Application No. 2007-506448.
Office Action in related co-pending U.S. Appl. No. 11/096,082 mailed Nov. 10, 2011.
Al-Janadi, Anas, et al.: "Activated Akt is Frequently Overexpressed in Human Breast Cancer Cells and Its Blockade Can Inhibit Growth," 2000 ASCO Annual Meeting, Proc Am Soc Clin Oncol, 19: 2000 (abstr 1879).
Office Action in related co-pending U.S. Appl. No. 12/118,828 mailed Nov. 23, 2011.
Office Action in related co-pending U.S. Appl. No. 12/118,834 mailed Nov. 23, 2011.
Office Action in related co-pending U.S. Appl. No. 12/118,861 mailed Nov. 23, 2011.
Office Action in related co-pending U.S. Appl. No. 12/118,870 mailed Nov. 23, 2011.
Porcari, Anthony R., et al.: "An Improved Total Synthesis of Triciribine: A Trycyclic Nucleoside with Antineoplastic and Antiviral Properties," Nucleosides, Nucleotides and Nucleic Acids, vol. 23(1-2), pp. 31-39, 2004.
Office Action in related co-pending U.S. Appl. No. 12/992,556 mailed Jan. 5, 2012.
Office Action in related co-pending U.S. Appl. No. 11/096,082 mailed Jun. 29, 2012.

(56) References Cited

OTHER PUBLICATIONS

Office Action in related co-pending U.S. Appl. No. 12/992,556 mailed Aug. 10, 2012.
Notice of Allowance in related co-pending U.S. Appl. No. 11/096,082 mailed Jan. 9, 2013.
Lu, C-H, et al.: "Preclinical Testing of Clinically Applicable Strategies for Overcoming Trastuzumab Resistance Caused by PTEN Deficiency," Clinical Cancer Research, vol. 13(19), pp. 5883-2888, 2007.
Yu, D., et al.: "Strategies for Overcoming Trastuzumab Resistance Caused by PTEN Deficiency," 99th AACR Annual Meeting, Apr. 12-16, 2008, San Diego CA.
Office Action dated Feb. 12, 2013 in co-pending Japanese Patent Application No. 2011-509454.
Non-Final Office Action in related co-pending U.S. Appl. No. 13/452,478 mailed Mar. 25, 2013.
Non-Final Office Action in related co-pending U.S. Appl. No. 13/453,778 mailed Mar. 8, 2013.
Non-Final Office Action from in related co-pending U.S. Appl. No. 13/453,807 mailed Feb. 26, 2013.
Non-Final Office Action in co-pending U.S. Appl. No. 13/453,834 mailed Aug. 5, 2013.
Notice of Allowance in co-pending U.S. Appl. No. 13/453,807 mailed Sep. 24, 2013.
Notice of Allowance from in co-pending U.S. Appl. No. 13/453,778 mailed Sep. 25, 2013.
Non-Final Office Action in co-pending U.S. Appl. No. 12/992,556 mailed Sep. 26, 2013.
Notice of Allowance in co-pending U.S. Appl. No. 13/452,478 mailed Nov. 7, 2013.
Notice of Allowance in U.S. Appl. No. 14/881,777 on Jun. 20, 2016.
Notice of Allowance in U.S. Appl. No. 14/832,417 on Jun. 29, 2016.
Notice of Allowance in U.S. Appl. No. 14/886,882 on Jun. 29, 2016.
Election/Restriction in U.S. Appl. No. 14/514,311 on Aug. 14, 2015.
Non-Final Office Action in U.S. Appl. No. 14/514,311 on Nov. 27, 2015.
Final Office Action in U.S. Appl. No. 14/514,311 on Feb. 4, 2016.
Non-Final Office Action in U.S. Appl. No. 14/789,347 on Feb. 25, 2016.
Non-Final Office Action in U.S. Appl. No. 14/800,286 on Mar. 9, 2016.
Non-Final Office Action in U.S. Appl. No. 14/832,417 on Mar. 1, 2016.
Non-Final Office Action in U.S. Appl. No. 14/881,777 on Feb. 25, 2016.
Non-Final Office Action in U.S. Appl. No. 14/886,882 on Feb. 26, 2016.
Decision of Refusal issued in Japanese Patent Application No. 2014-264781 on Apr. 26, 2016.
Notice of Allowance in U.S. Appl. No. 14/514,311, mailed Aug. 11, 2016.

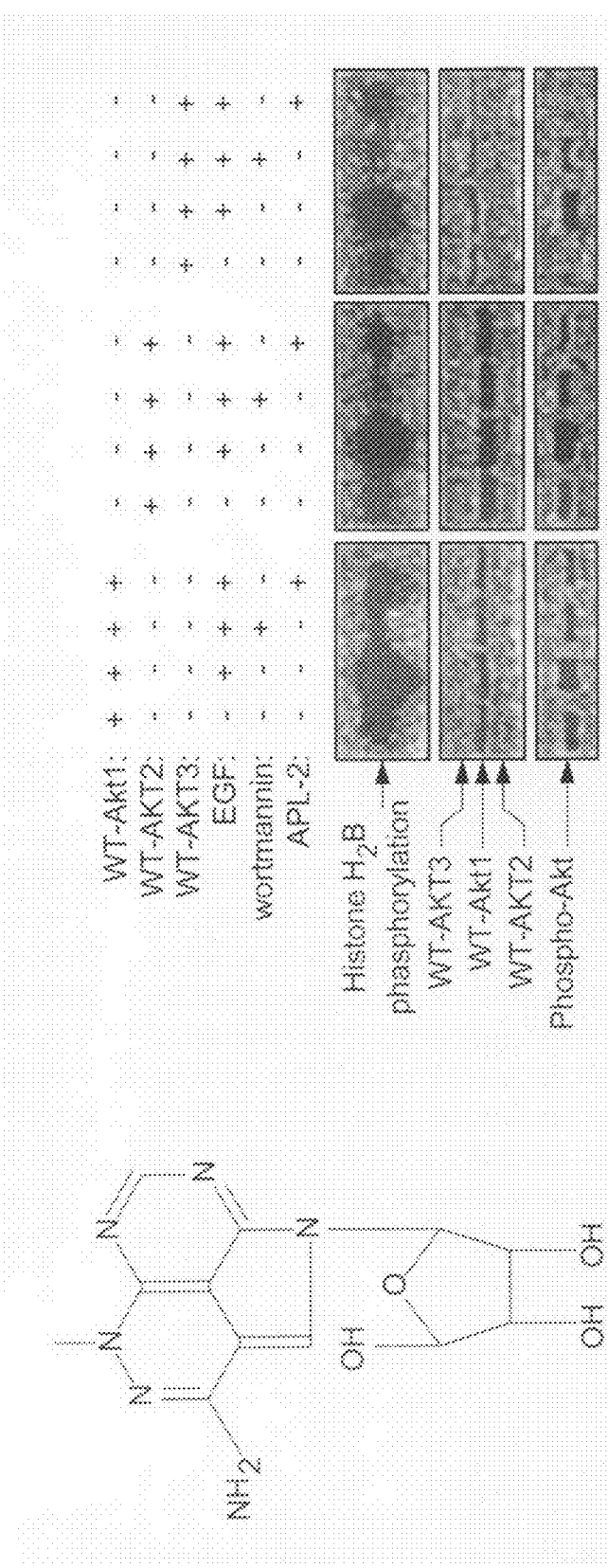
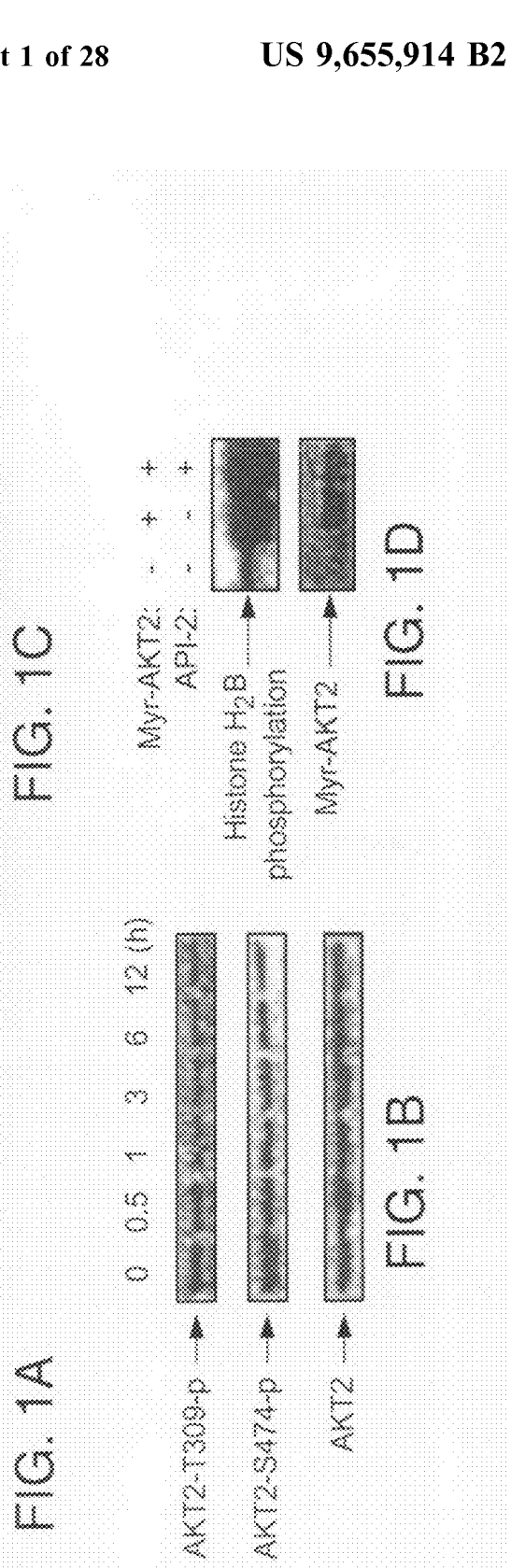

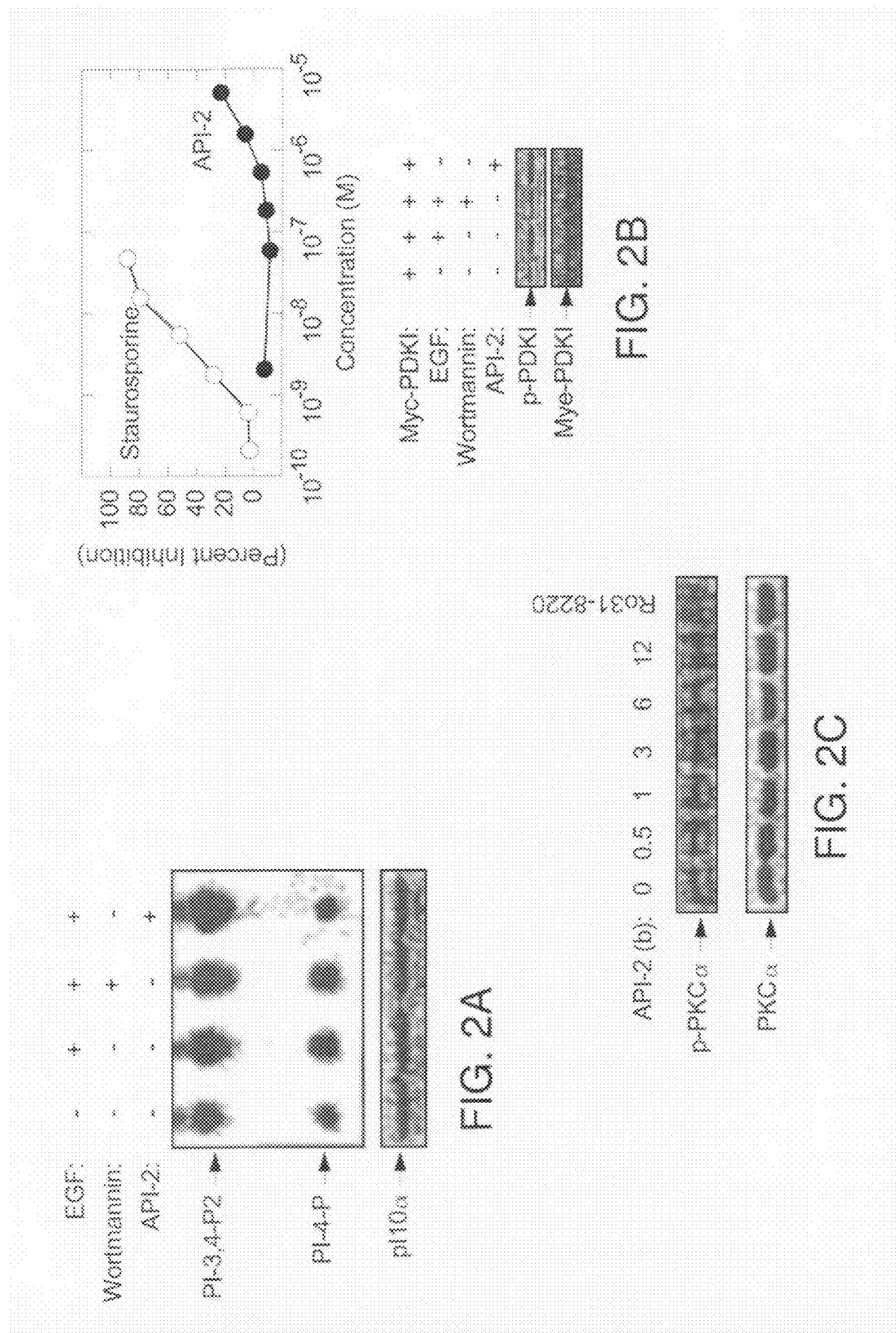

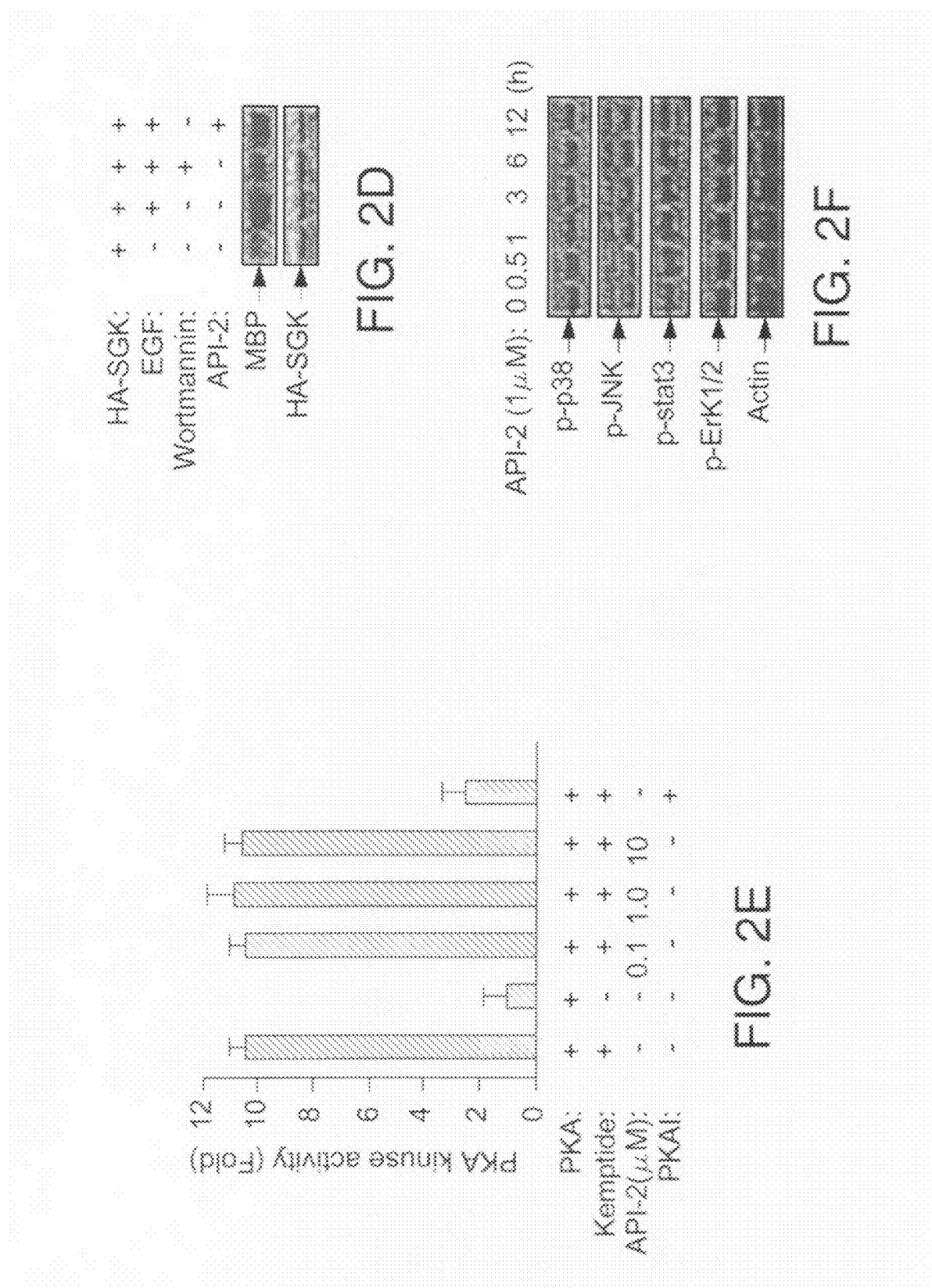

```
       atgaacgacgtagccattgtgaaggagggctggctgcacaaacgaggggaatatattaaa
    1  ------------+---------+---------+---------+---------+---------+  60
       tacttgctgcatcggtaacacttcctcccgaccgacgtgtttgctcccttatataattt a       M  N  D  V  A  I  V  K  E  G  W  L  H  K  R  G  E  Y  F  K  - acctggcggccacgctacttcctcctcaagaacgatggcacctttattggctacaaggaa
   61  ------------+---------+---------+---------+---------+---------+ 120
       tggaccgccggtgcgatgaaggaggagttcttgctaccgtggaaataaccgatgttcctt a       T  W  R  P  R  Y  F  L  L  K  N  D  G  T  F  I  G  Y  K  E  - cggcctcaggatgtggatcagcgagagtccccactcaacaacttctcagtggcacaatgc
  121  ------------+---------+---------+---------+---------+---------+ 180
       gccggagtcctacacctagtcgctctcaggggtgagttgttgaagagtcaccgtgttacg a       R  P  Q  D  V  D  Q  R  E  S  P  L  N  N  F  S  V  A  Q  C  -
                                                                PstI
                                                                 |
       cagctgatgaagacagagcggccaaggcccaacacctttatcatccgctgcctgcagtgg
  181  ------------+---------+---------+---------+---------+---------+ 240
       gtcgactacttctgtctcgccggttccgggttgtggaaatagtaggcgacggacgtcacc a       Q  L  M  K  T  E  R  P  R  P  N  T  F  I  I  R  C  L  Q  W  - accacagtcattgagcgcaccttccatgtagaaacgcctgaggagcgggaagaatgggcc
  241  ------------+---------+---------+---------+---------+---------+ 300
       tggtgtcagtaactcgcgtggaaggtacatctttgcggactcctcgcccttcttacccgg a       T  T  V  I  E  R  T  F  H  V  E  T  P  E  E  R  E  E  W  A  - accgccattcagactgtggccgatggactcaagaggcaggaagaagagacgatggacttc
  301  ------------+---------+---------+---------+---------+---------+ 360
       tggcggtaagtctgacaccggctacctgagttctccgtccttcttctctgctacctgaag a       T  A  I  Q  T  V  A  D  G  L  K  R  Q  E  E  E  T  M  D  F  - cgatcaggctcacccagtgacaactcaggggctgaagagatggaggtgtccctggccaag
  361  ------------+---------+---------+---------+---------+---------+ 420
       gctagtccgagtgggtcactgttgagtccccgacttctctacctccacagggaccggttc a       R  S  G  S  P  S  D  N  S  G  A  E  E  M  E  V  S  L  A  K  -
```

FIG. 6A

```
        cccaagcaccgtgtgaccatgaacgagtttgagtacctgaaactactgggcaagggcacc
    421 ------+---------+---------+---------+---------+---------+ 480
        gggttcgtggcacactggtacttgctcaaactcatggactttgatgacccgttcccgtgg a       P  K  H  R  V  T  M  N  E  F  E  Y  L  K  L  L  G  K  G  T  - tttggggaaagtgattctggtaaaagagaaggccacaggccgctactatgccatgaagatc
    481 ------+---------+---------+---------+---------+---------+ 540
        aaacccttttcactaagaccatttttctcttccggtgtccggcgatgatacggtacttctag a       F  G  K  V  I  L  V  K  E  K  A  T  G  R  Y  Y  A  M  K  I  - ctcaagaaggaggtcatcgtcgccaaggatgaggttgcccacacgcttactgaaaaccgt
    541 ------+---------+---------+---------+---------+---------+ 600
        gagttcttcctccagtagcagcggttcctactccaacgggtgtgcgaatgacttttggca a       L  K  K  E  V  I  V  A  K  D  E  V  A  H  T  L  T  E  N  R  -

PstI
                 |
        gtcctgcagaactctaggcatcccttccttacggccctcaagtactcattccagacccac
    601 ------+---------+---------+---------+---------+---------+ 660
        caggacgtcttgagatccgtagggaaggaatgccgggagttcatgagtaaggtctgggtg a       V  L  Q  N  S  R  H  P  F  L  T  A  L  K  Y  S  F  Q  T  H  -

XhoI
                                                            |
        gaccgcctctgctttgtcatggagtatgccaacgggggcgagctcttcttccacctgtct
    661 ------+---------+---------+---------+---------+---------+ 720
        ctggcggagacgaaacagtacctcatacggttgccccgctcgagaagaaggtggacaga a       D  R  L  C  F  V  M  E  Y  A  N  G  G  E  L  F  F  H  L  S  - cgagagcgcgtgttctccgaggaccgggcccgcttctatggtgcggagattgtgtctgcc
    721 ------+---------+---------+---------+---------+---------+ 780
        gctctcgcgcacaagaggctcctggcccgggcgaagataccacgcctctaacacagacgg a       R  E  R  V  F  S  E  D  R  A  R  F  Y  G  A  E  I  V  S  A  - ctggactacttgcactccgagaagaacgtggtgtaccgggacctgaagctagagaacctc
    781 ------+---------+---------+---------+---------+---------+ 840
        gacctgatgaacgtgaggctcttcttgcaccacatggccctggacttcgatctcttggag a       L  D  Y  L  H  S  E  K  N  V  V  Y  R  D  L  K  L  E  N  L  -
```

FIG. 6B

```
         atgctggacaaggacgggcacatcaagataacggacttcgggctgtgcaaggaggggatc
    841  ---------+---------+---------+---------+---------+---------+ 900
         tacgacctgttcctgcccgtgtagttctattgcctgaagcccgacacgttcctccctag a        M  L  D  K  D  G  H  I  K  I  T  D  F  G  L  C  K  E  G  I  - aaggatggtgccactatgaagacattctgcggaacgccggagtacctggcccctgaggtg
    901  ---------+---------+---------+---------+---------+---------+ 960
         ttcctaccacggtgatacttctgtaagacgccttgcggcctcatggaccggggactccac a        K  D  G  A  T  M  K  T  F  C  G  T  P  E  Y  L  A  P  E  V  - ctggaagacaacgactacggccgtgcagtggactggtgggggctgggcgtggtcatgtat
    961  ---------+---------+---------+---------+---------+---------+ 1020
         gaccttctgttgctgatgccggcacgtcacctgaccacccccgaccgcaccagtacata a        L  E  D  N  D  Y  G  R  A  V  D  W  W  G  L  G  V  V  M  Y  - gagatgatgtgtggccgcctgcccttctacaaccaggaccacgagaagctgttcgagctg
   1021  ---------+---------+---------+---------+---------+---------+ 1080
         ctctactacacaccggcggacgggaagatgttggtcctggtgctcttcgacaagctcgac a        E  M  M  C  G  R  L  P  F  Y  N  Q  D  H  E  K  L  F  E  L  - atcctcatggaggagatccgcttcccgcgcacactcggccctgaggccaagtccctgctc
   1081  ---------+---------+---------+---------+---------+---------+ 1140
         taggagtacctcctctaggcgaagggcgcgtgtgagccgggactccggttcagggacgag a        I  L  M  E  E  I  R  F  P  R  T  L  G  P  E  A  K  S  L  L  - tccgggctgctcaagaaggaccctacacagaggctcggtgggggctctgaggatgccaag
   1141  ---------+---------+---------+---------+---------+---------+ 1200
         aggcccgacgagttcttcctgggatgtgtctccgagccaccccgagactcctacggttc a        S  G  L  L  K  K  D  P  T  Q  R  L  G  G  G  S  E  D  A  K  - gagatcatgcagcaccggttctttgccaacatcgtgtggcaggatgtgtatgagaagaag
   1201  ---------+---------+---------+---------+---------+---------+ 1260
         ctctagtacgtcgtggccaagaaacggttgtagcacaccgtcctacacatactcttcttc a        E  I  M  Q  H  R  F  F  A  N  I  V  W  Q  D  V  Y  E  K  K  -
```

FIG. 6C

```
      ctgagcccacctttcaagccccaggtcacctctgagactgacaccaggtatttcgatgag
1261  ------------+----------+----------+----------+----------+----------+ 1320
      gactcgggtggaaagttcggggtccagtggagactctgactgtggtccataaagctactc a     L  S  P  P  F  K  P  Q  V  T  S  E  T  D  T  R  Y  F  D  E   - gagttcacagctcagatgatcaccatcacgccgcctgatcaagatgacagcatggagtgt
1321  ------------+----------+----------+----------+----------+----------+ 1380
      ctcaagtgtcgagtctactagtggtagtgcggcggactagttctactgtcgtacctcaca a     E  F  T  Q  Q  M  I  T  I  T  P  P  D  Q  D  D  S  M  E  C   - gtggacagtgagcggaggccgcacttcccccagttctcctactgacccagtggcacagcc
1381  ------------+----------+----------+----------+----------+----------+ 1440
      cacctgtcactcgcctccggcgtgaaggggtcaagaggatgagtcggtcaccgtgtcgg a     V  D  S  E  R  R  P  H  F  P  Q  F  S  Y  S  A  S  G  T  A   - tga
1441  --- 1443
      act a     *  -
```

FIG. 6D

```
            ATGAATGAGGTGTCTGTCATCAAAGAAGGCTGGCTCCACAAGCGTGGTGAATACATCAAG
    328  ---+---------+---------+---------+---------+---------+------  387
            TACTTACTCCACAGACAGTAGTTTCTTCCGACCGAGGTGTTCGCACCACTTATGTAGTTC a       M  N  E  V  S  V  I  K  E  G  W  L  H  K  R  G  E  Y  I  K    -

ACCTGGAGGCCACGGTACTTCCTGCTGAAGAGCGACGGCTCCTTCATTGGGTACAAGGAG
    388  ---+---------+---------+---------+---------+---------+------  447
            TGGACCTCCGGTGCCATGAAGGACGACTTCTCGCTGCCGAGGAAGTAACCCATGTTCCTC a       T  W  R  P  R  Y  F  L  L  K  S  D  G  S  F  I  G  Y  K  E    -

AGGCCCGAGGCCCCTGATCAGACTCTACCCCCCTTAAACAACTTCTCCGTAGCAGAATGC
    448  ---+---------+---------+---------+---------+---------+------  507
            TCCGGGCTCCGGGGACTAGTCTGAGATGGGGGGAATTTGTTGAAGAGGCATCGTCTTACG a       R  P  E  A  P  D  Q  T  L  P  P  L  N  N  F  S  V  A  E  C    -
                                                              PstI
                                                                |
            CAGCTGATGAAGACCGAGAGGCCGCGACCCAACACCTTTGTCATACGCTGCCTGCAGTGG
    508  ---+---------+---------+---------+---------+---------+------  567
            GTCGACTACTTCTGGCTCTCCGGCGCTGGGTTGTGGAAACAGTATGCGACGGACGTCACC a       Q  L  M  K  T  E  R  P  R  P  N  T  F  V  I  R  C  L  Q  W    -

ACCACAGTCATCGAGAGGACCTTCCACGTGGATTCTCCAGACGAGAGGGAGGAGTGGATG
    568  ---+---------+---------+---------+---------+---------+------  627
            TGGTGTCAGTAGCTCTCCTGGAAGGTGCACCTAAGAGGTCTGCTCTCCCTCCTCACCTAC a       T  T  V  I  E  R  T  F  H  V  D  S  P  D  E  R  E  E  W  M    -
                                                    ApaI
                                                      |
            CGGGCCATCCAGATGGTCGCCAACAGCCTCAAGCAGCGGGCCCCAGGCGAGGACCCCATG
    628  ---+---------+---------+---------+---------+---------+------  687
            GCCCGGTAGGTCTACCAGCGGTTGTCGGAGTTCGTCGCCCGGGGTCCGCTCCTGGGGTAC a       R  A  I  Q  M  V  A  N  S  L  K  Q  R  A  P  G  E  D  P  M    -

GACTACAAGTGTGGCTCCCCCAGTGACTCCTCCACGACTGAGGAGATGGAAGTGGCGGTC
    688  ---+---------+---------+---------+---------+---------+------  747
            CTGATGTTCACACCGAGGGGGTCACTGAGGAGGTGCTGACTCCTCTACCTTCACCGCCAG a       D  Y  K  C  G  S  P  S  D  S  S  T  T  E  E  M  E  V  A  V    -
```

FIG. 7A

```
        AGCAAGGCACGGGCTAAAGTGACCATGAATGACTTCGACTATCTCAAACTCCTTGGCAAG
    748 --+--------+---------+---------+---------+---------+------ 807
        TCGTTCCGTGCCCGATTTCACTGGTACTTACTGAAGCTGATAGAGTTTGAGGAACCGTTC a       S  K  A  R  A  K  V  T  M  N  D  F  D  Y  L  K  L  L  G  K  -

GGAACCTTTGGCAAAGTCATCCTGGTGCGGGAGAAGGCCACTGGCCGCTACTACGCCATG
    808 --+--------+---------+---------+---------+---------+------ 867
        CCTTGGAAACCGTTTCAGTAGGACCACGCCCTCTTCCGGTGACCGGCGATGATGCGGTAC a       G  T  F  G  K  V  I  L  V  R  E  K  A  T  G  R  Y  Y  A  M  -

AAGATCCTGCGAAAGGAAGTCATCATTGCCAAGGATGAAGTCGCTCACACAGTCACCGAG
    868 --+--------+---------+---------+---------+---------+------ 927
        TTCTAGGACGCTTTCCTTCAGTAGTAACGGTTCCTACTTCAGCGAGTGTGTCAGTGGCTC a       K  I  L  R  K  E  V  I  I  A  K  D  E  V  A  H  T  V  T  E  -

AGCCGGGTCCTCCAGAACACCAGGCACCCGTTCCTCACTGCGCTGAAGTATGCCTTCCAG
    928 --+--------+---------+---------+---------+---------+------ 987
        TCGGCCCAGGAGGTCTTGTGGTCCGTGGGCAAGGAGTGACGCGACTTCATACGGAAGGTC a       S  R  V  L  Q  N  T  R  H  P  F  L  T  A  L  K  Y  A  F  Q  -

ACCCACGACCGCCTGTGCTTTGTGATGGAGTATGCCAACGGGGGTGAGCTGTTCTTCCAC
    988 --+--------+---------+---------+---------+---------+------ 1047
        TGGGTGCTGGCGGACACGAAACACTACCTCATACGGTTGCCCCCACTCGACAAGAAGGTG a       T  H  D  R  L  C  F  V  M  E  Y  A  N  G  G  E  L  F  F  H  -

SmaI
        XmaI |                           ApaI
          |  |                            |
        CTGTCCCGGGAGCGTGTCTTCACAGAGGAGCGGGCCCGGTTTTATGGTGCAGAGATTGTC
   1048 --+--------+---------+---------+---------+---------+------ 1107
        GACAGGGCCCTCGCACAGAAGTGTCTCCTCGCCCGGGCCAAAATACCACGTCTCTAACAG a       L  S  R  E  R  V  F  T  E  E  R  A  R  F  Y  G  A  E  I  V  -

TCGGCTCTTGAGTACTTGCACTCGCGGGACGTGGTATACCGCGACATCAAGCTGGAAAAC
   1108 --+--------+---------+---------+---------+---------+------ 1167
        AGCCGAGAACTCATGAACGTGAGCGCCCTGCACCATATGGCGCTGTAGTTCGACCTTTTG a       S  A  L  E  Y  L  H  S  R  D  V  V  Y  R  D  I  K  L  E  N  -
```

FIG. 7B

```
             CTCATGCTGGACAAAGATGGCCACATCAAGATCACTGACTTTGGCCTCTGCAAAGAGGGC
    1168  --+---------+---------+---------+---------+---------+------  1227
             GAGTACGACCTGTTTCTACCGGTGTAGTTCTAGTGACTGAAACCGGAGACGTTTCTCCCG a     L   M   L   D   K   D   G   H   I   K   I   T   D   F   G   L   C   K   E   G   -

ATCAGTGACGGGGCCACCATGAAAACCTTCTGTGGGACCCCGGAGTACCTGGCGCCTGAG
    1228  --+---------+---------+---------+---------+---------+------  1287
             TAGTCACTGCCCCGGTGGTACTTTTGGAAGACACCCTGGGGCCTCATGGACCGCGGACTC a     I   S   D   G   A   T   M   K   T   F   C   G   T   P   E   Y   L   A   P   E   -

GTGCTGGAGGACAATGACTATGGCCGGGCCGTGGACTGGTGGGGGCTGGGTGTGGTCATG
    1288  --+---------+---------+---------+---------+---------+------  1347
             CACGACCTCCTGTTACTGATACCGGCCCGGCACCTGACCACCCCCGACCCACACCAGTAC a     V   L   E   D   N   D   Y   G   R   A   V   D   W   W   G   L   G   V   V   M   -

TACGAGATGATGTGCGGCCGCCTGCCCTTCTACAACCAGGACCACGAGCGCCTCTTCGAG
    1348  --+---------+---------+---------+---------+---------+------  1407
             ATGCTCTACTACACGCCGGCGGACGGGAAGATGTTGGTCCTGGTGCTCGCGGAGAAGCTC a     Y   E   M   M   C   G   R   L   P   F   Y   N   Q   D   H   E   R   L   F   E   -
        SacI
          |
             CTCATCCTCATGGAAGAGATCCGCTTCCCGCGCACGCTCAGCCCCGAGGCCAAGTCCCTG
    1408  --+---------+---------+---------+---------+---------+------  1467
             GAGTAGGAGTACCTTCTCTAGGCGAAGGGCGCGTGCGAGTCGGGGCTCCGGTTCAGGGAC a     L   I   L   M   E   E   I   R   F   P   R   T   L   S   P   E   A   K   S   L   -
                                                                      ApaI
                                                                        |
             CTTGCTGGGCTGCTTAAGAAGGACCCCAAGCAGAGGCTTGGTGGGGGCCCAGCGATGCC
    1468  --+---------+---------+---------+---------+---------+------  1527
             GAACGACCCGACGAATTCTTCCTGGGGTTCGTCTCCGAACCACCCCCGGGTCGCTACGG a     L   A   G   L   L   K   K   D   P   K   Q   R   L   G   G   G   P   S   D   A   -

AAGGAGGTCATGGAGCACAGGTTCTTCCTCAGCATCAACTGGCAGGACGTGGTCCAGAAG
    1528  --+---------+---------+---------+---------+---------+------  1587
             TTCCTCCAGTACCTCGTGTCCAAGAAGGAGTCGTAGTTGACCGTCCTGCACCAGGTCTTC a     K   E   V   M   E   H   R   F   F   L   S   I   N   W   Q   D   V   V   Q   K   -
```

FIG. 7C

```
                                         SalI
                                          |
        AAGCTCCTGCCACCCTTCAAACCTCAGGTCACGTCCGAGGTCGACACAAGGTACTTCGAT
1588    --+---------+---------+---------+---------+---------+------  1647
        TTCGAGGACGGTGGGAAGTTTGGAGTCCAGTGCAGGCTCCAGCTGTGTTCCATGAAGCTA a        K  L  L  P  P  F  K  P  Q  V  T  S  E  V  D  T  R  Y  F  D  -

GATGAATTTACCGCCCAGTCCATCACAATCACACCCCCTGACCGCTATGACAGCCTGGGC
1648    --+---------+---------+---------+---------+---------+------  1707
        CTACTTAAATGGCGGGTCAGGTAGTGTTAGTGTGGGGGACTGGCGATACTGTCGGACCCG a        D  E  F  T  A  Q  S  I  T  I  T  P  P  D  R  Y  D  S  L  G  -

TTACTGGAGCTGGACCAGCGGACCCACTTCCCCCAGTTCTCCTACTCGGCCAGCATCCGC
1708    --+---------+---------+---------+---------+---------+------  1767
        AATGACCTCGACCTGGTCGCCTGGGTGAAGGGGGTCAAGAGGATGAGCCGGTCGTAGGCG a        L  L  E  L  D  Q  R  T  H  F  P  Q  F  S  Y  S  A  S  I  R  -

GAGTGAGCAGTCTGCCCACGCAGAGGACGCACGCTCGCTGCCATCACCGCTGGGTGGTTT
1768    --+---------+---------+---------+---------+---------+------  1827
        CTCACTCGTCAGACGGGTGCGTCTCCTGCGTGCGAGCGACGGTAGTGGCGACCCACCAAA a        E  *  A  V  C  P  R  R  G  R  T  L  A  A  I  T  A  G  W  F  -

TTTACCCCTGCCCGG
1828    --+---------+--  1842
        AAATGGGGACGGGCC a        F  T  P  A  R  -
```

FIG. 7D

```
    gggctcagaggggagtcatcatgagcgatgttaccattgtgaaagaaggttgggttcaga
  1 ---------+---------+---------+---------+---------+---------+ 60
    cccgagtctccctcagtagtactcgctacaatggtaacactttcttccaacccaagtct
``` a     A   Q   R   G   V   I   M   S   D   V   T   I   V   K   E   G   W   V   Q   K -

```
     agaggggagaatatataaaaaactggaggccaagatacttccttttgaagacagatggct
  61 ---------+---------+---------+---------+---------+---------+ 120
     tctccctcttatatattttttgacctccggttctatgaaggaaaacttctgtctaccga
``` a     R   G   E   Y   I   K   N   W   R   P   R   Y   F   L   L   K   T   D   G   S -

```
      cattcataggatataaagagaaacctcaagatgtggatttaccttatcccctcaacaact
  121 ---------+---------+---------+---------+---------+---------+ 180
      gtaagtatcctatatttctctttggagttctacacctaaatggaatagggagttgttga
``` a     F   I   G   Y   K   E   K   P   Q   D   V   D   L   P   Y   P   L   N   N   F -

```
      tttcagtggcaaaatgccagttaatgaaaacagaacgaccaaagccaaacacatttataa
  181 ---------+---------+---------+---------+---------+---------+ 240
      aaagtcaccgttttacggtcaattactttgtcttgctggtttcggtttgtgtaaatatt
``` a     S   V   A   K   C   Q   L   M   K   T   E   R   P   K   P   N   T   F   I   I -

```
      tcagatgtctccagtggactactgttatagagagaacatttcatgtagatactccagagg
  241 ---------+---------+---------+---------+---------+---------+ 300
      agtctacagaggtcacctgatgacaatatctctcttgtaaagtacatctatgaggtctcc
``` a     R   C   L   Q   W   T   T   V   I   E   R   T   F   H   V   D   T   P   E   E -

PstI
                                                         |

```
      aaagggaagaatggacagaagctatccaggctgtagcagacagactgcagaggcaagaag
  301 ---------+---------+---------+---------+---------+---------+ 360
      tttcccttcttacctgtcttcgataggtccgacatcgtctgtctgacgtctccgttcttc
``` a     R   E   E   W   T   E   A   I   Q   A   V   A   D   R   L   Q   R   Q   E   E -

```
      aggagagaatgaattgtagtccaacttcacaaattgataatataggagaggaagagatgg
  361 ---------+---------+---------+---------+---------+---------+ 420
      tcctctcttacttaacatcaggttgaagtgtttaactattatatcctctccttctctacc
``` a     E   R   M   N   C   S   P   T   S   Q   I   D   N   I   G   E   E   E   M   D -

FIG. 8A

```
         atgcctctacaacccatcataaaagaaagacaatgaatgattttgactatttgaaactac
     421 ---------+---------+---------+---------+---------+---------+ 480
         tacggagatgttgggtagtattttctttctgttacttactaaaactgataaactttgatg a       A  S  T  T  H  H  K  R  *  T  M  N  D  F  D  Y  L  K  L  L  - taggtaaaggcacttttgggaaagttattttggttcgagagaaggcaagtggaaaatact
     481 ---------+---------+---------+---------+---------+---------+ 540
         atccatttccgtgaaaaccctttcaataaaaccaagctctcttccgttcacctttatga a       G  K  G  T  F  G  K  V  I  L  V  R  E  K  A  S  G  K  Y  Y  - atgctatgaagattctgaagaaagaagtcattattgcaaaggatgaagtggcacacactc
     541 ---------+---------+---------+---------+---------+---------+ 600
         tacgatacttctaagacttctttcttcagtaataacgtttcctacttcaccgtgtgtgag a       A  M  K  I  L  K  K  E  V  I  I  A  K  D  E  V  A  H  T  L  - taactgaaagcagagtattaaagaacactagacatccctttttaacatccttgaaatatt
     601 ---------+---------+---------+---------+---------+---------+ 660
         attgactttcgtctcataatttcttgtgatctgtagggaaaaattgtaggaactttataa a       T  E  S  R  V  L  K  N  T  R  H  P  F  L  T  S  L  K  Y  S  - ccttccagacaaaagaccgtttgtgttttgtgatggaatatgttaatgggggcgagctgt
     661 ---------+---------+---------+---------+---------+---------+ 720
         ggaaggtctgttttctggcaaacacaaaacactaccttatacaattaccccgctcgaca a       F  Q  T  K  D  R  L  C  F  V  M  E  Y  V  N  G  G  E  L  F  - ttttccatttgtcgagagagcgggtgttctctgaggaccgcacacgtttctatggtgcag
     721 ---------+---------+---------+---------+---------+---------+ 780
         aaaaggtaaacagctctctcgcccacaagagactcctggcgtgtgcaaagataccacgtc a       F  H  L  S  R  E  R  V  F  S  E  D  R  T  R  F  Y  G  A  E  - aaattgtctctgccttggactatctacattccggaaagattgtgtaccgtgatctcaagt
     781 ---------+---------+---------+---------+---------+---------+ 840
         tttaacagagacggaacctgatagatgtaaggcctttctaacacatggcactagagttca a       I  V  S  A  L  D  Y  L  H  S  G  K  I  V  Y  R  D  L  K  L  -
```

FIG. 8B

```
        tggagaatctaatgctggacaaagatggccacataaaaattacagattttggactttgca
   841 ---------+---------+---------+---------+---------+---------+ 900
        acctcttagattacgacctgtttctaccggtgtattttaatgtctaaaacctgaaacgt a    E  N  L  M  L  D  K  D  G  H  I  K  I  T  D  F  G  L  C  K - aagaagggatcacagatgcagccaccatgaagacattctgtggcactccagaatatctgg
   901 ---------+---------+---------+---------+---------+---------+ 960
        ttcttccctagtgtctacgtcggtggtacttctgtaagacaccgtgaggtcttatagacc a    E  G  I  T  D  A  A  T  M  K  T  F  C  G  T  P  E  Y  L  A - caccagaggtgttagaagataatgactatggccgagcagtagactggtggggcctagggg
   961 ---------+---------+---------+---------+---------+---------+ 1020
        gtggtctccacaatcttctattactgataccggctcgtcatctgaccaccccggatcccc a    P  E  V  L  E  D  N  D  Y  G  R  A  V  D  W  W  G  L  G  V - ttgtcatgtatgaaatgatgtgtgggaggttacctttctacaaccaggaccatgagaac
  1021 ---------+---------+---------+---------+---------+---------+ 1080
        aacagtacatactttactacacaccctccaatggaaagatgttggtcctggtactctttg a    V  M  Y  E  M  M  C  G  R  L  P  F  Y  N  Q  D  H  E  K  L - tttttgaattaatattaatggaagacattaaatttcctcgaacactctcttcagatgcaa
  1081 ---------+---------+---------+---------+---------+---------+ 1140
        aaaaacttaattataattaccttctgtaatttaaaggagcttgtgagagaagtctacgtt a    F  E  L  I  L  M  E  D  I  K  F  P  R  T  L  S  S  D  A  K -
                                    BamHI
                                     |
        aatcattgctttcagggctcttgataaaggatccaaataaacgccttggtggaggaccag
  1141 ---------+---------+---------+---------+---------+---------+ 1200
        ttagtaacgaaagtcccgagaactatttcctaggtttatttgcggaaccacctcctggtc a    S  L  L  S  G  L  L  I  K  D  P  N  K  R  L  G  G  P  D - atgatgcaaaagaaattatgagacacagtttcttctctggagtaaactggcaagatgtat
  1201 ---------+---------+---------+---------+---------+---------+ 1260
        tactacgttttctttaatactctgtgtcaaagaagagacctcatttgaccgttctacata a    D  A  K  E  I  M  R  H  S  F  F  S  G  V  N  W  Q  D  V  Y -
```

FIG. 8C

```
         HindIII
           |
      atgataaaaagcttgtacctccttttaaacctcaagtaacatctgagacagatactagat
1261  ---------+---------+---------+---------+---------+---------+ 1320
      tactattttcgaacatggaggaaaatttggagttcattgtagactctgtctatgatcta a        D  K  K  L  V  P  P  F  K  P  Q  V  T  S  E  T  D  T  R  Y - attttgatgaagaatttacagctcagactattacaataacaccacctgaaaaatatgatg
1321  ---------+---------+---------+---------+---------+---------+ 1380
      taaaactacttcttaaatgtcgagtctgataatgttattgtggtggacttttatactac a        F  D  E  E  F  T  A  Q  T  I  T  I  T  P  P  E  K  Y  D  E -

NotI
                                      |
      aggatggtatggactgcatggacaatgagaggcggccgcatttccctcaatttttcctact
1381  ---------+---------+---------+---------+---------+---------+ 1440
      tcctaccatacctgacgtacctgttactctccgccggcgtaaagggagttaaaaggatga a        D  G  M  D  C  M  D  N  E  R  R  P  H  F  P  Q  F  S  Y  S - ctgcaagtggacgagaataagtctctttcattctgctacttcactgtcatcttcaattta
1441  ---------+---------+---------+---------+---------+---------+ 1500
      gacgttcacctgctcttattcagagaaagtaagacgatgaagtgacagtagaagttaaat a        A  S  G  R  E  *  V  S  F  I  L  L  H  C  H  L  Q  F  I - ttactgaaaa
1501  ---------+ 1510
      aatgactttt a        T  E   -
```

FIG. 8D

| Drug | target | % growth inhibition in PTEN AS BT474.m1 cells | | | | | | Ttzm + drug significantly better than either alone? |
|---|---|---|---|---|---|---|---|---|
| | | Ttzm only | | drug only | | Ttzm + drug | | |
| Triciribine | Akt | 9.5 | +/-4.2 | 19.2 | +/-9.2 | 36.6 | +/-3.3 | yes (P<0.001) |
| KP 372-1 | Akt | 0 | +/-4.1 | 36 | +/-2.1 | 38.8 | +/-3.2 | no |
| 4ADPIB | Akt | 0.9 | +/-9.7 | 23.7 | +/-2.4 | 32.2 | +/-3.4 | no |
| Edelfosine | Akt | 2.2 | +/-9.6 | 41.8 | +/-1.2 | 51.9 | +/-2.3 | no |
| RAD001 | mTOR | 10.9 | +/-4.9 | 19.3 | +/-2.5 | 33.7 | +/-1.4 | yes (P<0.05) |
| QLT 0267 | ILK | 20 | +/-6.8 | 30.3 | +/-8.4 | 44.8 | +/-6.9 | yes (P<0.05) |

FIG. 9A

Figures 1, 3B:
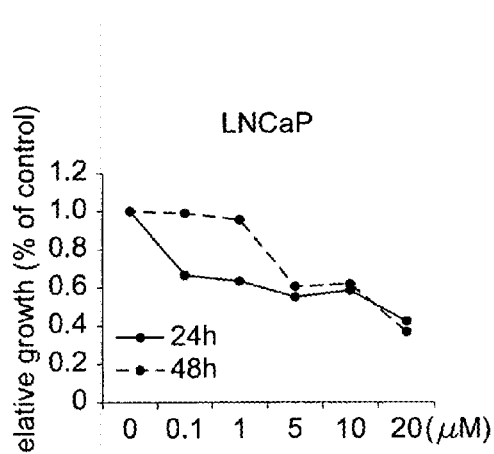
Figures 3, 3B, 4:
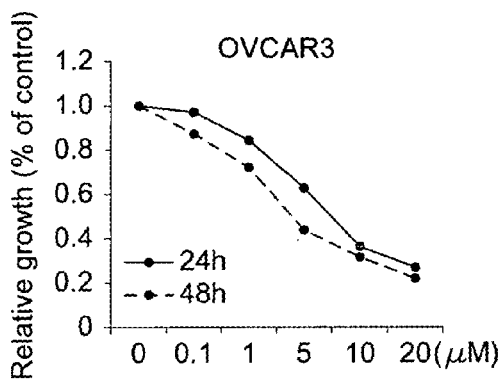
Figures 2, 3B:
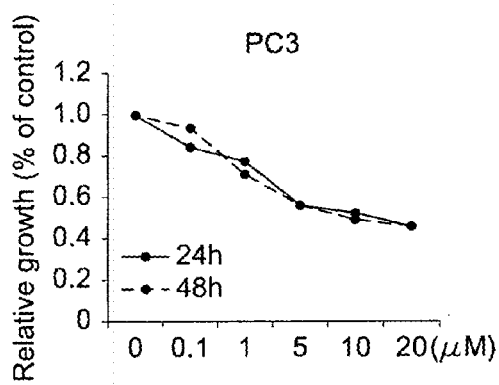
Figures 3, 3B, 4, 5:
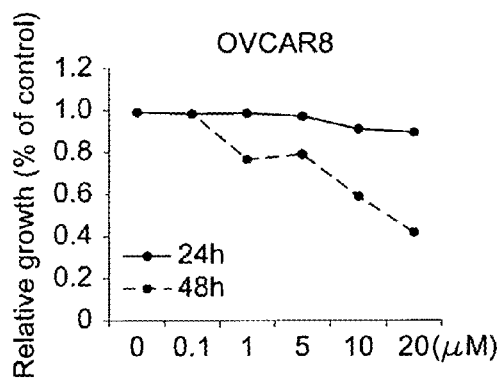
Figures 3, 3B:
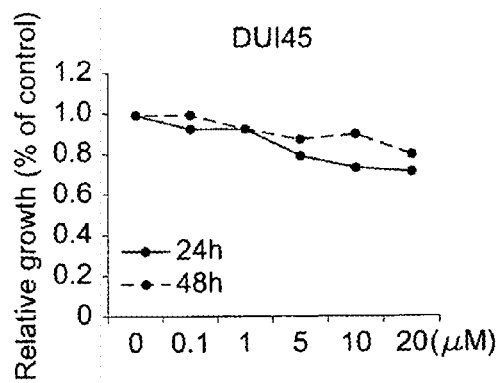
Figures 3, 3B, 4, 5, 6:
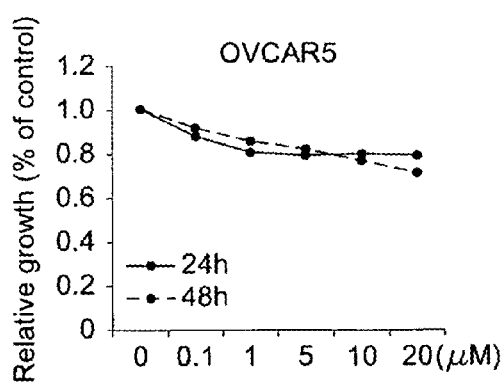
Figures 3, 3B, 4, 5, 6, 7:
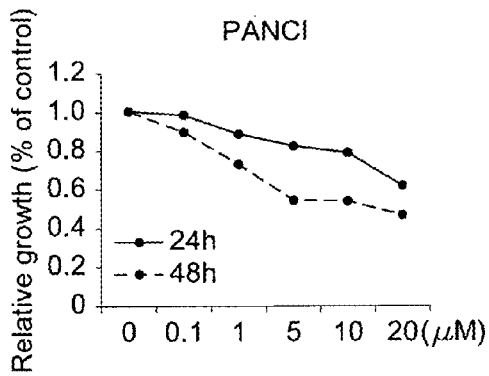
Figures 3, 3B, 4, 5, 6, 7, 8, 9:
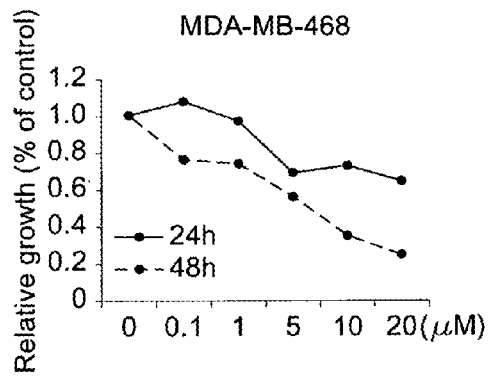
Figures 3, 3B, 4, 5, 6, 7, 8:
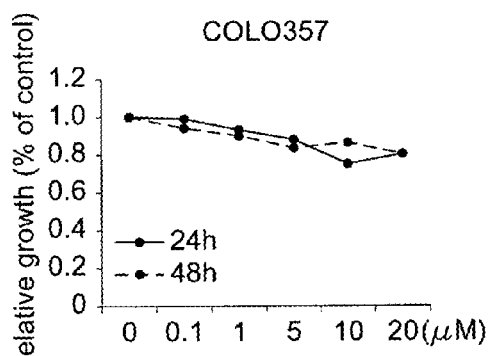

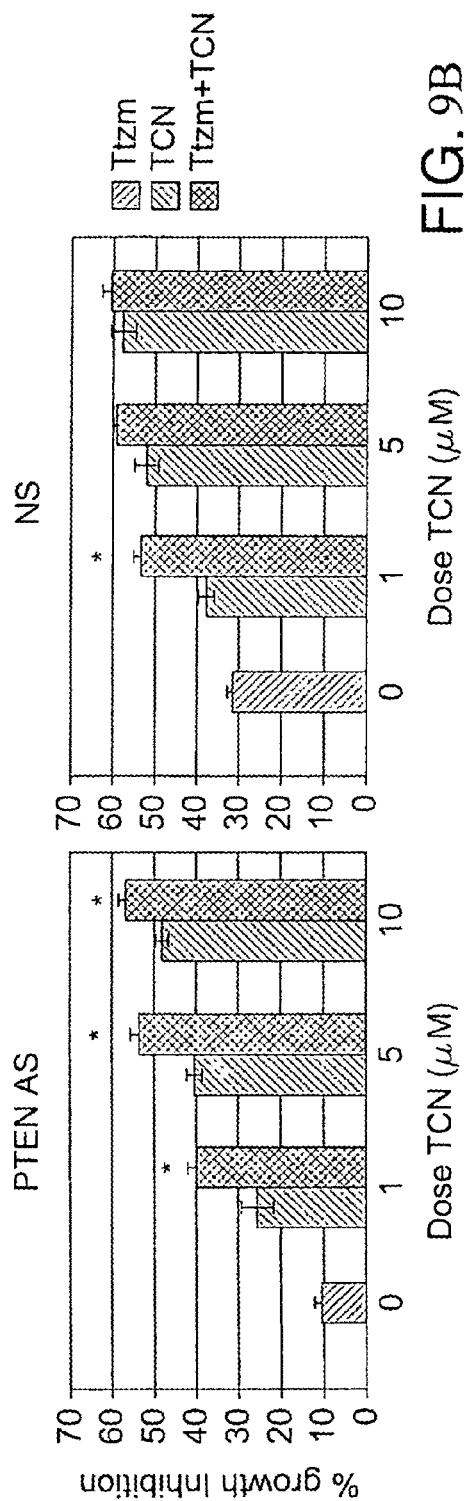
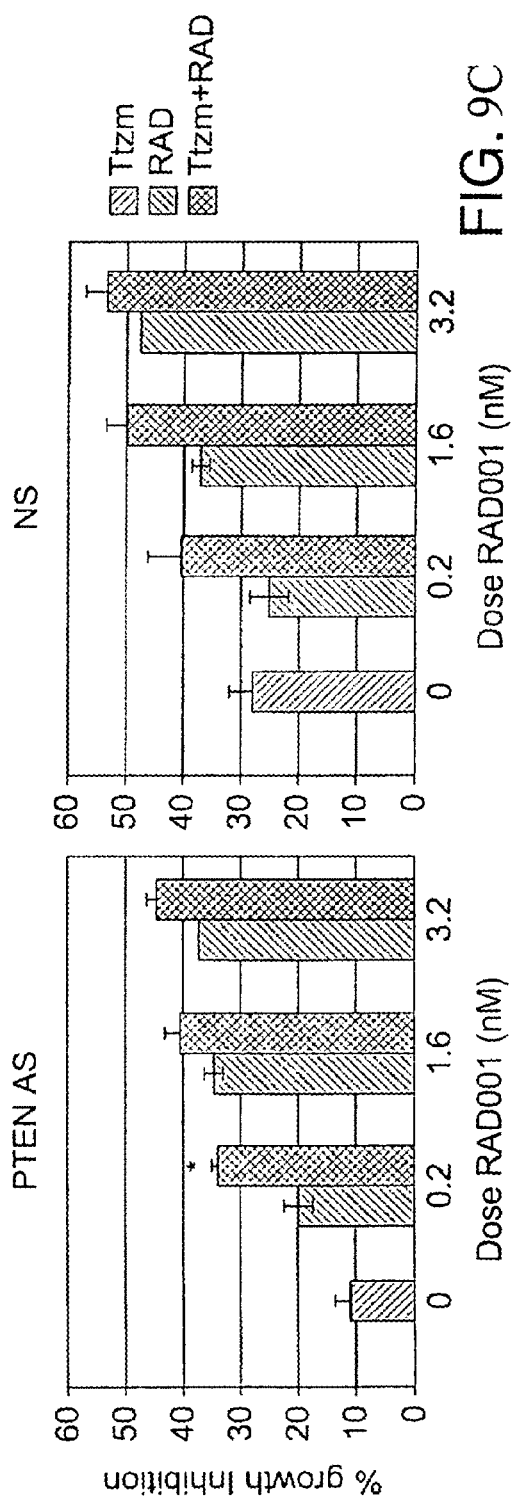
FIG. 9B
FIG. 9C

COMPOSITIONS INCLUDING TRICIRIBINE AND EPIDERMAL GROWTH FACTOR RECEPTOR INHIBITOR COMPOUNDS OR SALTS THEREOF AND METHODS OF USE THEREOF

The present application is a continuation of U.S. patent application Ser. No. 14/092,323, filed Nov. 27, 2013, which is a continuation of U.S. patent application Ser. No. 13/453,789, filed Apr. 23, 2012, which issued as U.S. Pat. No. 8,673,867, which is a continuation of U.S. patent application Ser. No. 12/118,861, filed May 12, 2008, which is abandoned, and is a continuation-in-part of U.S. patent application Ser. No. 11/096,082, filed Mar. 29, 2005, which issued as U.S. Pat. No. 8,435,959, which claims the benefit of U.S. provisional patent application No. 60/557,599, filed Mar. 29, 2004, each of which is incorporated herein by reference.

STATEMENT REGARDING FEDERALLY SPONSORED RESEARCH

This invention was made with government support CA077935 and CA089242 awarded by the National Cancer institute. The government has certain rights to the invention.

1. FIELD OF THE INVENTION

This application relates to combination therapies including triciribine compounds and epidermal growth factor receptor inhibitor compounds, particularly erlotinib-like compounds and compositions with reduced toxicity for the treatment and prevention of tumors, cancer, and other disorders associated with abnormal cell proliferation.

2. BACKGROUND OF THE INVENTION

Cancer is an abnormal growth of cells. Cancer cells rapidly reproduce despite restriction of space, nutrients shared by other cells, or signals sent from the body to stop reproduction. Cancer cells are often shaped differently from healthy cells, do not function properly, and can spread into many areas of the body. Abnormal growths of tissue, called tumors, are clusters of cells that are capable of growing and dividing uncontrollably. Tumors can be benign (noncancerous) or malignant (cancerous). Benign tumors tend to grow slowly and do not spread. Malignant tumors can grow rapidly, invade and destroy nearby normal tissues, and spread throughout the body.

Cancers are classified according to the kind of fluid or tissue from which they originate, or according to the location in the body where they first developed. In addition, some cancers are of mixed types. Cancers can be grouped into five broad categories, carcinomas, sarcomas, lymphomas, leukemias, and myelomas, which indicate the tissue and blood classifications of the cancer. Carcinomas are cancers found in body tissue known as epithelial tissue that covers or lines surfaces of organs, glands, or body structures. For example, a cancer of the lining of the stomach is called a carcinoma. Many carcinomas affect organs or glands that are involved with secretion, such as breasts that produce milk. Carcinomas account for approximately eighty to ninety percent of all cancer cases. Sarcomas are malignant tumors growing from connective tissues, such as cartilage, fat, muscle, tendons, and bones. The most common sarcoma, a tumor on the bone, usually occurs in young adults. Examples of sarcoma include osteosarcoma (bone) and chondrosarcoma (cartilage). Lymphoma refers to a cancer that originates in the nodes or glands of the lymphatic system, whose job it is to produce white blood cells and clean body fluids, or in organs such as the brain and breast. Lymphomas are classified into two categories: Hodgkin's lymphoma and non-Hodgkin's lymphoma. Leukemia, also known as blood cancer, is a cancer of the bone marrow that keeps the marrow from producing normal red and white blood cells and platelets. White blood cells are needed to resist infection. Red blood cells are needed to prevent anemia. Platelets keep the body from easily bruising and bleeding. Examples of leukemia include acute myelogenous leukemia, chronic myelogenous leukemia, acute lymphocytic leukemia, and chronic lymphocytic leukemia. The terms myelogenous and lymphocytic indicate the type of cells that are involved. Finally, myelomas grow in the plasma cells of bone marrow. In some cases, the myeloma cells collect in one bone and form a single tumor, called a plasmacytoma. However, in other cases, the myeloma cells collect in many bones, forming many bone tumors. This is called multiple myeloma.

Tumor induction and progression are often the result of accumulated changes in the tumor-cell genome. Such changes can include inactivation of cell growth inhibiting genes, or tumor suppressor genes, as well as activation of cell growth promoting genes, or oncogenes. Hundreds of activated cellular oncogenes have been identified to date in animal models, however, only a small minority of these genes have proven to be relevant to human cancers (Weinberg et al., *Oncogenes and the Molecular Origins of Cancer*, 1989. Cold Spring Harbor, N.Y.; Stanbridge J. et al., Cell, 1990. 63: p 867-874; Godwin et al., in *Gynecological oncology: principles and practice*, Hoskins W. J., Perez C. A. and Young R. C. (eds.), 1992. pp 87-116, Lippincott, Philadelphia). The activation of oncogenes in human cancers can result from factors such as increased gene copy number or structural changes. These factors can cause numerous cellular effects, for example, they can result in overexpression of a gene product. Several oncogenes involved in human cancer can be activated through gene overexpression.

It has become apparent that the successive genetic aberrations acquired by cancer cells result in defects in regulatory signal transduction circuits that govern normal cell proliferation, differentiation and programmed cell death (Hanahan, D. and Weinberg R. A., Cell, 2000. 100(1): p. 57-700). This in turn results in fundamental defects in cell physiology which dictate malignancy. These defects include: a) self sufficiency in growth signals (i.e. overexpression of growth factor receptor tyrosine kinases such as EGFR and aberrant activation of downstream signal transduction pathways such as Ras/Raf/Mek/Erk 1/2 and Ras/PI3K/Akt), b) resistance to anti-growth signals (i.e. lower expression of TGFβ and its receptor), c) evading apoptosis (i.e. loss of proapoptotic p53; overexpression of pro-survival Bcl-2; hyperactivation of survival pathways such as those mediated by PI3K/Akt), d) sustained angiogenesis (i.e. high levels of secretion of VEGF) and f) tissue invasion and metastasis (i.e. extracellular proteases and prometastatic integrins) (Hanahan, D. and Weinberg R. A., Cell, 2000. 100(1): p. 57-700).

Receptor tyrosine kinases such as EGFR, ErbB2, VEGFR and insulin-like growth factor 1 receptor (IGF-1R) are intimately involved in the development of many human cancers including colorectal pancreatic, breast and ovarian cancers (Khaleghpour K. et al., Carcinogenesis, 2004. 25(2): p. 241-8; Sekharam M. et al., Cancer Res, 2003. 63(22): p. 7708-16). Binding of ligands such as EGF, VEGF and IGF-1 to their receptors promotes stimulation of the intrinsic tyrosine kinase activity, autophosphorylation of specific tyrosines in the cytoplasmic domain of the receptors and recruitment of signaling proteins that trigger a variety of complex signal transduction pathways (Olayioye M. A. et al., Embo J, 2000. 19(13): p. 3159-67; Porter A. C. and Vaillancourt R. R., Oncogene, 1998. 17(11 Reviews): p. 1343-52). This in turn leads to the activation of many tumor survival and oncogenic pathways such as the Ras/Raf/Mek/Erk 1/2, JAK/STAT3 and PI3K/Akt pathways. Although all three pathways have been implicated in colon, pancreatic, breast and ovarian oncogenesis, those that are mediated by Akt have been shown to be critical in many steps of malignant transformation including cell proliferation, anti-apoptosis/survival, invasion and metastasis and angiogenesis (Datta S. R. et al., Genes Dev, 1999. 13(22): p. 2905-27).

Akt is a serine/threonine protein kinase (also known as PKB), which has 3 family members Akt1, Akt2 and Akt3. Stimulation of cells with growth or survival factors results in recruitment to the receptors of the lipid kinase phosphoinositide-3-OH-kinase (PI3K) which phosphorylates phosphoinositol-4,5-biphosphate ($PIP_2$) to $PIP_3$ which recruits Akt to the plasma membrane where it can be activated by phosphorylation on Thr308 and Ser473 (Akt1), Thr308 and Ser474 (Akt2) and Thr308 and Ser472 (Akt3) (Datta S. R. et al., Genes Dev, 1999. 13(22): p. 2905-27). Thus, PI3K activates Akt by phosphorylating PIP2 and converting to PIP3. The phosphatase PTEN dephosphorylates PIP3 to PIP2 and hence prevents the activation of Akt.

The majority of human cancers contain hyperactivated Akt (Datta S. R. et al., Genes Dev, 1999. 13(22): p. 2905-27; Bellacosa A. et al., Int J Cancer, 1995. 64(4): p. 280-5; Sun M. et al., Am J Pathol, 2001. 159(2): p. 431-7). In particular, Akt is overexpressed and/or hyperactivated in 57%, 32%, 27% and 36% of human colorectal, pancreatic, breast and ovarian cancers, respectively (Roy H. K. et al., Carcinogenesis, 2002. 23(1): p. 201-5; Altomare D. A. et al., J Cell Biochem, 2003. 88(1): p. 470-6; Sun M. et al., Cancer Res, 2001. 61(16): p. 5985-91; Stal O. et al., Breast Cancer Res, 2003. 5(2): p. R37-44; Cheng J. Q. et al., Proc Natl Acad Sci USA, 1992. 89(19): p. 9267-71; Yuan Z. Q. et al., Oncogene, 2000. 19(19): p. 2324-30). Hyperactivation of Akt is due to amplification and/or overexpression of Akt itself as well as genetic alterations upstream of Akt including overexpression of receptor tyrosine kinases and/or their ligands and deletion of the phosphatase PTEN (Khaleghpour K. et al., Carcinogenesis, 2004. 25(2): p. 241-8; Sekharam M. et al., Cancer Res, 2003. 63(22): p. 7708-16; Cohen B. D. et al., Biochem Soc Symp, 1998. 63: p. 199-210; Muller W. J. et al., Biochem Soc Symp, 1998. 63: p. 149-57; Miller W. E. et al., J Virol, 1995. 69(7): p. 4390-8; Slamon D. J. et al., Science, 1987. 235(4785): p. 177-82; Andrulis I. L. et al., J Clin Oncol, 1998. 16(4): p. 1340-9). Proof-of-concept of the involvement of Akt in oncogenesis has been demonstrated preclinically by showing that ectopic expression of Akt induces malignant transformation and promotes cell survival (Sun M. et al., Am J Pathol, 2001. 159(2): p. 431-7; Cheng J. Q. et al., Oncogene, 1997. 14(23): p. 2793-801) and that disruption of Akt pathways inhibits cell growth and induces apoptosis (Jetzt A. et al. Cancer Res, 2003. 63(20): p. 6697-706).

Current treatments of cancer and related diseases have limited effectiveness and numerous serious unintended side effects. Despite demonstrated clinical efficacy of many anti-cancer drugs, severe systemic toxicity often halts the clinical development of promising chemotherapeutic agents. Further, overexpression of receptor tyrosine kinases such as EGFR and their ligands such as IGF-1, Akt overexpression and/or loss of PTEN (all of which result in hyperactivation of Akt) are associated with poor prognosis, resistance to chemotherapy and shortened survival time of cancer patients. Current research strategies emphasize the search for effective therapeutic modes with less risk.

Thus, a combination therapy including a triciribine compound and erlotinib-like compound hold promise as a potential therapy for treating tumors, cancer, and abnormal cell proliferation while synergistically reducing toxicity or adverse side effects caused by currently administered cancer compounds.

3. SUMMARY OF THE INVENTION

The present invention provides novel therapeutic regimens of triciribine, triciribine phosphate and related compounds in combination with one or more erlotinib-like compounds to treat tumors or cancer in a subject while limiting systemic toxicity. The invention is based on the discovery that tumors or cancers, which overexpress Akt kinase are particularly sensitive to the cytotoxic effects of TCN and related compounds and a synergistic affect would arise with a combination of erlotinib-like compounds. The inventors have determined, contrary to the prior art and experience, how to successfully use triciribine and one or more erlotinib-like compounds to treat tumors and cancer by one or a combination of (i) administering triciribine and erlotinib-like compounds to patients who exhibit enhanced sensitivity to the triciribine compound and or the erlotinib-like compounds; (ii) use of a described dosage level that minimizes the toxicity of the triciribine compound and/or erlotinib-like compounds but yet still exhibits efficacy; or (iii) use of a described dosage regimen that minimizes the toxicity of the the triciribine compound and/or erlotinib-like compounds.

In one aspect of the present invention, the invention encompasses a composition including:

(i) a compound of Formula I-IV:

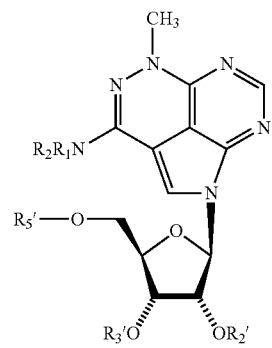

Formula I

-continued

Formula II
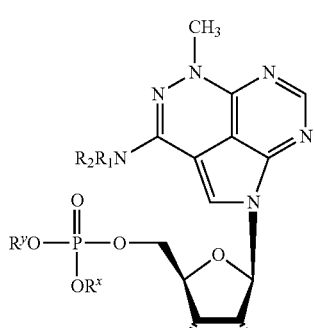

Formula III
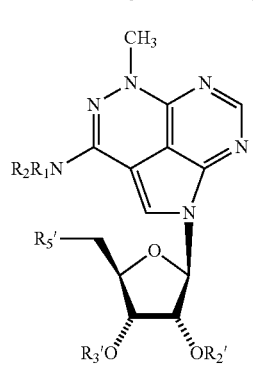

Formula IV
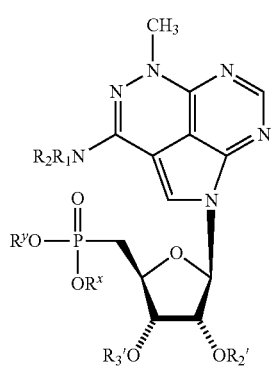

wherein each R2', R3' and R5' are independently hydrogen, optionally substituted phosphate or phosphonate (including mono-, di-, or triphosphate or a stabilized phosphate prodrug); acyl (including lower acyl); alkyl (including lower alkyl); amide, sulfonate ester including alkyl or arylalkyl; sulfonyl, including methanesulfonyl and benzyl, wherein the phenyl group is optionally substituted with one or more substituents as for example as described in the definition of an aryl given herein; optionally substituted arylsulfonyl; a lipid, including a phospholipid; an amino acid; a carbohydrate; a peptide; or cholesterol; or other pharmaceutically acceptable leaving group that, in vivo, provides a compound wherein R2', R3' or R5' is independently H or mono-, di- or tri-phosphate;

wherein Rx and Ry are independently hydrogen, optionally substituted phosphate; acyl (including lower acyl); amide, alkyl (including lower alkyl); aromatic, polyoxyalkylene such as polyethyleneglycol, optionally substituted arylsulfonyl; a lipid, including a phospholipid; an amino acid; a carbohydrate; a peptide; or cholesterol; or other pharmaceutically acceptable leaving group. In one embodiment, the compound is administered as a 5'-phosphoether lipid or a 5'-ether lipid.

R1 and R2 each are independently H, optionally substituted straight chained, branched or cyclic alkyl (including lower alkyl), alkenyl, or alkynyl, CO-alkyl, CO-alkenyl, CO-alkynyl, CO-aryl or heteroaryl, CO-alkoxyalkyl, CO-aryloxyalkyl, CO-substituted aryl, sulfonyl, alkylsulfonyl, arylsulfonyl, aralkylsulfonyl;

(ii) erlotinib-like compounds as in formula V:

Formula V
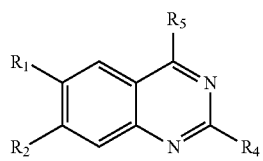

wherein each R1 and R2 is independently hydrogen, independently optionally substituted alkoxy, optionally substituted amine, aromatic amine, heteroaromatic amine, optionally substituted straight chained, branched or cyclic alkyl;

each R3 and R4 is independently hydrogen, independently optionally substituted aromatic amine, heteroaromatic amine, or cyclic amine; and (iii) a pharmaceutically acceptable carrier.

In another embodiment, the invention encompasses a method of treating a tumor or cancer in a mammal including administering to the mammal an effective amount of a composition including:

(i) a compound of formula I-IV:

Formula I
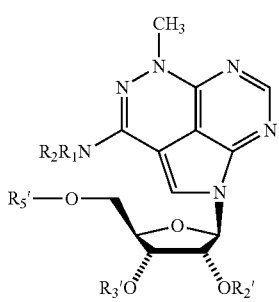

Formula II
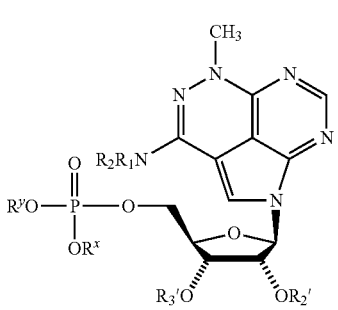

-continued

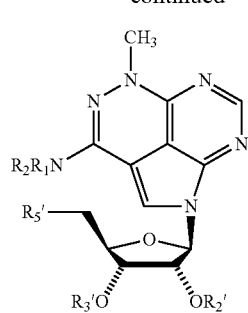

Formula III

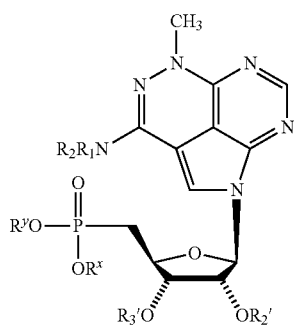

Formula IV wherein each R2', R3' and R5' are independently hydrogen, optionally substituted phosphate or phosphonate (including mono-, di-, or triphosphate or a stabilized phosphate prodrug); acyl (including lower acyl); alkyl (including lower alkyl); amide, sulfonate ester including alkyl or arylalkyl; sulfonyl, including methanesulfonyl and benzyl, wherein the phenyl group is optionally substituted with one or more substituents as for example as described in the definition of an aryl given herein; optionally substituted arylsulfonyl; a lipid, including a phospholipid; an amino acid; a carbohydrate; a peptide; or cholesterol; or other pharmaceutically acceptable leaving group that, in vivo, provides a compound wherein R2', R3' or R5' is independently H or mono-, di- or tri-phosphate;

wherein Rx and Ry are independently hydrogen, optionally substituted phosphate; acyl (including lower acyl); amide, alkyl (including lower alkyl); aromatic, polyoxyalkylene such as polyethyleneglycol, optionally substituted arylsulfonyl; a lipid, including a phospholipid; an amino acid; a carbohydrate; a peptide; or cholesterol; or other pharmaceutically acceptable leaving group. In one embodiment, the compound is administered as a 5'-phosphoether lipid or a 5'-ether lipid.

R1 and R2 each are independently H, optionally substituted straight chained, branched or cyclic alkyl (including lower alkyl), alkenyl, or alkynyl, CO-alkyl, CO-alkenyl, CO-alkynyl, CO-aryl or heteroaryl, CO-alkoxyalkyl, CO-aryloxyalkyl, CO-substituted aryl, sulfonyl, alkylsulfonyl, arylsulfonyl, aralkylsulfonyl; and (ii) erlotinib-like compounds as in formula V:

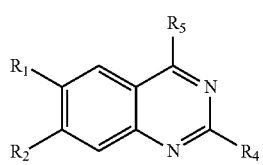

Formula V wherein each R1 and R2 is independently hydrogen, independently optionally substituted alkoxy, optionally substituted amine, aromatic amine, heteroaromatic amine, optionally substituted straight chained, branched or cyclic alkyl;

each R3 and R4 is independently hydrogen, independently optionally substituted aromatic amine, heteroaromatic amine, or cyclic amine.

Methods are useful to treat tumors and cancers that are particularly susceptible to the toxic effects of TCN, TCN-P and/or related compounds. In another embodiment, methods are provided for treating a tumor in a mammal, particularly a human that includes (i) obtaining a biological sample from the tumor; (ii) determining whether the tumor overexpresses an Akt kinase, and (iii) treating the tumor that overexpresses Akt kinase with triciribine, triciribine phosphate or a related compound in combination with one or more erlotinib-like compounds, as described herein. In another embodiment, the level of Akt kinase expression can be determined by assaying the tumor or cancer for the presence of a phosphorylated Akt kinase, for example, by using an antibody that can detect the phosphorylated form. In another embodiment, the level of Akt expression can be determined by assaying a tumor or cancer cells obtained from a subject and comparing the levels to a control tissue. In certain embodiments, the Akt can be overexpressed at least 2, 2.5, 3 or 5 fold in the cancer sample compared to the control. In certain embodiments, the overexpressed Akt kinase can be a hyperactivated and phosphorylated Akt kinase.

In another aspect of the present invention, dosing regimens are provided that limit the toxic side effects of TCN and related compounds. In another embodiment, such dosing regimens minimize or eliminate toxic side effects, including, but not limited to, hepatoxicity, thrombocytopenia, hyperglycemia, vomiting, hypocalcemia, anemia, hypoalbunemia, myelosuppression, hypertriglyceridemia, hyperamylasemia, diarrhea, stomachitis and/or fever. In another embodiment, the administration of TCN, TCN-P or related compounds provides at least a partial, such as at least 15, 20 or 30%, or complete response in vivo in at least 15, 20, or 25% of the subjects.

In another embodiment, a method is provided to treat a subject who has been diagnosed with a tumor by administering to the subject an effective amount of TCN, TCN-P or a related compound and one or more erlotinib-like compounds according to a dosing schedule that includes administering the the triciribine compound and erlotinib-like compounds approximately one time per week for approximately three weeks followed by a one week period wherein the triciribine compound and erlotinib-like compounds are not administered. In another embodiment, methods are provided to treat tumor or cancer in a subject by administering to the subject a dosing regimen of 10 mg/m2 or less of TCN, TCN-P or a related compound and one or more erlotinib-like compounds each one time per week. In another embodiment, the triciribine compound and one or more erlotinib-like compounds can be administered as a single bolus dose over a short period of time, for example, about 5, 10 or 15 minutes. In further embodiments, dosing schedules are provided in which the triciribine compound and one or more erlotinib-like compounds are administered via continuous infusion for at least 24, 48, 72, 96, or 120 hours. In certain embodiments, the continuous administration can be repeated at least once a week, once every two weeks and/or once a month. In other embodiments, the triciribine compound and one or more erlotinib-like compounds can be administered at least once every three weeks. In further embodiments, the compounds can be administered at least once a day for at least 2, 3, 4 or 5 days.

In further embodiments, the triciribine compound and one or more erlotinib-like compounds as disclosed herein can be administered to patients in an amount that is effective in causing tumor regression. The administration the triciribine compound and one or more erlotinib-like compounds can provide at least a partial, such as at least 15, 20 or 30%, or complete response in vivo in at least 15-20% of the subjects. In certain embodiments, at least 2, 5, 10, 15, 20, 30 or 50 mg/m2 of the triciribine compound and at least about 10, 25, 50, 75, 100, 150, 200, 250 or 500 mg one or more erlotinib-like compounds disclosed herein can be administered to a subject. The administration of the triciribine compound and one or more erlotinib-like compounds can be conducted according to any of the therapeutic regimens disclosed herein. In particular embodiments, the dosing regimen can include administering less than 20 mg/m2 of the triciribine compound and one or more erlotinib-like compounds. In one embodiment, less than 10 mg/m2 of the triciribine compound and less than about 200 mg of one or more erlotinib-like compounds can be administered once a week. In further embodiments, dosages of or less than 2 mg/m2, 5 mg/m2, 10 mg/m2, and/or 15 mg/m2 of the triciribine compound and 10 mg, 20 mg, 50 mg, 100 mg, 150 mg, 200 mg, 250 mg, or 500 mg of one or more erlotinib-like compounds can be administered to a subject. In another embodiment, less than 10 mg/m2 of the triciribine compound and less than 150 mg of the erlotinib compound can be administered to a subject via continuous infusion for at least five days. In particular embodiments, the triciribine compound and one or more erlotinib-like compounds as disclosed herein can be used for the treatment of pancreatic, prostate, colo-rectal and/or ovarian cancer.

In another embodiment, the triciribine compound and one or more erlotinib-like compounds and/or therapeutic regimens of the present invention can be used to prevent and/or treat a carcinoma, sarcoma, lymphoma, leukemia, and/or myeloma. In other embodiments of the invention, the triciribine compound and one or more erlotinib-like compounds can be used to treat solid tumors. In still further embodiments, the triciribine compound and one or more erlotinib-like compounds and compositions disclosed herein can be used for the treatment of a tumor or cancer, such as, but not limited to cancer of the following organs or tissues: breast, prostate, bone, lung, colon, including, but not limited to colorectal, urinary, bladder, non-Hodgkin lymphoma, melanoma, kidney, renal, pancreas, pharnx, thyroid, stomach, brain, and/or ovaries. In a particular embodiment, the triciribine compound and one or more erlotinib-like compounds can be used for the treatment of pancreatic, breast, colorectal and/or ovarian cancer. In further embodiments of the present invention, the triciribine compound and one or more erlotinib-like compounds disclosed herein can be used in the treatment of angiogenesis-related diseases. In certain embodiments, methods are provided to treat leukemia via continuous infusion of, the triciribine compound and one or more erlotinib-like compounds via continuous infusion for at least 24, 48, 72 or 96 hours. In other embodiments, the continuous infusion can be repeated, for example, at least once every two, three or four weeks.

In a particular embodiment, there is provided a method for the treatment of tumors, cancer, and others disorders associated with an abnormal cell proliferation in a host, the method includes administering to the host an effect amount of the triciribine compound and one or more erlotinib-like compounds optionally in combination with a pharmaceutically acceptable carrier.

In one aspect, the triciribine compound and one or more erlotinib-like compounds and compositions can be administered in combination and can form part of the same composition, or be provided as a separate composition for administration at the same time or a different time.

In other embodiments, the triciribine compound and one or more Erlotinib-like compounds as disclosed herein can be used to treat tumors or cancers resistant to one or more known anti-cancer drugs, including the embodiments of tumors or cancers and compounds disclosed herein. In one embodiment, the triciribine compound and one or more erlotinib-like compounds as disclosed herein is administered in an effective amount for the treatment of a patient with a drug resistant tumor or cancer, for example, multidrug resistant tumors or cancer including, but not limited to, those resistant to taxol alone, rapamycin, tamoxifen, cisplatin, and/or gefitinib (iressa).

In certain embodiments, a method is provided including administering to a host in need thereof an effective amount of a triciribine compound and one or more erlotinib-like compounds disclosed herein, or pharmaceutical composition including a triciribine compound and one or more erlotinib-like compounds, in an effective amount for the treatment of the treatment of tumors, cancer, and others disorders associated with an abnormal cell proliferation in a host.

In another embodiment, a method for the treatment of a tumor or cancer is provided including an effective amount of a compound disclosed herein, or a salt, isomer, prodrug or ester thereof, to an individual in need thereof, wherein the cancer is for example, carcinoma, sarcoma, lymphoma, leukemia, or myeloma. The compound, or salt, isomer, prodrug or ester thereof, is optionally provided in a pharmaceutically acceptable composition including the appropriate carriers, such as water, which is formulated for the desired route of administration to an individual in need thereof. Optionally the compound is administered in combination or alternation with at least one additional therapeutic agent for the treatment of tumors or cancer.

Also within the scope of the invention is the use of a compound disclosed herein or a salt, prodrug or ester thereof in the treatment of a tumor or cancer, optionally in a pharmaceutically acceptable carrier; and the use of a triciribine compound and one or more erlotinib-like compounds disclosed herein or a salt, prodrug or ester thereof in the manufacture of a medicament for the treatment of cancer or tumor, optionally in a pharmaceutically acceptable carrier.

4. BRIEF DESCRIPTION OF THE DRAWINGS

FIG. 1A-FIG. 1D demonstrates the identification of API-2 (triciribine) as a candidate of Akt inhibitor from the NCI Diversity Set. FIG. 1A illustrates the chemical structure of API-2 (triciribine). FIG. 1B demonstrates that API-2 inhibits phosphorylation levels of AKT2 in AKT2-transformed NIH3T3 cells. Wile type AKT2-transformed NIH3T3 cells were treated with API-2 (1 µM) for indicated times and subjected to immunoblotting analysis with anti-phospho-Akt-T308 and -S473 antibodies (top and middle panels). The bottom panel shows expression of total AKT2. In FIG. 1C, it is shown that API-2 inhibits three isoforms of Akt. HEK293 cells were transfected with HA-Akt1, -AKT2 and -AKT3 and treated with API-2 (1 µM) or wortmannin (15 µM) prior to EGF stimulation, the cells were lysed and immunoprecipitated with anti-HA antibody. The immunoprecipitates were subjected to in vitro kinase assay (top) and immunoblotting analysis with anti-phospho-Akt-T308 (bottom) antibody. Middle panel shows expression of transfected Akt1, AKT2 and AKT3. FIG. 1D illustrates that API-2 did not inhibit Akt in vitro. In vitro kinase assay of constitutively active AKT2 recombinant protein in a kinase buffer containing 1 µM API-2 (lane 3).

FIG. 2A-FIG. 2F demonstrates that API-2 does not inhibit PI3K, PDK1 and the closely related members of AGC kinase family. FIG. 2A demonstrates an in vitro PI3K kinase assay. HEK293 cells were serum-starved and treated with API-2 (1 µM) or Wortmannin (15 µM) for 30 minutes prior to EGF stimulation. Cells were lysed and immunoprecipitated with anti-p110α antibody. The immunoprecipitates were subjected to in vitro kinase assay using PI-4-P as substrate. FIG. 2B illustrates the effect of API-2 on in vitro PDK1 activation (top panel), closed circles show inhibition by API-2. Open circles show inhibition by the positive control staurosporine, which is a potent PDK1 inhibitor (IC50=5 nM). Bottom panels are immunoblotting analysis of HEK293 cells that were transfected with Myc-PDK1 and treated with wortmannin or API-2 prior to EGF stimulation. The immunoblots were detected with indicated antibodies. FIG. 2C illustrates an immunoblot analysis of phosphorylation levels of PKC☐with anti-phospho-PKCα☐T638 (top) and total PKCα (bottom) antibodies following treatment with API-2 or a nonselective PKC inhibitor Ro31-8220. FIG. 2D shows an in vitro SGK kinase assay. HEK293 cells were transfected with HA-SGK and treated with API-2 or wortmannin prior to EGF stimulation. In vitro kinase was performed with HA-SGK immunoprecipitates using MBP as substrate (top). Bottom panel shows the expression of transfected HA-SGK. FIG. 2E illustrates the results of a PKA kinase assay. Immuno-purified PKA was incubated in ADB buffer (Upstate Biotechnology Inc) containing indicated inhibitors (API-2 or PKAI) and substrate Kemptide. The kinase activity was quantified. In FIG. 2F, a western blot is shown. OVCAR3 cells were treated with API-2 for indicated times. Cell lysates were immunoblotted with indicated anti-phospho-antibodies (panels 1-4) and anti-actin antibody (bottom).

Figures 3, 3B, 4, 5, 6, 7, 8, 9, 10:
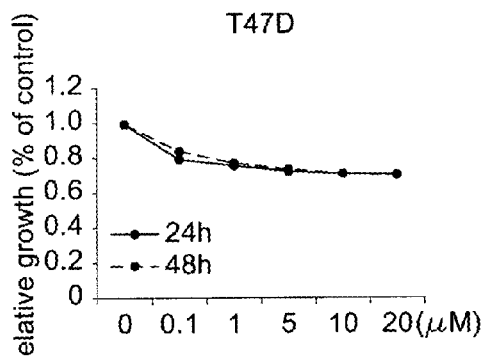
Figures 3, 3B, 4, 5, 6, 7, 8, 9, 10, 11:
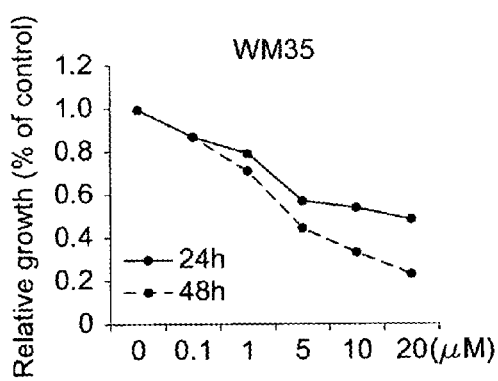
Figures 3, 3B, 4, 5, 6, 7, 8, 9, 10, 11, 12:
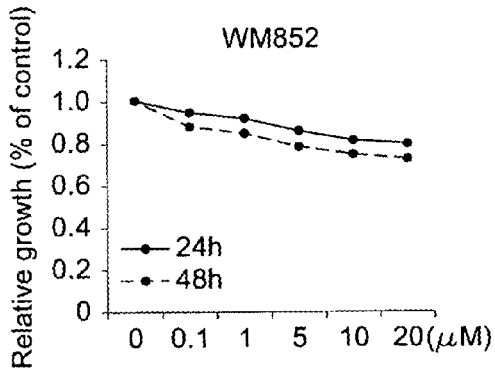
Figures 1, 3C:
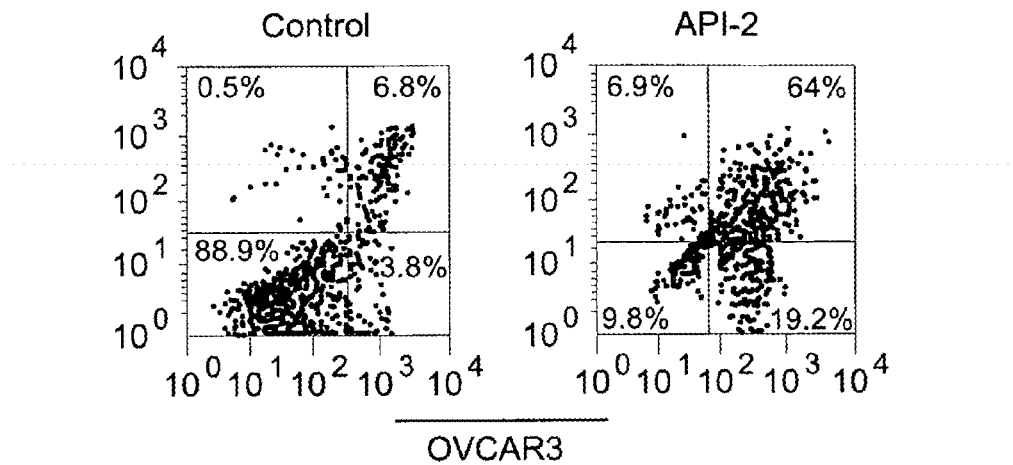
Figures 2, 3C:
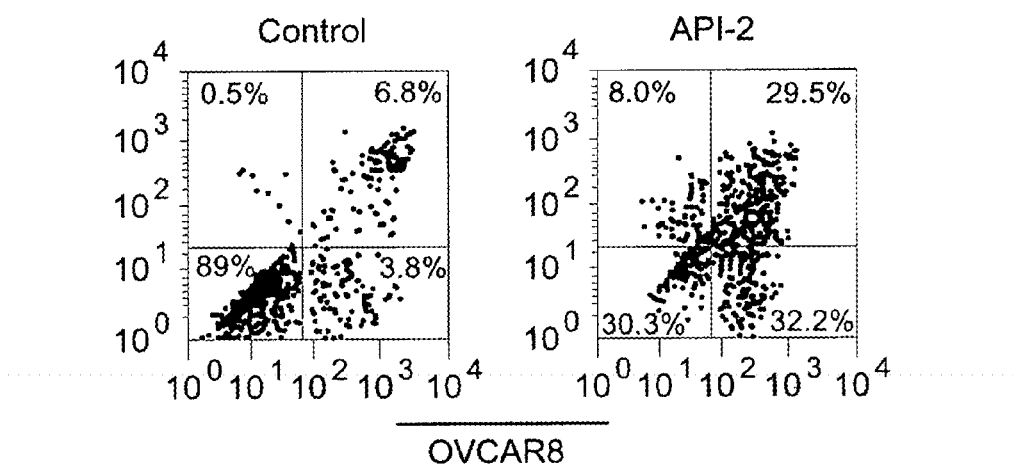
Figures 3, 3C:
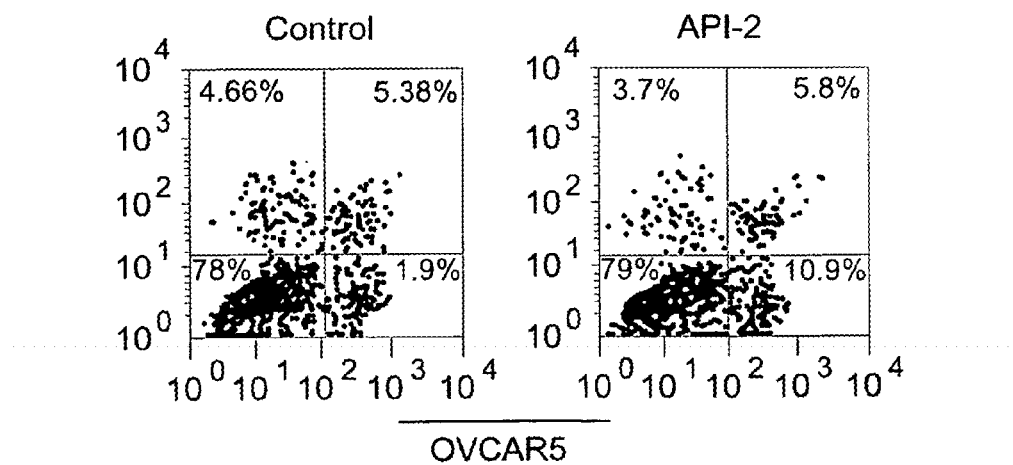
Figures 3, 3C, 4, 5:
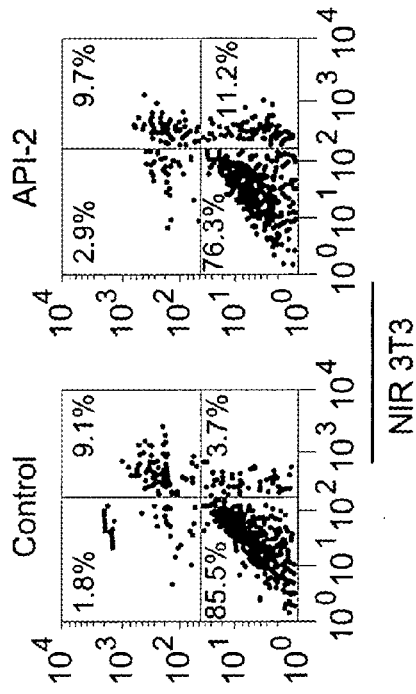
Figures 3, 3C, 4, 5, 6, 7:
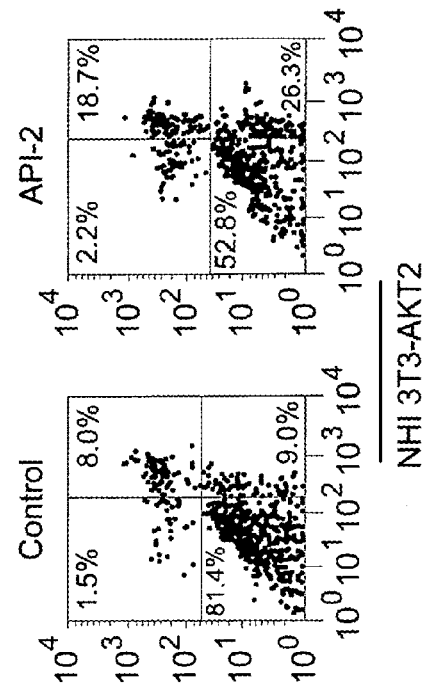
Figures 3, 3C, 4:
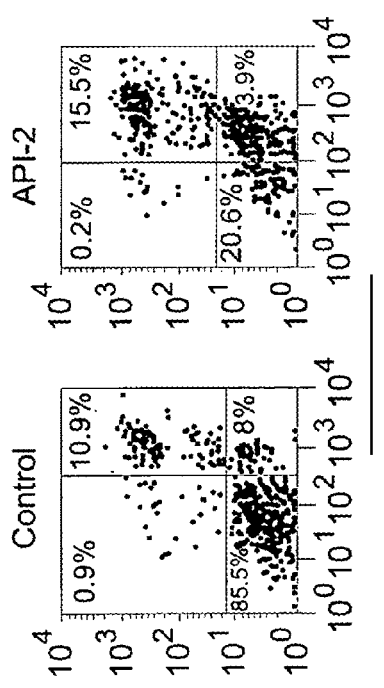
Figures 3, 3C, 4, 5, 6:
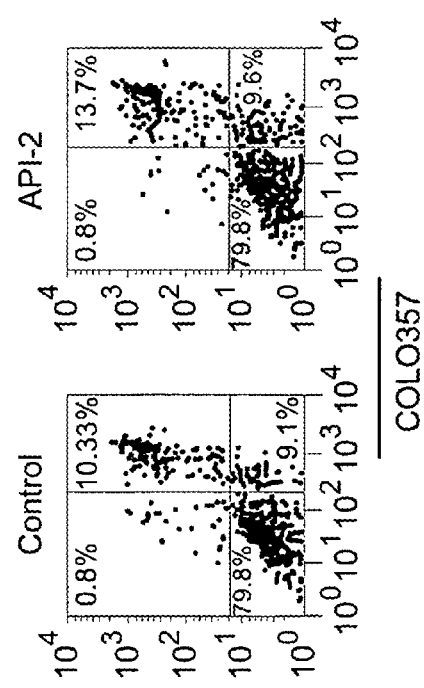

FIG. 3A-FIG. 3C-7 demonstrates that API-2 inhibits Akt activity and cell growth and induces apoptosis in human cancer cells with elevated Akt. FIG. 3A is a western blot, following treatment with API-2, phosphorylation levels of Akt were detected with anti-phospho-Akt-T308 antibody in indicated human cancer cell lines. The blots were reprobed with anti-total Akt antibody (bottom panels). In FIG. 3B, a cell proliferation assay is shown. Cell lines as indicated in the figure were treated with different doses of API-2 for 24 h and 48 h and then analyzed with CellTiter 96 Cell Proliferation Assay kit (Promega). FIG. 3C provides an apoptosis analysis. Cells were treated with API-2 and stained with annexin V and PI and analyzed by FACScan.

Figure 4A:
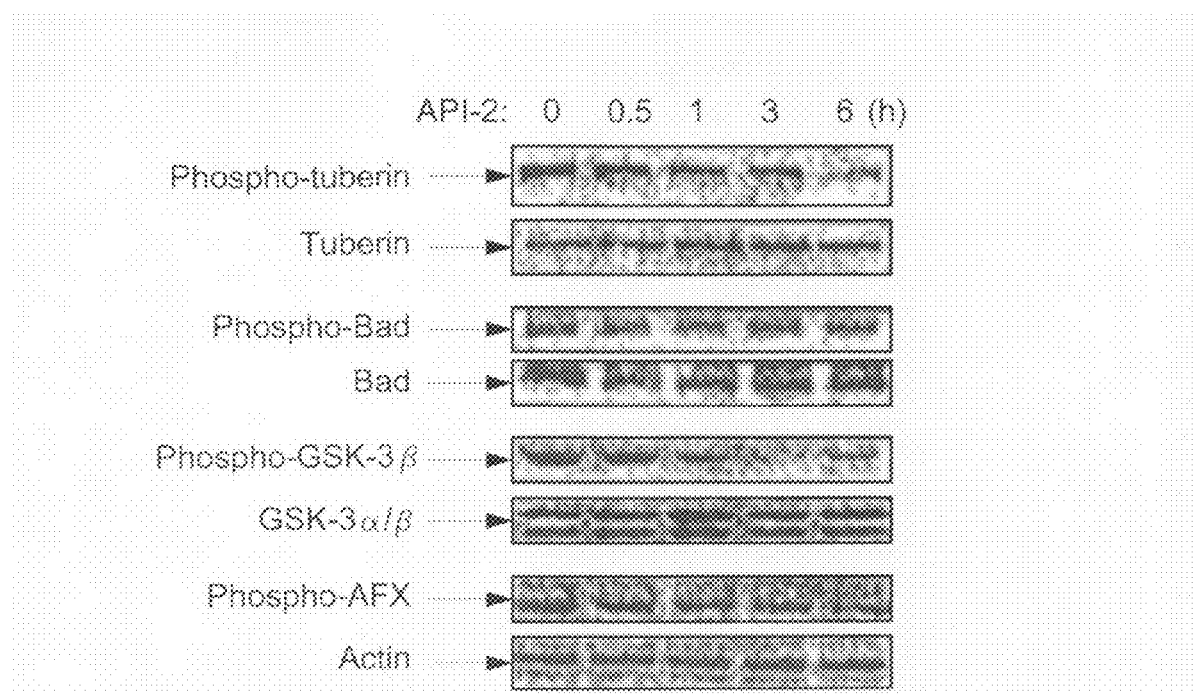
Figure 4C:
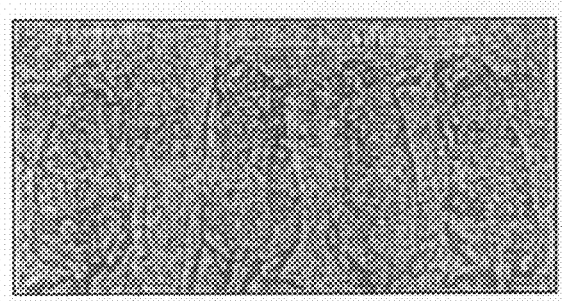
Figure 4E:
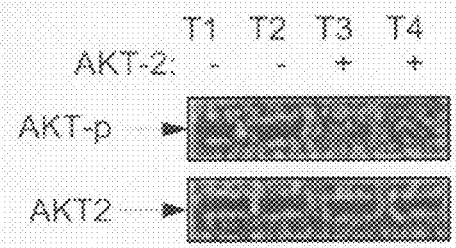
Figure 4D:
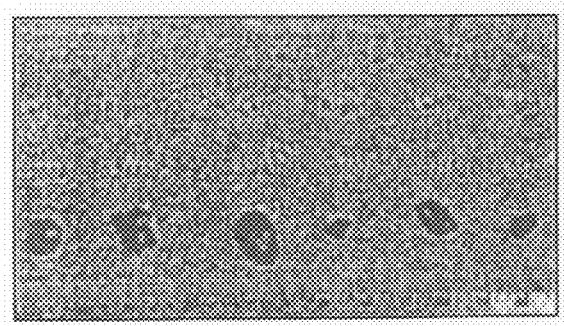
Figures 2, 4B:
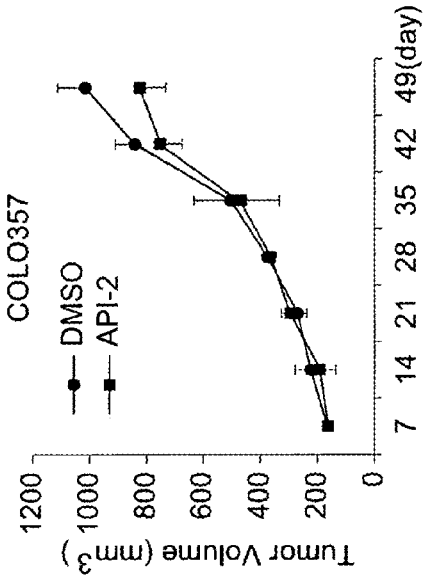
Figures 1, 4B:
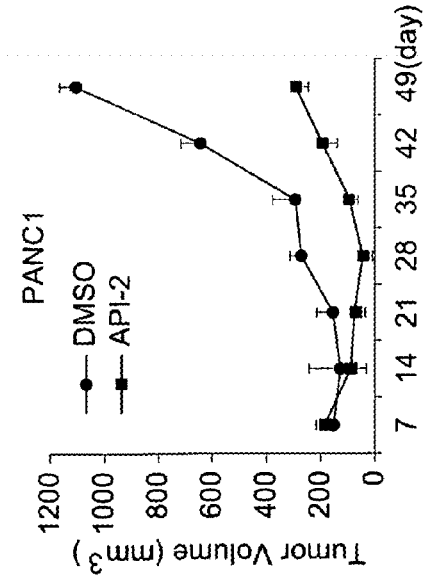
Figures 4, 4B, 5:
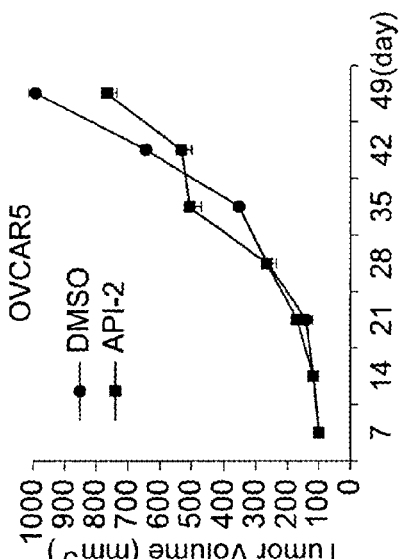
Figures 4, 4B:
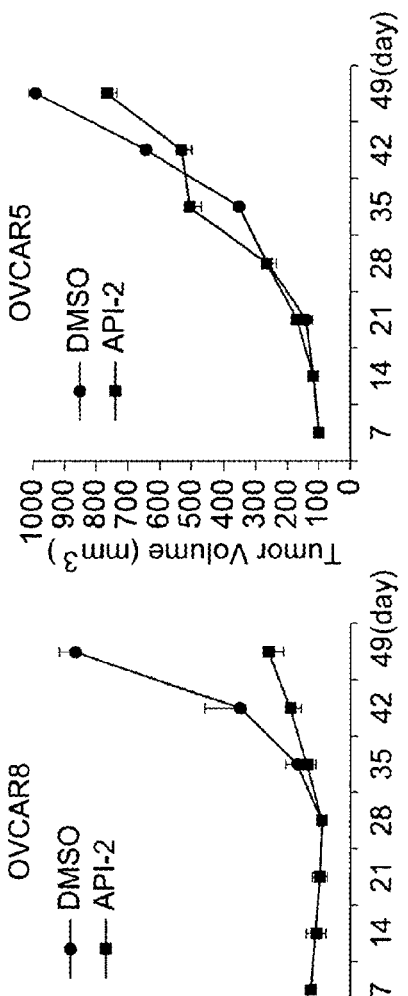
Figures 3, 4B:
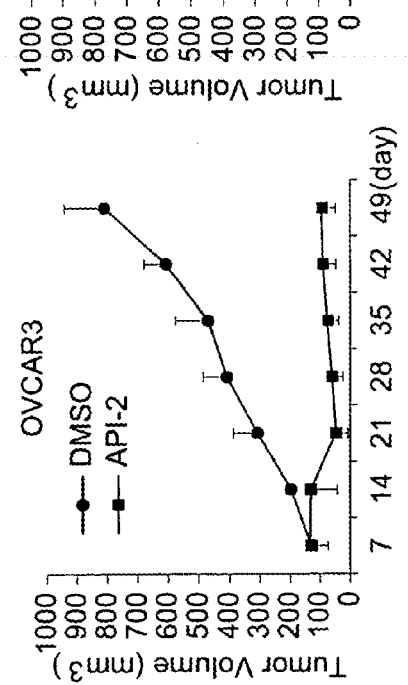
Figure 5:
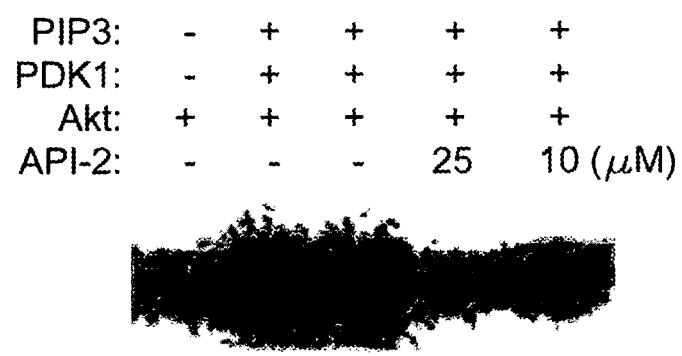
Figure 10:
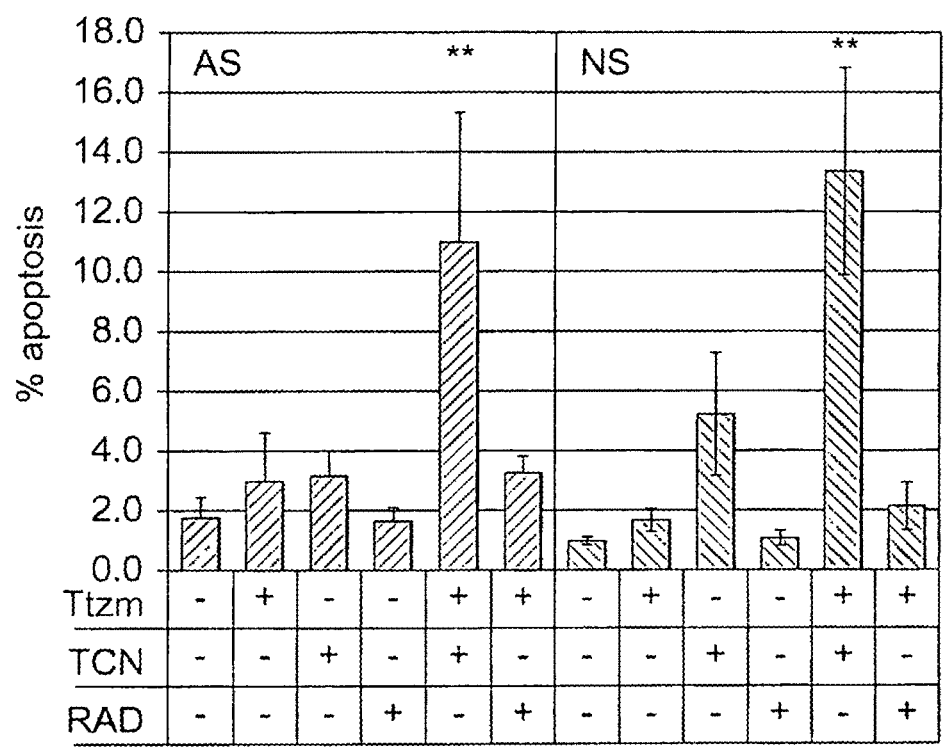

FIG. 4A-FIG. 4E shows that API-2 inhibits downstream targets of Akt and exhibits anti-tumor activity in cancer cell lines with elevated Akt in mouse xenograft. In FIG. 4A, it is demonstrated that API-2 inhibits Akt phosphorylation of tuberin, Bad, AFX and GSK-3β. Following treatment with API-2, OVAR3 cells were lysed and immunoblotted with indicated antibodies. FIG. 4B shows that API-2 inhibits tumor growth. Tumor cells were subcutaneously injected into nude mice with low level of Akt cells on left side and elevated level of Akt cells on right side. When the tumors reached an average size of about 100-150 mm$^3$, animals were treated with either vehicle or 1 mg/kg/day API-2. Each measurement represents an average of 10 tumors. FIG. 4C illustrates a representation of the mice with OVCAR3 (right) and OVCAR5 (left) xenograft treated with API-2 or vehicle (control). FIG. 4D shows examples of tumor size (bottom) and weight (top) at the end of experiment. In FIG. 4E, immunoblot analysis of tumor lysates was performed with anti-phospho-Akt-S473 (top) and anti-AKT2 (bottom) antibodies in OVCAR-3-derived tumors that were treated (T3 and T4) and untreated (T1 and T2) with API-2.

FIG. 5 shows that API-2 (triciribine) inhibits Akt kinase activity in vitro. In vitro kinase assay was performed with recombinant of PDK1 and Akt in a kinase buffer containing phosphatidylinositol-3,4,5-P3 (PIP3), API-2 and histone H2B as substrate. After incubation of 30 min, the reactions were separated by SDS-PAGE and exposed in a film.

FIG. 6A-FIG. 6D provides the mRNA and amino acid sequence of human Akt1, restriction enzyme sites are also noted.

FIG. 7A-FIG. 7D provides the mRNA and amino acid sequence of human Akt2 restriction enzyme sites are also noted.

FIG. 8A-FIG. 8D provides the mRNA and amino acid sequence of human Akt3 restriction enzyme sites are also noted.

FIG. 9A-FIG. 9C shows growth inhibition by the combination of trastuzumab and Akt/mTOR pathway inhibitors. PTEN anti-sense or non-specific oligonucleotide transfected BT474.ml cells were treated with inhibitors of the Akt/mTOR pathway alone or in combination with trastuzumab and the relative cell growth was assessed. FIG. 9A shows a panel of Akt/mTOR inhibitors. Growth inhibition was assessed in PTEN AS transfected BT474.ml cells. The doses shown are: Triciribine (TCN) 1 µM; RAD001 0.2 nM; QLT0267 10 µM; KP 372-1 0.05 µM; 4ADPIB 5 µM; Edelfosine 7.5 µM; and trastuzumab (Ttzm) 2 µg/ml. The standard deviation (SD) in the percent growth inhibition is indicated. Results shown are the combined data from 2-3 experiments with triplicates of each treatment within each experiment. FIG. 9B shows TCN inhibits cell growth in combination with trastuzumab. BT474.ml cells were transfected with PTEN AS oligonucleotide or non-specific (NS) oligonucleotide, treated with trastuzumab and TCN, alone and in combination, at multiple doses of TCN and assayed for growth inhibition. Trastuzumab was administered at a single concentration. FIG. 7C shows RAD001 inhibits cell growth in combination with trastuzumab. BT474.ml cells were transfected with PTEN AS oligonucleotide or non-specific (NS) oligonucleotide, treated with trastuzumab and RAD001, alone and in combination, at multiple doses of RAD001 and assayed for growth inhibition. For FIGS. 9B and 9C: * indicates a significant difference in growth inhibition following combination treatment as compared to either trastuzumab or TCN/TAD001 alone. P<0.05 was considered significant. Error bars depict the SEM.

FIG. 10 shows the synergistic effects on apoptosis. Twenty-four hours after plating, PTEN AS and NS transfected BT474.ml cells were treated as indicated with trastuzumab (Ttzm), TCN and/or RAD001 at the following concentrations: trastuzumab 2 µg/ml; triciribine 2.5 µM; RAD001 0.4 nM. Apo-BrdU Tunel assays were performed to assess apoptosis. The experiment was performed 3 times and the data shown is the mean apoptosis. Error bars depict the standard deviation. Trastuzumab+triciribine treatment significantly induced apoptosis (p<0.01) as compared with all other treatments.

Figure 11A:
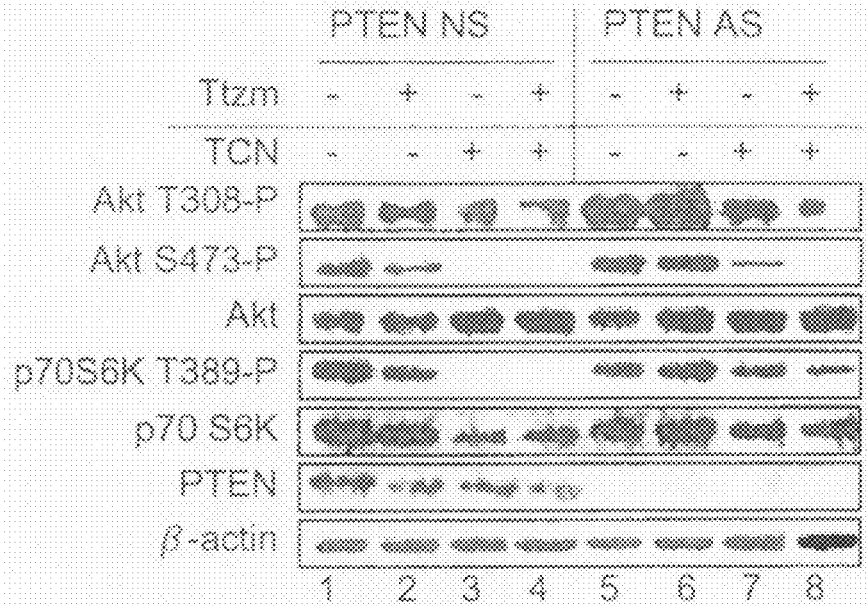
Figure 11B:
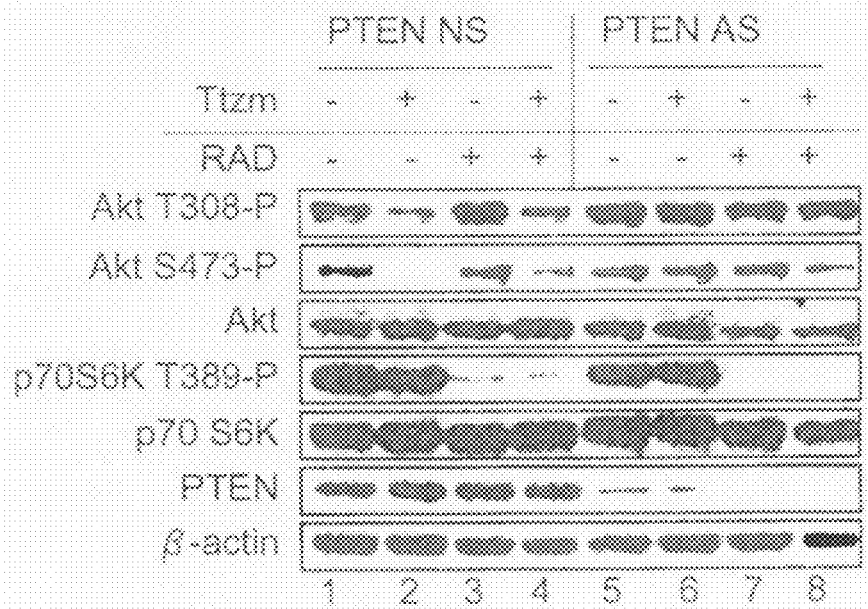

FIG. 11A-FIG. 11B shows inhibition of Akt and p70S6K activity. To evaluate the effects of these drugs on the Akt/mTOR pathway, PTEN AS and NS oligonucleotides were transfected int BT474.ml cells. Two days later, the cells were treated for 2 hours with trastuzumab and triciribine (TCN) (FIG. 11A) or trastuzumab and RAD001 (FIG. 11B). Total cell lysates were collected, separated by SDS-PAGE and immunoblotted as indicated. The concentration of trastuzumab was 2 μg/ml, triciribine was 2.5 μM and RAD001 was 0.4 nM. The experiments were repeated at least twice to insure that results were reproducible.

Figure 12B:
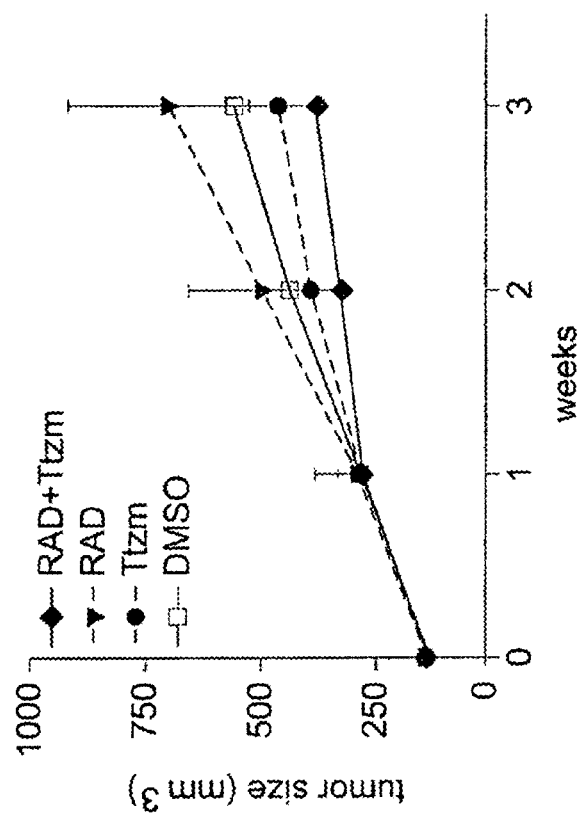
Figure 12A:
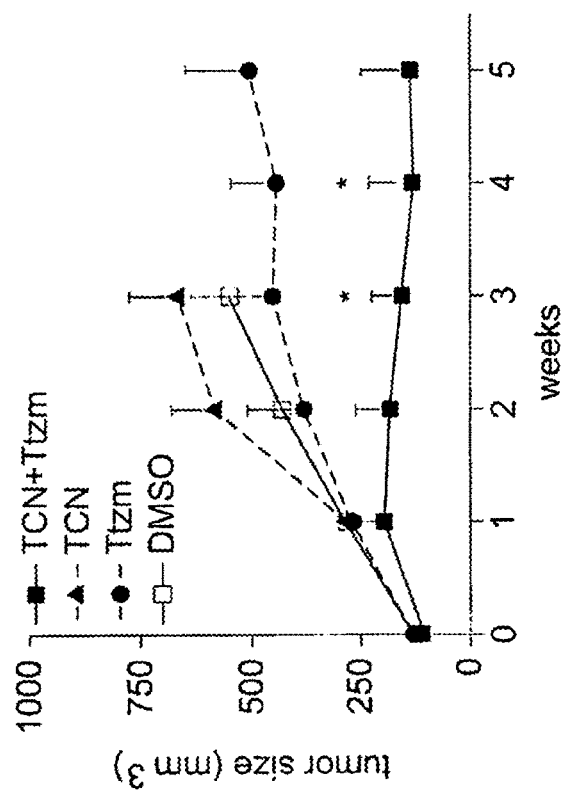

FIG. 12A-FIG. 12B shoes combination treatments inhibited tumor growth in a SCID mice xenograft model. SCID mice received BT474.ml breast cancer cell xenografts in mammary fat pad. The xenografts grew for 3 weeks to generate tumors with an average size of 100-150 $mm^3$. PTEN antisense oligonucleotides, trastuzumab, triciribine (FIG. 12A) and RAD001 (FIG. 12B) were administered. The tumors were measured twice weekly with calipers and tumor size was averaged for each treatment group. Error bars denote the standard error of the mean. * indicates a significant difference in growth inhibition following combination treatment as compared to either trastuzumab (Ttzm), TCN or DMSO alone. P<0.05 was considered significant.

5. DETAILED DESCRIPTION OF THE INVENTION

The inventors have determined, contrary to the prior art and experience, how to successfully use triciribine compounds in combination with one or more erlotinib-like compounds to treat tumors and cancer by one or a combination of (i) administering triciribine and one or more erlotinib-like compounds only to patients which according to a diagnostic test described below, exhibit enhanced sensitivity to the the triciribine compound and/or the erlotinib-like compounds; (ii) using a described dosage level that minimizes the toxicity of the the triciribine compound and/or the erlotinib-like compounds but yet still exhibits efficacy; or (iii) using a described dosage regimen that minimizes the toxicity of the the triciribine compound and/or the erlotinib-like compounds.

5.1. Definitions

As used herein, the term "compounds of the invention" refers to compounds disclosed herein including compounds of formula I-VIII, and combinations thereof.

As used herein, the terms "cancer" and "cancerous" refer to or describe the physiological condition in mammals that is typically characterized by unregulated cell growth, i.e., proliferative disorders. Examples of such proliferative disorders include cancers such as carcinoma, lymphoma, blastoma, sarcoma, and leukemia, as well as other cancers disclosed herein. More particular examples of such cancers include breast cancer, prostate cancer, colon cancer, squamous cell cancer, small-cell lung cancer, non-small cell lung cancer, gastrointestinal cancer, pancreatic cancer, cervical cancer, ovarian cancer, liver cancer, e.g., hepatic carcinoma, bladder cancer, colorectal cancer, endometrial carcinoma, kidney cancer, and thyroid cancer.

Other non-limiting examples of cancers are basal cell carcinoma, biliary tract cancer; bone cancer; brain and CNS cancer; choriocarcinoma; connective tissue cancer; esophageal cancer; eye cancer; cancer of the head and neck; gastric cancer; intra-epithelial neoplasm; larynx cancer; lymphoma including Hodgkin's and Non-Hodgkin's lymphoma; melanoma; myeloma; neuroblastoma; oral cavity cancer (e.g., lip, tongue, mouth, and pharynx); pancreatic cancer; retinoblastoma; rhabdomyosarcoma; rectal cancer; cancer of the respiratory system; sarcoma; skin cancer; stomach cancer; testicular cancer; uterine cancer; cancer of the urinary system, as well as other carcinomas and sarcomas.

As used herein, the term "tumor" refers to all neoplastic cell growth and proliferation, whether malignant or benign, and all pre-cancerous and cancerous cells and tissues. For example, a particular cancer may be characterized by a solid mass tumor. The solid tumor mass, if present, may be a primary tumor mass. A primary tumor mass refers to a growth of cancer cells in a tissue resulting from the transformation of a normal cell of that tissue. In most cases, the primary tumor mass is identified by the presence of a cyst, which can be found through visual or palpation methods, or by irregularity in shape, texture or weight of the tissue. However, some primary tumors are not palpable and can be detected only through medical imaging techniques such as X-rays (e.g., mammography), or by needle aspirations. The use of these latter techniques is more common in early detection. Molecular and phenotypic analysis of cancer cells within a tissue will usually confirm if the cancer is endogenous to the tissue or if the lesion is due to metastasis from another site.

The term alkyl, as used herein, unless otherwise specified, includes a saturated straight, branched, or cyclic, primary, secondary, or tertiary hydrocarbon of for example $C_1$ to $C_{24}$, and specifically includes methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The alkyl is optionally substituted, e.g., with one or more substituents such as halo (F, Cl, Br or I), (e.g. $CF_3$, 2-Br-ethyl, $CH_2F$, $CH_2Cl$, $CH_2CF_3$ or $CF_2CF_3$), hydroxyl (e.g. $CH_2OH$), amino (e.g. $CH_2NH_2$, $CH_2NHCH_3$ or $CH_2N(CH_3)_2$), alkylamino, arylamino, alkoxy, aryloxy, nitro, azido (e.g. $CH_2N_3$), cyano (e.g. $CH_2CN$), sulfonic acid, sulfate, phosphonic acid, phosphate, or phosphonate, either unprotected, or protected as necessary, as known to those skilled in the art, for example, as taught in Greene et al., *Protective Groups in Organic Synthesis*, 1991, 2d Ed., John Wiley and Sons, NY, hereby incorporated by reference.

The term lower alkyl, as used herein, and unless otherwise specified, refers to a $C_1$ to $C_4$ saturated straight, branched, or if appropriate, a cyclic (for example, cyclopropyl) alkyl group, including both substituted and unsubstituted forms.

The term alkylamino or arylamino includes an amino group that has one or two alkyl or aryl substituents, respectively.

The term amino acid includes naturally occurring and synthetic α, β, γ or δ amino acids, and includes but is not limited to, amino acids found in proteins, i.e. glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine. In a preferred embodiment, the amino acid is in the L-configuration. Alternatively, the amino acid can be a derivative of alanyl, valinyl, leucinyl, isoleuccinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-valinyl, β-leucinyl, β-isoleuccinyl, β-prolinyl, β-phenylalaninyl, β-tryptophanyl, β-methioninyl, β-glycinyl, β-serinyl, β-threoninyl, β-cysteinyl, β-tyrosinyl, β-asparaginyl, β-glutaminyl, β-aspartoyl, β-glutaroyl, β-lysinyl, β-argininyl or β-histidinyl. When the term amino acid is used, it is considered to be a specific and independent disclosure of each of the esters of a natural or synthetic amino acid, including but not limited to α, β, γ or δ glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine in the D and L-configurations.

The term "protected" as used herein and unless otherwise defined includes a group that is added to an oxygen, nitrogen, sulfur or phosphorus atom to prevent its further reaction or for other purposes. A wide variety of oxygen and nitrogen protecting groups are known to those skilled in the art of organic synthesis (see Greene and Wuts, *Protective Groups in Organic Synthesis,* 1999, 3d Ed., John Wiley & Sons, Inc., NY).

The term aryl, as used herein, and unless otherwise specified, includes phenyl, biphenyl, or naphthyl, and preferably phenyl. The aryl group is optionally substituted with one or more moieties such as halo, hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene et al., *Protective Groups in Organic Synthesis,* 1999, $3^{rd}$ Ed., John Wiley and Sons, NY.

The term alkaryl or alkylaryl includes an alkyl group with an aryl substituent. The term aralkyl or arylalkyl includes an aryl group with an alkyl substituent.

The term halo, as used herein, includes chloro, bromo, iodo, and fluoro.

The term acyl includes a carboxylic acid ester in which the non-carbonyl moiety of the ester group is selected from straight, branched, or cyclic alkyl or lower alkyl, alkoxyalkyl including methoxymethyl, aralkyl including benzyl, aryloxyalkyl such as phenoxymethyl, aryl including phenyl optionally substituted with halogen, $C_1$ to $C_4$ alkyl or $C_1$ to $C_4$ alkoxy, sulfonate esters such as alkyl or aralkyl sulphonyl including methanesulfonyl, the mono, di or triphosphate ester, trityl or monomethoxytrityl, substituted benzyl, trialkylsilyl (e.g. dimethyl-t-butylsilyl) or diphenylmethylsilyl. Aryl groups in the esters optimally comprise a phenyl group. The term "lower acyl" refers to an acyl group in which the non-carbonyl moiety is lower alkyl.

As used herein, the term "substantially free of" or "substantially in the absence of" with respect to enantiomeric purity, refers to a composition that includes at least 85% or 90% by weight, preferably 95% to 98% by weight, and even more preferably 99% to 100% by weight, of the designated enantiomer. In a preferred embodiment, in the methods and compounds of this invention, the compounds are substantially free of other enantiomers.

Similarly, the term "isolated" refers to a compound composition that includes at least 85% or 90% by weight, preferably 95% to 98% by weight, and even more preferably 99% to 100% by weight, of the compound, the remainder comprising other chemical species or enantiomers.

The term "independently" is used herein to indicate that the variable, which is independently applied, varies independently from application to application. Thus, in a compound such as R"XYR", wherein R" is "independently carbon or nitrogen," both R" can be carbon, both R" can be nitrogen, or one R" can be carbon and the other R" nitrogen.

The term "pharmaceutically acceptable salt or prodrug" is used throughout the specification to describe any pharmaceutically acceptable form (such as an ester, phosphate ester, salt of an ester or a related group) of a compound, which, upon administration to a patient, provides the compound. Pharmaceutically acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the pharmaceutical art. Pharmaceutically acceptable prodrugs refer to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound.

The term "pharmaceutically acceptable esters" as used herein, unless otherwise specified, includes those esters of one or more compounds, which are, within the scope of sound medical judgment, suitable for use in contact with the tissues of hosts without undue toxicity, irritation, allergic response and the like, are commensurate with a reasonable benefit/risk ratio, and are effective for their intended use.

The term "subject" as used herein refers to an animal, preferably a mammal, most preferably a human. Mammals can include non-human mammals, including, but not limited to, pigs, sheep, goats, cows (bovine), deer, mules, horses, monkeys and other non-human primates, dogs, cats, rats, mice, rabbits or any other known or disclosed herein.

5.2. Compounds of the Invention

The present invention provides for the use of TCN, TCN-P and related compounds in combination with an erlotinib-like compound, for example, gefitinib, erlotinib or a salt thereof for use in particular therapeutic regimens for the treatment of proliferative disorders.

As used herein and unless otherwise indicated, the term "triciribine compounds" and "triciribine and related compounds" refers to compounds having the following structures:

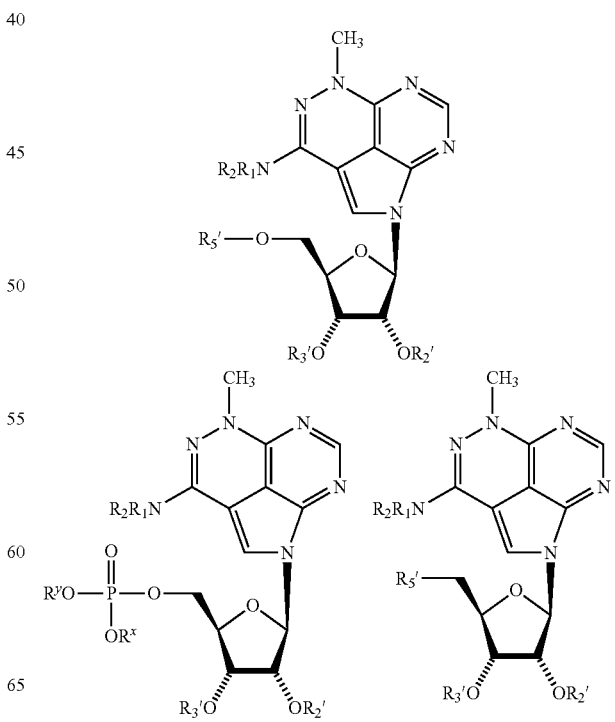

-continued

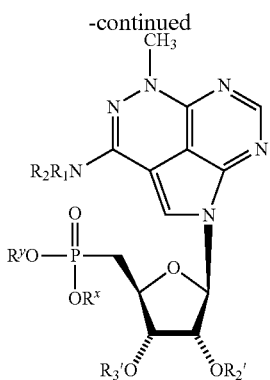

wherein each R2', R3' and R5' are independently hydrogen, optionally substituted phosphate or phosphonate (including mono-, di-, or triphosphate or a stabilized phosphate prodrug); acyl (including lower acyl); alkyl (including lower alkyl); amide, sulfonate ester including alkyl or arylalkyl; sulfonyl, including methanesulfonyl and benzyl, wherein the phenyl group is optionally substituted with one or more substituents as for example as described in the definition of an aryl given herein; optionally substituted arylsulfonyl; a lipid, including a phospholipid; an amino acid; a carbohydrate; a peptide; or cholesterol; or other pharmaceutically acceptable leaving group that, in vivo, provides a compound wherein R2', R3' or R5' is independently H or mono-, di- or tri-phosphate;

wherein $R^x$ and $R^y$ are independently hydrogen, optionally substituted phosphate; acyl (including lower acyl); amide, alkyl (including lower alkyl); aromatic, polyoxyalkylene such as polyethyleneglycol, optionally substituted arylsulfonyl; a lipid, including a phospholipid; an amino acid; a carbohydrate; a peptide; or cholesterol; or other pharmaceutically acceptable leaving group. In one embodiment, the compound is administered as a 5'-phosphoether lipid or a 5'-ether lipid.

$R_1$ and $R_2$ each are independently H, optionally substituted straight chained, branched or cyclic alkyl (including lower alkyl), alkenyl, or alkynyl, CO-alkyl, CO-alkenyl, CO-alkynyl, CO-aryl or heteroaryl, CO-alkoxyalkyl, CO-aryloxyalkyl, CO-substituted aryl, sulfonyl, alkylsulfonyl, arylsulfonyl, aralkylsulfonyl.

In one embodiment, R2' and R3' are hydrogen. In another embodiment, R2' and R5' are hydrogen. In yet another embodiment, R2', R3' and R5' are hydrogen. In yet another embodiment, R2', R3', R5', R1 and R2 are hydrogen.

In another embodiment, the triciribine compound has the following structure:

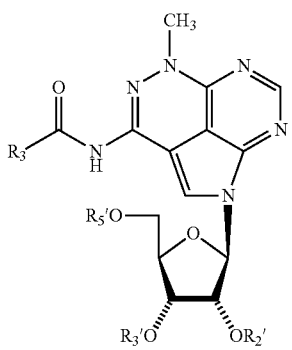

wherein $R_3$ is H, optionally substituted straight chained, branched or cyclic alkyl (including lower alkyl), alkenyl, or alkynyl, $NH_2$, $NHR^4$, $N(R^4)_2$, aryl, alkoxyalkyl, aryloxyalkyl, or substituted aryl; and each $R^4$ independently is H, acyl including lower acyl, alkyl including lower alkyl such as but not limited to methyl, ethyl, propyl and cyclopropyl, alkenyl, alkynyl, cycloalkyl, alkoxy, alkoxyalkyl, hydroxyalkyl, or aryl. In a subembodiment, $R_3$ is a straight chained C1-11 alkyl, iso-propyl, t-butyl, or phenyl.

In one embodiment, the triciribine compounds provided herein have the following structure:

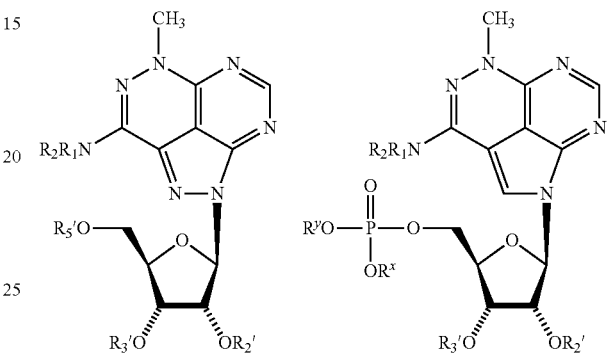

In another embodiment, the triciribine compounds provided herein have the following structure:

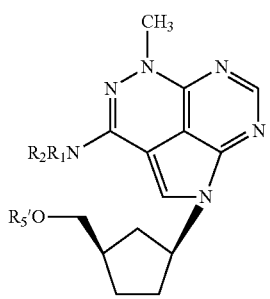

In another embodiment, the triciribine compounds provided herein have the following structure:

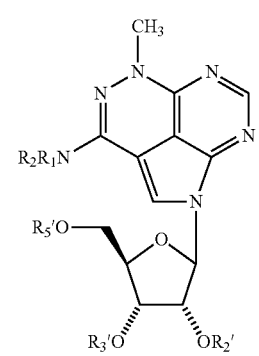

wherein $R_6$ is H, alkyl, (including lower alkyl) alkenyl, alkynyl, alkoxyalkyl, hydroxyalkyl, arylalkyl, cycloalkyl, $NH_2$, $NHR^4$, $NR^4R^4$, $CF_3$, $CH_2OH$, $CH_2F$, $CH_2Cl$, $CH_2CF_3$, $C(Y^3)_3$, $C(Y^3)_2C(Y^3)_3$, $C(=O)OH$, $C(=O)OR^4$, $C(=O)$- alkyl, C(=O)-aryl, C(=O)-alkoxyalkyl, C(=O)NH₂, C(=O)NHR⁴, C(=O)N(R⁴)₂, where each Y³ is independently H or halo; and each R⁴ independently is H, acyl including lower acyl, alkyl including lower alkyl such as but not limited to methyl, ethyl, propyl and cyclopropyl, alkenyl, alkynyl, cycloalkyl, alkoxy, alkoxyalkyl, hydroxyalkyl, or aryl.

In a subembodiment, $R_6$ is ethyl, $CH_2CH_2OH$, or $CH_2$-phenyl.

In another embodiment, the triciribine compounds provided herein have the following structure:

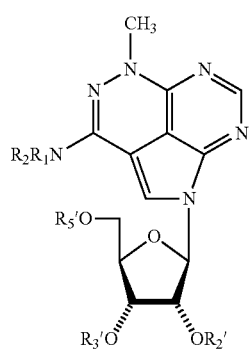

wherein $R_7$ is H, halo, alkyl (including lower alkyl), alkenyl, alkynyl, alkoxy, alkoxyalkyl, hydroxyalkyl, cycloalkyl, nitro, cyano, OH, OR⁴, NH₂, NHR⁴, NR⁴R⁴, SH, SR⁴, CF₃, CH₂OH, CH₂F, CH₂Cl, CH₂CF₃, C(Y³)₃, C(Y³)₂C(Y³)₃, C(=O)OH, C(=O)OR⁴, C(=O)-alkyl, C(=O)-aryl, C(=O)-alkoxyalkyl, C(=O)NH₂, C(=O)NHR⁴, C(=O)N(R⁴)₂, or N₃, where each Y³ is independently H or halo; and each R⁴ independently is H, acyl including lower acyl, alkyl including lower alkyl such as but not limited to methyl, ethyl, propyl and cyclopropyl, alkenyl, alkynyl, cycloalkyl, alkoxy, alkoxyalkyl, hydroxyalkyl.

In a subembodiment, $R_7$ is methyl, ethyl, phenyl, chloro or NH₂.

In another embodiment, the triciribine compounds provided herein have the following structure:

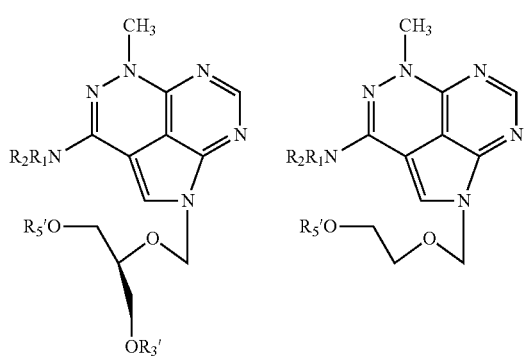

In another embodiment, the triciribine compounds provided herein have the following structure:

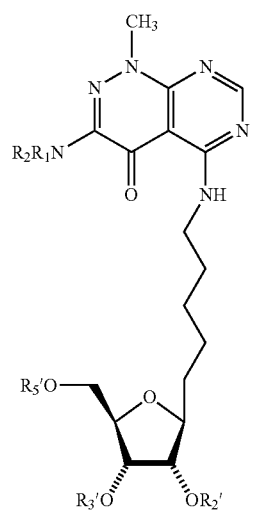

As used herein and unless otherwise indicated, the term "epidermal growth factor receptor inhibitor" refers to compounds that target the epidermal growth factor receptor (EGFR) tyrosine kinase, which is highly expressed and occasionally mutated in various forms of cancer. In certain embodiments, the compounds bind in a reversible fashion to the adenosine triphosphate (ATP) binding site of the receptor. In certain embodiments, two members of the EGFR family come together to form a homodimer. These then use the molecule of ATP to autophosphorylate each other, which causes a conformational change in their intracellular structure, exposing a further binding site for binding proteins that cause a signal cascade to the nucleus. By inhibiting the ATP, autophosphorylation is not possible and the signal is stopped. Illustrative examples of epidermal growth factor receptor inhibitor compounds include erlotinib-like compounds such as for example, gefitinib and erlotinib.

As used herein and unless otherwise indicated, the term "erlotinib-like compounds" refers to a compound of formula:

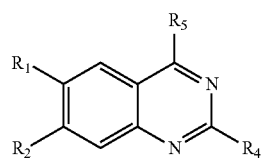

wherein each R1 and R2 is independently hydrogen, independently optionally substituted alkoxy, optionally substituted amine, aromatic amine, heteroaromatic amine, optionally substituted straight chained, branched or cyclic alkyl;

each R3 and R4 is independently hydrogen, independently optionally substituted aromatic amine, heteroaromatic amine, or cyclic amine. In an illustrative embodiment, the erlotinib-like compounds include, but are limited to, the following structure:

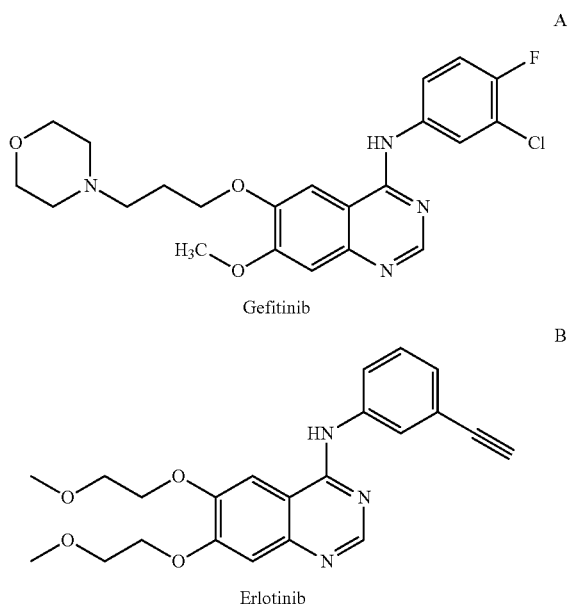

A Gefitinib

B Erlotinib

It is to be understood that the compounds disclosed herein may contain chiral centers. Such chiral centers may be of either the (R) or (S) configuration, or may be a mixture thereof. Thus, the compounds provided herein may be enantiomerically pure, or be stereoisomeric or diastereomeric mixtures. It is understood that the disclosure of a compound herein encompasses any racemic, optically active, polymorphic, or steroisomeric form, or mixtures thereof, which preferably possesses the useful properties described herein, it being well known in the art how to prepare optically active forms and how to determine activity using the standard tests described herein, or using other similar tests which are will known in the art. Examples of methods that can be used to obtain optical isomers of the compounds include the following:

(i) physical separation of crystals—a technique whereby macroscopic crystals of the individual enantiomers are manually separated. This technique can be used if crystals of the separate enantiomers exist, i.e., the material is a conglomerate, and the crystals are visually distinct;

(ii) simultaneous crystallization—a technique whereby the individual enantiomers are separately crystallized from a solution of the racemate, possible only if the latter is a conglomerate in the solid state;

(iii) enzymatic resolutions—a technique whereby partial or complete separation of a racemate by virtue of differing rates of reaction for the enantiomers with an enzyme (iv) enzymatic asymmetric synthesis—a synthetic technique whereby at least one step of the synthesis uses an enzymatic reaction to obtain an enantiomerically pure or enriched synthetic precursor of the desired enantiomer;

(v) chemical asymmetric synthesis—a synthetic technique whereby the desired enantiomer is synthesized from an achiral precursor under conditions that produce asymmetry (i.e., chirality) in the product, which may be achieved using chiral catalysts or chiral auxiliaries;

(vi) diastereomer separations—a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

(vii) first- and second-order asymmetric transformations—a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

(viii) kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

(ix) enantiospecific synthesis from non-racemic precursors—a synthetic technique whereby the desired enantiomer is obtained from non-chiral starting materials and where the stereochemical integrity is not or is only minimally compromised over the course of the synthesis;

(x) chiral liquid chromatography—a technique whereby the enantiomers of a racemate are separated in a liquid mobile phase by virtue of their differing interactions with a stationary phase. The stationary phase can be made of chiral material or the mobile phase can contain an additional chiral material to provoke the differing interactions;

(xi) chiral gas chromatography—a technique whereby the racemate is volatilized and enantiomers are separated by virtue of their differing interactions in the gaseous mobile phase with a column containing a fixed non-racemic chiral adsorbent phase;

(xii) extraction with chiral solvents—a technique whereby the enantiomers are separated by virtue of preferential dissolution of one enantiomer into a particular chiral solvent;

(xiii) transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one enantiomer of the racemate to pass through.

In some embodiments, triciribine, triciribine phosphate (TCN-P), triciribine 5'-phosphate (TCN-P), or the DMF adduct of triciribine (TCN-DMF) are provided. TCN can be synthesized by any technique known to one skilled in the art, for example, as described in Tetrahedron Letters, 1971. 49: p. 4757-4760. TCN-P can be prepared by any technique known to one skilled in the art, for example, as described in U.S. Pat. No. 4,123,524. The synthesis of TCN-DMF is described, for example, in INSERM, 1978. 81: p. 37-82. Other compounds related to TCN as described herein can be synthesized, for example, according to the methods disclosed in Gudmundsson K. S. et al., Nucleosides Nucleotides Nucleic Acids, 2001. 20(10-11): p. 1823-1830; Porcari A. R. et al., J Med Chem, 2000. 43(12): p. 2457-2463; Porcari A. R. et al., Nucleosides Nucleotides, 1999. 18(11-12): p. 2475-2497; Porcari A. R. et al., J Med Chem, 2000. 43(12): p. 2438-2448; Porcari A. R. et al., Nucleosides Nucleotides Nucleic Acids, 2003. 22(12): p. 2171-2193; Porcari A. R. et al., Nucleosides Nucleotides Nucleic Acids, 2004. 23(1-2): p. 31-39; Schweinsberg P. D. et al., Biochem Pharmacol, 1981. 30(18): p. 2521-2526; Smith K. L. et al., Bioorg Med Chem Lett, 2004. 14(13): p. 3517-3520; Townsend L. B. et al., Nucleic Acids Symp Ser, 1986. 1986(17): p. 41-44; and/or Wotring L. L. et al., Cancer Treat Rep, 1986. 70(4): p. 491-7.

5.3. Pharmaceutically Acceptable Salts and Prodrugs

In cases where compounds are sufficiently basic or acidic to form stable nontoxic acid or base salts, administration of the compound as a pharmaceutically acceptable salt may be appropriate. Pharmaceutically acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the pharmaceutical art. In particular, examples of pharmaceutically acceptable salts are organic acid addition salts formed with acids, which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including, sulfate, nitrate, bicarbonate, and carbonate salts.

Pharmaceutically acceptable salts may be obtained using standard procedures well known in the art, for example reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Any of the nucleotides described herein can be administered as a nucleotide prodrug to increase the activity, bioavailability, stability or otherwise alter the properties of the nucleoside. A number of nucleotide prodrug ligands are known. In general, alkylation, acylation or other lipophilic modification of the mono, di or triphosphate of the nucleoside will increase the stability of the nucleotide. Examples of substituent groups that can replace one or more hydrogens on the phosphate moiety are alkyl, aryl, steroids, carbohydrates, including sugars, 1,2-diacylglycerol and alcohols. Many are described in R. Jones and N. Bischofberger, Antiviral Research, 1995. 27: p. 1-17. Any of these can be used in combination with the disclosed nucleosides to achieve a desired effect.

In one embodiment, the triciribine or a related compound is provided as 5'-hydroxyl lipophilic prodrug. Nonlimiting examples of U.S. patents that disclose suitable lipophilic substituents that can be covalently incorporated into the nucleoside, preferably at the 5'-OH position of the nucleoside or lipophilic preparations, include U.S. Pat. Nos. 5,149,794, 5,194,654, 5,223,263, 5,256,641, 5,411,947, 5,463,092, 5,543,389, 5,543,390, 5,543,391, and 5,554,728, all of which are incorporated herein by reference.

Foreign patent applications that disclose lipophilic substituents that can be attached to the triciribine or a related compound s of the present invention, or lipophilic preparations, include WO 89/02733, WO 90/00555, WO 91/16920, WO 91/18914, WO 93/00910, WO 94/26273, WO/15132, EP 0 350 287, EP 93917054.4, and WO 91/19721.

Additional nonlimiting examples of derivatives of triciribine or related compounds are those that contain substituents as described in the following publications. These derivatized triciribine or related compounds can be used for the indications described in the text or otherwise as antiviral agents, including as anti-HIV or anti-HBV agents. Ho D. H. W., Cancer Res., 1973 33: p. 2816-2820; Holy A. in Advances in Antiviral Drug Design, Vol. 1, De Clercq (ed.), JAI Press, pp. 179-231; Hong C. I. et al. Biochem Biophys Rs Commun, 1979. 88: p. 1223-1229; Hong C. I. et al., J Med Chem, 1980. 28: p. 171-177; Hostetler K. Y. et al., J Biol Chem, 1990. 266: p. 11714-11717; Hostetler K. Y. et al, Antiviral Res, 1994. 24: p. 59-67; Hostetler K. Y. et al, Antimicrobial Agents Chemother, 1994. 38: p. 2792-2797; Hunston R. N. et al, J Med Chem, 1984. 27: p. 440-444; Ji Y. H. et al, J Med Chem, 1990. 33: p. 2264-2270; Jones A. S. et al., J Chem Soc Perkin Trans, 1984. 1: p. 1471-1474; Juodka B. A. and Smart J., Coll Czech Chem Comm, 1974. 39: p. 363-968; Kataoka S. et al, Nucleic Acids Res Sym Ser, 1989. 21: p. 1-2; Kataoka S. et al, Heterocycles, 1991. 32: p. 1351-1356; Kinchington D. et al, Antiviral Chem Chemother, 1992. 3: p. 107-112; Kodama K. et al., Jpn J Cancer Res, 1989. 80: p. 679-685; Korty M. and Engels J., Naunyn-Schmiedeberg's Arch Pharmacol, 1979. 10: p. 103-111; Kumar A. et al., J Med Chem, 1990. 33: p. 2368-2375; LeBec C. and Huynh-dinh T., Tetrahedron Lett, 1991. 32: p. 6553-6556; Lichtenstein J. et al., J Biol Chem, 1960. 235: p. 457-465; Lucthy J. et al., Mitt Geg Lebensmittelunters Hyg, 1981. 72: p. 131-133 (Chem. Abstr. 95, 127093); McGuigan C. et al., Nucleic Acids Res, 1989. 17: p. 6065-6075; McGuigan C. et al., Antiviral Chem Chemother, 1990. 1: p. 107-113; McGuigan C. et al, Antiviral Chem Chemother, 1990. 1: p. 355-360; McGuigan C. et al., Antiviral Chem Chemother, 1990. 1: p. 25-33; McGuigan C. et al., Antiviral Res, 1991. 15: p. 255-263; McGuigan C. et al., Antiviral Res, 1992. 17: p. 311-321; McGuigan C. et al., Antiviral Chem Chemother, 1993.4: p. 97-101; McGuigan C. et al., J Med Chem, 1993. 36: p. 1048-1052.

Alkyl hydrogen phophonate derivatives of the anti-HIV agent AZT may be less toxic than the parent nucleoside analogue. Antiviral Chem Chemother. 5: 271-277; Meyer R. B. et al., Tetrahedron Lett, 1973. 269-272; Nagyvary J. et al., Biochem Biophys Res Commun, 1973. 55: p. 1072-1077; Namane A. et al., J Med Chem, 1992. 35: p. 3939-3044; Nargeot J. et al., Natl. Acad. Sci. U.S.A., 1983. 80: p. 2395-2399; Nelson K. A. et al., J Am Chem Soc, 1987. 109: p. 4058-4064; Nerbonne J. M. et al., Nature, 1984. 301: p. 74-76; Neumann J. M. et al., J Am Chem Soc, 1 1989. 111: p. 4270-4277; Ohno R. et al., Oncology, 1991. 48: p. 451-455. Palomino E. et al., J Med Chem, 1989. 32: p. 622-625; Perkins R. M. et al., Antiviral Res, 1993. 20(Suppl. 1): p. 84; Piantadosi C. et al., J Med Chem, 1991. 34: 1408-1414; Pompon A. et al., Antiviral Chem Chemother, 1994. 5: p. 91-98; Postemark T., Anu Rev Pharmacol, 1974. 14: p. 23-33; Prisbe E. J. et al., J Med Chem, 1986. 29: p. 671-675; Pucch F. et al., Antiviral Res, 1993. 22: p. 155-174; Pugaeva V. P. et al., Gig Trf Prof Zabol, 1969. 13: p. 47-48 (Chem. Abstr. 72, 212); Robins R. K., Pharm Res, 1984. 11-18; Rosowsky A. et al., J Med Chem, 1982. 25: p. 171-178; Ross W., Biochem Pharm, 1961. 8: p. 235-240; Ryu E. K. et al., J Med Chem, 1982. 25: p. 1322-1329; Saffhill R. and Hume W. J., Chem Biol Interact, 1986. 57: p. 347-355; Saneyoshi M. et al., Chem Pharm Bull, 1980. 28: p. 2915-2923; Sastry J. K. et al., Mol Pharmacol, 1992. 41: p. 441-445; Shaw J. P. et al., 9th Annual AAPS Meeting, 1994. San Diego, Calif. (Abstract). Shuto S. et al., Tetrahedron Lett, 1987. 28: p. 199-202; Shuto S. et al., Chem Pharm Bull, 1988. 36: p. 209-217. One preferred phosphate prodrug group is the S-acyl-2-thioethyl group, also referred to as "SATE."

Additional examples of prodrugs that can be used are those described in the following patents and patent applications: U.S. Pat. Nos. 5,614,548, 5,512,671, 5,770,584, 5,962,437, 5,223,263, 5,817,638, 6,252,060, 6,448,392, 5,411,947, 5,744,592, 5,484,809, 5,827,831, 5,696,277, 6,022,029, 5,780,617, 5,194,654, 5,463,092, 5,744,461, 4,444,766, 4,562,179, 4,599,205, 4,493,832, 4,221,732, 5,116,992, 6,429,227, 5,149,794, 5,703,063, 5,888,990, 4,810,697, 5,512,671, 6,030,960, 2004/0259845, U.S. Pat. No. 6,670,341, 2004/0161398, 2002/082242, U.S. Pat. No. 5,512,671, 2002/0082242, and or PCT Publication Nos WO 90/11079, WO 96/39197, and/or WO 93/08807.

5.4. In Vivo Efficacy/Dosing Regimens

In another aspect of the present invention, dosing regimens are provided that limit the toxic side effects of TCN and related compounds. In one embodiment, such dosing regimens minimize the following toxic side effects, including, but not limited to, hepatoxicity, thrombocytopenia, hyperglycemia, vomiting, hypocalcemia, anemia, hypoalbunemia, myelosuppression, hypertriglyceridemia, hyperamylasemia, diarrhea, stomachitis and/or fever.

In another embodiment, the administration of TCN, TCN-P or related compounds and an erlotinib-like compound, for example, gefitinib, erlotinib or a salt thereof, provides at least a partial or complete response in vivo in at least 15-20% of the subjects. In particular embodiments, a partial response can be at least 15, 20, 25, 30, 35, 40, 50, 55, 60, 65, 70, 75, 80 or 85% regression of the tumor. In other embodiments, this response can be evident in at least 15, 15, 20, 25, 30, 35, 40, 50, 55, 60, 65, 70, 75, 80, 85 or 90% of the subjects treated with the therapy. In further embodiments, such response rates can be obtained by any therapeutic regimen disclosed herein.

In other embodiments, methods are provided to treat a subject that has been diagnosed with cancer by administering to the subject an effective amount of TCN, TCN-P or a related compound and an erlotinib-like compound, for example, gefitinib, erlotinib or a salt thereof, according to a dosing schedule that includes administering the the triciribine compound and/an erlotinib-like compound, for example, gefitinib, erlotinib or a salt thereof, one time per week for three weeks followed by a one week period wherein the drug is not administered (i.e., via a 28 day cycle). In other embodiments, such 28 day cycles can be repeated at least 2, 3, 4, or 5 times or until regression of the tumor is evident.

In further embodiments, a 42 day cycle is provided in which the compounds disclosed herein can be administered once a week for four weeks followed by a two week period in which the the triciribine compound and/or an erlotinib-like compound, for example, gefitinib, erlotinib or a salt thereof, is not administered. In other embodiments, such 42 day cycles can be repeated at least 2, 3, 4, or 5 times or until regression of the tumor is evident. In a particular embodiment, less than 12, less than 11 or less than 10 mg/m$^2$ of TCN, TCN-P or a related compound can be administered according to a 42 day cycle. In other particular embodiments, 2, 3, 4, 5, 6, 7, 8, 9, 10 or 15 mg/m$^2$ of TCN, TCN-P or a related compound can be administered according to a 42 day cycle. In another particular embodiment, about 1 to about 50 mg of an erlotinib-like compound, for example, gefitinib, erlotinib or a salt thereof is administered. In a particular embodiment, 1, 5, 10, 15, 20, 25, 30, 35, or 40 mg of an erlotinib-like compound, for example, gefitinib, erlotinib or a salt thereof, can be administered according to a 42 day cycle.

In another embodiment, methods are provided to treat cancer in a subject by administering to the subject a dosing regimen of 10 mg/m$^2$ or less of TCN, TCN-P or a related compound and less than about 30 mg of an erlotinib-like compound, for example, gefitinib, erlotinib or a salt thereof, one time per week. In particular embodiments, 0.5, 1, 1.5, 2, 2.5, 3, 3.5, 4, 4.5, 5, 5.5, 6, 6.5, 7, 7.5, 8, 8.5, 9, 9.5 or 10 mg/m$^2$ of TCN, TCN-P or a related compound as disclosed herein can be administered one time per week In another particular embodiment, 1, 5, 10, 15, 20, 25, 30, 35, or 40 mg of an erlotinib-like compound, for example, gefitinib, erlotinib or a salt thereof, can be administered one time per week.

In embodiments of the present invention, the compounds disclosed herein can be administered simultaneously as a single bolus dose over a short period of time, for example, about 5, 10, 15, 20, 30 or 60 minutes. In further embodiments, dosing schedules are provided in which the compounds are administered simultaneously via continuous infusion for at least 24, 48, 72, 96, or 120 hours. In certain embodiments, the administration of the the triciribine compound and/or an erlotinib-like compound, for example, gefitinib, erlotinib or a salt thereof, via continuous or bolus injections can be repeated at a certain frequency at least: once a week, once every two weeks, once every three weeks, once a month, once every five weeks, once every six weeks, once every eight weeks, once every ten weeks and/or once every twelve weeks. The type and frequency of administrations can be combined in any manner disclosed herein to create a dosing cycle. The the triciribine compound and/or an erlotinib-like compound, for example, gefitinib, erlotinib or a salt thereof, can be repeatedly administered via a certain dosing cycles, for example as a bolus injection once every two weeks for three months. The dosing cycles can be administered for at least: one, two three, four five, six, seven, eight, nine, ten, eleven, twelve, eighteen or twenty four months. Alternatively, at least 2, 3, 4, 5, 6, 7, 8, 9, 10, 11, 12, 15 or 20 dosing cycles can be administered to a patient. The triciribine compound and/or an erlotinib-like compound, for example, gefitinib, erlotinib or a salt thereof, can be administered according to any combination disclosed herein, for example, the the triciribine compound and/or an erlotinib-like compound, for example, gefitinib, erlotinib or a salt thereof, can be administered once a week every three weeks for 3 cycles.

In further embodiments, the compounds can be administered separately at least once a day for at least 2, 3, 4, 5, 6, 7, 8, 9 or 10 days. Such administration can be followed by corresponding periods in which the the triciribine compound and/or an erlotinib-like compound, for example, gefitinib, erlotinib or a salt thereof, are not administered The TCN, TCN-P and related compounds and an erlotinib-like compound, for example, gefitinib, erlotinib or a salt thereof, as disclosed herein can be administered to patients in an amount that is effective in causing tumor regression. The administration of TCN, TCN-P or related compounds and an erlotinib-like compound, for example, gefitinib, erlotinib or a salt thereof can provide at least a partial, such as at least 15, 20 or 30%, or complete response in vivo in at least 15-20% of the subjects. In certain embodiments, at least 2, 5, 10, 15, 20, 30 or 50 mg/m$^2$ of a triciribine compound disclosed herein can be administered to a subject. In certain embodiments, at least about 0.5, 1, 1.5, 2, 2.5, 3, 3.5, 4, 4.5, 5, 5.5, 6, 6.5, 7, 7.5, 8, 8.5, 9, 9.5, 10, 12, 15, 17, 20, 25, 30, 35, 40, 45, 50, 55, 60, 65, 70, 75, 80, 85, 90, 95, 100, 150, 165, 175, 200, 250, 300, or 350 mg/m$^2$ of TCN, TCN-P or a related compound disclosed herein can be administered to a subject. In certain embodiments, 1, 5, 10, 15, 20, 25, 30, 35, or 40 mg of an erlotinib-like compound, for example, gefitinib, erlotinib or a salt thereof, can be administered to a subject.

The administration of the compound can be conducted according to any of the therapeutic regimens disclosed herein. In particular embodiments, the dosing regimen includes administering less than about 20 mg/m$^2$ of TCN and related compounds and less than about 30 mg of an erlotinib-like compound, for example, gefitinib, erlotinib or a salt thereof, either concurrently, sequentially, or conducted over a period of time. In one embodiment, less than 20 mg/m$^2$ of TCN or related compounds can be administered once a week concurrently with less than about 30 mg of an erlotinib-like compound, for example, gefitinib, erlotinib or a salt thereof. In another embodiment, less than 20 mg/m$^2$ of TCN or related compounds can be administered once a week and less than about 30 mg of an erlotinib-like compound, for example, gefitinib, erlotinib or a salt thereof can be administered the following week.

In further embodiments, 2 mg/m$^2$, 5 mg/m$^2$, 10 mg/m$^2$, and/or 15 mg/m$^2$ of TCN or a related compound and less than about 300, 250, 200, 150, or 100 mg an erlotinib-like compound, for example, gefitinib, erlotinib or a salt thereof can be administered to a subject. In another embodiment, less than 10 mg/m$^2$ of a triciribine compound and less than about 300 mg of an erlotinib-like compound, for example, gefitinib, erlotinib or a salt thereof can be administered to a subject via continuous infusion for at least five days. The present invention provides for any combination of dosing type, frequency, number of cycles and dosage amount disclosed herein.

5.5. Screening of Patient Populations

In another aspect of the present invention, methods are provided to identify cancers or tumors that are susceptible to the toxic effects of triciribine (TCN) and related compounds. In one embodiment, methods are provided to treat a cancer or tumor in a mammal by (i) obtaining a biological sample from the tumor; (ii) determining whether the cancer or tumor overexpresses Akt kinase or hyperactivated and phosphorylated Akt kinase, and (iii) treating the cancer or tumor with triciribine or a related compound as described herein. In one embodiment, the biological sample can be a biopsy. In other embodiments, the biological sample can be fluid, cells and/or aspirates obtained from the tumor or cancer.

The biological sample can be obtained according to any technique known to one skilled in the art. In one embodiment, a biopsy can be conducted to obtain the biological sample. A biopsy is a procedure performed to remove tissue or cells from the body for examination. Some biopsies can be performed in a physician's office, while others need to be done in a hospital setting. In addition, some biopsies require use of an anesthetic to numb the area, while others do not require any sedation. In certain embodiments, an endoscopic biopsy can be performed. This type of biopsy is performed through a fiberoptic endoscope (a long, thin tube that has a close-focusing telescope on the end for viewing) through a natural body orifice (i.e., rectum) or a small incision (i.e., arthroscopy). The endoscope is used to view the organ in question for abnormal or suspicious areas, in order to obtain a small amount of tissue for study. Endoscopic procedures are named for the organ or body area to be visualized and/or treated. The physician can insert the endoscope into the gastrointestinal tract (alimentary tract endoscopy), bladder (cystoscopy), abdominal cavity (laparoscopy), joint cavity (arthroscopy), mid-portion of the chest (mediastinoscopy), or trachea and bronchial system (laryngoscopy and bronchoscopy).

In another embodiment, a bone marrow biopsy can be performed. This type of biopsy can be performed either from the sternum (breastbone) or the iliac crest hipbone (the bone area on either side of the pelvis on the lower back area). The skin is cleansed and a local anesthetic is given to numb the area. A long, rigid needle is inserted into the marrow, and cells are aspirated for study; this step is occasionally uncomfortable. A core biopsy (removing a small bone 'chip' from the marrow) may follow the aspiration.

In a further embodiment, an excisional or incisional biopsy can be performed on the mammal. This type of biopsy is often used when a wider or deeper portion of the skin is needed. Using a scalpel (surgical knife), a full thickness of skin is removed for further examination, and the wound is sutured (sewed shut with surgical thread). When the entire tumor is removed, it is referred to as an excisional biopsy technique. If only a portion of the tumor is removed, it is referred to as an incisional biopsy technique. Excisional biopsy is often the method usually preferred, for example, when melanoma (a type of skin cancer) is suspected.

In still further embodiments, a fine needle aspiration (FNA) biopsy can be used. This type of biopsy involves using a thin needle to remove very small pieces from a tumor. Local anesthetic is sometimes used to numb the area, but the test rarely causes much discomfort and leaves no scar. FNA is not, for example, used for diagnosis of a suspicious mole, but may be used, for example, to biopsy large lymph nodes near a melanoma to see if the melanoma has metastasized (spread). A computed tomography scan (CT or CAT scan) can be used to guide a needle into a tumor in an internal organ such as the lung or liver.

In other embodiments, punch shave and/or skin biopsies can be conducted. Punch biopsies involve taking a deeper sample of skin with a biopsy instrument that removes a short cylinder, or "apple core," of tissue. After a local anesthetic is administered, the instrument is rotated on the surface of the skin until it cuts through all the layers, including the dermis, epidermis, and the most superficial parts of the subcutis (fat). A shave biopsy involves removing the top layers of skin by shaving it off. Shave biopsies are also performed with a local anesthetic. Skin biopsies involve removing a sample of skin for examination under the microscope to determine if, for example, melanoma is present. The biopsy is performed under local anesthesia.

In particular embodiment, methods are provided to determine whether the tumor overexpresses an Akt kinase. Akt kinase overexpression can refer to the phosphorylation state of the kinase. Hyperphosphorylation of Akt can be detected according to the methods described herein. In one embodiment, a tumor biopsy can be compared to a control tissue. The control tissue can be a normal tissue from the mammal in which the biopsy was obtained or a normal tissue from a healthy mammal. Akt kinase overexpression or hyperphosphorylation can be determined if the tumor biopsy contains greater amounts of Akt kinase and/or Akt kinase phosphorylation than the control tissue, such as, for example, at least approximately 1.5, 2, 2.25, 2.5, 2.75, 3, 3.25, 3.5, 3.75, 4, 4.25, 4.5, 4.75, 5, 5.5, 6, 7, 8, 9, or 10-fold greater amounts of Akt kinase than contained in the control tissue.

In one embodiment, the present invention provides a method to detect aberrant Akt kinase expression in a subject or in a biological sample from the subject by contacting cells, cell extracts, serum or other sample from the subjects or said biological sample with an immunointeractive molecule specific for an Akt kinase or antigenic portion thereof and screening for the level of immunointeractive molecule-Akt kinase complex formation, wherein an elevated presence of the complex relative to a normal cell is indicative of an aberrant cell that expresses or overexpresses Akt. In one example, cells or cell extracts can be screened immunologically for the presence of elevated levels of Akt kinase.

In an alternative embodiment, the aberrant expression of Akt in a cell is detected at the genetic level by screening for the level of expression of a gene encoding an Akt kinase wherein an elevated level of a transcriptional expression product (i.e., mRNA) compared to a normal cell is indicative of an aberrant cell. In certain embodiments, real-time PCR as well as other PCR procedures can be used to determine transcriptional activity. In one embodiment, mRNA can be obtained from cells of a subject or from a biological sample from a subject and cDNA optionally generated. The mRNA or cDNA can then be contacted with a genetic probe capable of hybridizing to and/or amplifying all or part of a nucleotide sequence encoding Akt kinase or its complementary nucleotide sequence and then the level of the mRNA or cDNA can be detected wherein the presence of elevated levels of the mRNA or cDNA compared to normal controls can be assessed.

Yet another embodiment of the present invention contemplates the use of an antibody, monoclonal or polyclonal, to Akt kinase in a quantitative or semi-quantitative diagnostic kit to determine relative levels of Akt kinase in suspected cancer cells from a patient, which can include all the reagents necessary to perform the assay. In one embodiment, a kit utilizing reagents and materials necessary to perform an ELISA assay is provided. Reagents can include, for example, washing buffer, antibody dilution buffer, blocking buffer, cell staining solution, developing solution, stop solution, anti-phospho-protein specific antibodies, anti-Pan protein specific antibodies, secondary antibodies, and distilled water. The kit can also include instructions for use and can optionally be automated or semi-automated or in a form which is compatible with automated machine or software. In one embodiment, a phosphor-ser-473 Akt antibody that detects the activated form of AKT (Akt phosphorylated at serine 474) can be utilized as the antibody in a diagnostic kit. See, for example, Yuan et al., Oncogene, 2000. 19: p. 2324-2330.

5.6. Akt Kinases

Akt, also named $PKB^3$, represents a subfamily of the serine/threonine kinase. Three members, AKT1, AKT2, and AKT3, have been identified in this subfamily. Akt is activated by extracellular stimuli in a PI3K-dependent manner (Datta S. R. et al., Genes Dev, 1999. 13: p. 2905-2927). Full activation of Akt requires phosphorylation of $Thr^{308}$ in the activation loop and $Ser^{473}$ in the C-terminal activation domain. Akt is negatively regulated by PTEN tumor suppressor. Mutations in PTEN have been identified in various tumors, which lead to activation of Akt pathway (Datta S. R. et al., Genes Dev, 1999. 13: p. 2905-2927). In addition, amplification, overexpression and/or activation of Akt have been detected in a number of human malignancies (Datta S. R. et al., Genes Dev, 1999. 13: p. 2905-2927); Cheng J. Q. and Nicosia S. V., in *Encyclopedic Reference of Cancer*, 2001, Schwab D. (ed.) Springer, Berlin Heidelberg and New York: pp 35-7). Ectopic expression of Akt, especially constitutively active Akt, induces cell survival and malignant transformation whereas inhibition of Akt activity stimulates apoptosis in a range of mammalian cells (Datta S. R. et al., Genes Dev, 1999. 13: p. 2905-2927); Cheng J. Q. and Nicosia S. V., in *Encyclopedic Reference of Cancer*, 2001, Schwab D. (ed.) Springer, Berlin Heidelberg and New York: pp 35-7; Sun M. et al., Am J Path, 2001. 159: p. 431-437; Cheng J. Q. et al., Oncogene, 1997. 14: p. 2793-2801). Further, activation of Akt has been shown to associate with tumor invasiveness and chemoresistance (West K. A. et al., Drug Resist Updat, 2002. 5: p. 234-248).

Activation of the Akt pathway plays a pivotal role in malignant transformation and chemoresistance by inducing cell survival, growth, migration, and angiogenesis. The present invention provides methods to determine levels of Akt kinase overexpression and/or hyperactivated and phosphorylated Akt kinase.

The Akt kinase can be any known Akt family kinase, or kinase related thereto, including, but not limited to Akt 1, Akt 2, Akt 3. The mRNA and amino acid sequences of human Akt1, Akt2, and Akt 3 are illustrated in FIGS. 6a-c, 7a-d, and 8a-c, respectively.

5.7. Diagnostic Assays

Immunological Assays

In one embodiment, a method is provided for detecting the aberrant expression of an Akt kinase in a cell in a mammal or in a biological sample from the mammal, by contacting cells, cell extracts or serum or other sample from the mammal or biological sample with an immunointeractive molecule specific for an Akt kinase or antigenic portion thereof and screening for the level of immunointeractive molecule-Akt kinase complex formations and determining whether an elevated presence of the complex relative to a normal cell is present.

The immunointeractive molecule can be a molecule having specificity and binding affinity for an Akt kinase or its antigenic parts or its homologs or derivatives thereof. In one embodiment, the immunointeractive molecule can be an immunglobulin molecule. In other embodiments, the immunointeractive molecules can be an antibody fragments, single chain antibodies, and/or deimmunized molecules including humanized antibodies and T-cell associated antigen-binding molecules (TABMs). In one particular embodiment, the antibody can be a monoclonal antibody. In another particular embodiment, the antibody can be a polyclonal antibody. The immunointeractive molecule can exhibit specificity for an Akt kinase or more particularly an antigenic determinant or epitope on an Akt kinase. An antigenic determinant or epitope on an Akt kinase includes that part of the molecule to which an immune response is directed. The antigenic determinant or epitope can be a B-cell epitope or where appropriate a T-cell epitope. In one embodiment, the antibody is a phosphor-ser 473 Akt antibody.

One embodiment of the present invention provides a method for diagnosing the presence of cancer or cancer-like growth in a mammal, in which aberrant Akt activity is present, by contacting cells or cell extracts from the mammal or a biological sample from the subject with an Akt kinase-binding-effective amount of an antibody having specificity for the Akt kinase or an antigenic determinant or epitope thereon and then quantitatively or qualitatively determining the level of an Akt kinase-antibody complex wherein the presence of elevated levels of said complex compared to a normal cell is determined.

Antibodies can be prepared by any of a number of means known to one skilled in the art. For example, for the detection of human Akt kinase, antibodies can be generally but not necessarily derived from non-human animals such as primates, livestock animals (e.g. sheep, cows, pigs, goats, horses), laboratory test animals (e.g. mice, rats, guinea pigs, rabbits) and/or companion animals (e.g. dogs, cats). Antibodies may also be recombinantly produced in prokaryotic or eukaryotic host cells. Generally, antibody based assays can be conducted in vitro on cell or tissue biopsies. However, if an antibody is suitably deimmunized or, in the case of human use, humanized, then the antibody can be labeled with, for example, a nuclear tag, administered to a patient and the site of nuclear label accumulation determined by radiological techniques. The Akt kinase antibody can be a cancer targeting agent. Accordingly, another embodiment of the present invention provides deimmunized forms of the antibodies for use in cancer imaging in human and non-human patients.

In general, for the generation of antibodies to an Akt kinase, the enzyme is required to be extracted from a biological sample whether this be from animal including human tissue or from cell culture if produced by recombinant means. The Akt kinase can be separated from the biological sample by any suitable means. For example, the separation may take advantage of any one or more of the Akt kinase's surface charge properties, size, density, biological activity and its affinity for another entity (e.g. another protein or chemical compound to which it binds or otherwise associates). Thus, for example, separation of the Akt kinase from the biological fluid can be achieved by any one or more of ultra-centrifugation, ion-exchange chromatography (e.g. anion exchange chromatography, cation exchange chromatography), electrophoresis (e.g. polyacrylamide gel electrophoresis, isoelectric focussing), size separation (e.g., gel filtration, ultra-filtration) and affinity-mediated separation (e.g. immunoaffinity separation including, but not limited to, magnetic bead separation such as Dynabead (trademark) separation, immunochromatography, immuno-precipitation). The separation of Akt kinase from the biological fluid can preserve conformational epitopes present on the kinase and, thus, suitably avoids techniques that cause denaturation of the enzyme. In a further embodiment, the kinase can be separated from the biological fluid using any one or more of affinity separation, gel filtration and/or ultra-filtration.

Immunization and subsequent production of monoclonal antibodies can be carried out using standard protocols known in the art, such as, for example, described by Kohler and Milstein (Kohler and Milstein, Nature, 1975. 256: p. 495-499; Kohler and Milstein, Eur J Immunol, 1976. 6(7): p. 511-519; Coligan et al., (Current Protocols in Immunology, 1991-1997, John Wiley & Sons, Inc.) or Toyama et al. (Monoclonal Antibody, Experiment Manual, 1987, Kodansha Scientific). Essentially, an animal is immunized with an Akt kinase-containing biological fluid or fraction thereof or a recombinant form of Akt kinase by standard methods to produce antibody-producing cells, particularly antibody-producing somatic cells (e.g. B lymphocytes). These cells can then be removed from the immunized animal for immortalization. In certain embodiment, a fragment of an Akt kinase can be used to the generate antibodies. The fragment can be associated with a carrier. The carrier can be any substance of typically high molecular weight to which a non- or poorly immunogenic substance (e.g. a hapten) is naturally or artificially linked to enhance its immunogenicity.

Immortalization of antibody-producing cells can be carried out using methods which are well-known in the art. For example, the immortalization may be achieved by the transformation method using Epstein-Barr virus (EBV) (Kozbor et al., Methods in Enzymology, 1986. 121: p. 140). In another embodiment, antibody-producing cells are immortalized using the cell fusion method (described in Coligan et al., 1991-1997, supra), which is widely employed for the production of monoclonal antibodies. In this method, somatic antibody-producing cells with the potential to produce antibodies, particularly B cells, are fused with a myeloma cell line. These somatic cells may be derived from the lymph nodes, spleens and peripheral blood of primed animals, preferably rodent animals such as mice and rats. In a particular embodiment, mice spleen cells can be used. In other embodiments, rat, rabbit, sheep or goat cells can also be used. Specialized myeloma cell lines have been developed from lymphocytic tumours for use in hybridoma-producing fusion procedures (Kohler and Milstein, 1976, supra; Shulman et al., Nature, 1978. 276: p. 269-270; Volk et al., J Virol, 1982. 42(1): p. 220-227). Many myeloma cell lines can also be used for the production of fused cell hybrids, including, e.g. P3.times.63-Ag8, P3.times.63-AG8.653, P3/NS1-Ag4-1 (NS-1), Sp2/0-Ag14 and S194/5.XXO.Bu.1. The P3.times.63-Ag8 and NS-1 cell lines have been described by Kohler and Milstein (1976, supra). Shulman et al. (1978, supra) developed the Sp2/0-Ag14 myeloma line. The S194/5.XXO.Bu.1 line was reported by Trowbridge (J Exp Med, 1978. 148(1): p. 313-323). Methods for generating hybrids of antibody-producing spleen or lymph node cells and myeloma cells usually involve mixing somatic cells with myeloma cells in a 10:1 proportion (although the proportion may vary from about 20:1 to about 1:1), respectively, in the presence of an agent or agents (chemical, viral or electrical) that promotes the fusion of cell membranes. Fusion methods have been described (Kohler and Milstein, 1975, supra; Kohler and Milstein, 1976, supra; Gefter et al., Somatic Cell Genet, 1977. 3: p. 231-236; Volk et al., 1982, supra). The fusion-promoting agents used by those investigators were Sendai virus and polyethylene glycol (PEG). In certain embodiments, means to select the fused cell hybrids from the remaining unfused cells, particularly the unfused myeloma cells, are provided. Generally, the selection of fused cell hybrids can be accomplished by culturing the cells in media that support the growth of hybridomas but prevent the growth of the unfused myeloma cells, which normally would go on dividing indefinitely. The somatic cells used in the fusion do not maintain long-term viability in in vitro culture and hence do not pose a problem. Several weeks are required to selectively culture the fused cell hybrids. Early in this time period, it is necessary to identify those hybrids which produce the desired antibody, so that they may subsequently be cloned and propagated. Generally, around 10% of the hybrids obtained produce the desired antibody, although a range of from about 1 to about 30% is not uncommon. The detection of antibody-producing hybrids can be achieved by any one of several standard assay methods, including enzyme-linked immunoassay and radioimmunoassay techniques as, for example, described in Kennet et al. (Monoclonal Antibodies and Hybridomas: A New Dimension in Biological Analyses, 1980, Plenum Press, New York, p. 376-384) and by FACS analysis (O'Reilly et al., Biotechniques, 1998 25: p. 824-830).

Once the desired fused cell hybrids have been selected and cloned into individual antibody-producing cell lines, each cell line may be propagated in either of two standard ways. A suspension of the hybridoma cells can be injected into a histocompatible animal. The injected animal will then develop tumours that secrete the specific monoclonal antibody produced by the fused cell hybrid. The body fluids of the animal, such as serum or ascites fluid, can be tapped to provide monoclonal antibodies in high concentration. Alternatively, the individual cell lines may be propagated in vitro in laboratory culture vessels. The culture medium containing high concentrations of a single specific monoclonal antibody can be harvested by decantation, filtration or centrifugation, and subsequently purified.

The cell lines can then be tested for their specificity to detect the Akt kinase of interest by any suitable immuno-detection means. For example, cell lines can be aliquoted into a number of wells and incubated and the supernatant from each well is analyzed by enzyme-linked immunosorbent assay (ELISA), indirect fluorescent antibody technique, or the like. The cell line(s) producing a monoclonal antibody capable of recognizing the target LIM kinase but which does not recognize non-target epitopes are identified and then directly cultured in vitro or injected into a histocompatible animal to form tumours and to produce, collect and purify the required antibodies.

The present invention provides, therefore, a method of detecting in a sample an Akt kinase or fragment, variant or derivative thereof comprising contacting the sample with an antibody or fragment or derivative thereof and detecting the level of a complex containing the antibody and Akt kinase or fragment, variant or derivative thereof compared to normal controls wherein elevated levels of Akt kinase is determined. Any suitable technique for determining formation of the complex may be used. For example, an antibody according to the invention, having a reporter molecule associated therewith, may be utilized in immunoassays. Such immunoassays include but are not limited to radioimmunoassays (RIAs), enzyme-linked immunosorbent assays (ELISAs) immunochromatographic techniques (ICTs), and Western blotting which are well known to those of skill in the art. Immunoassays can also include competitive assays. The present invention encompasses qualitative and quantitative immunoassays.

Suitable immunoassay techniques are described, for example, in U.S. Pat. Nos. 4,016,043; 4,424,279; and 4,018,653. These include both single-site and two-site assays of the non-competitive types, as well as the traditional competitive binding assays. These assays also include direct binding of a labeled antigen-binding molecule to a target antigen.

The invention further provides methods for quantifying Akt protein expression and activation levels in cells or tissue samples obtained from an animal, such as a human cancer patient or an individual suspected of having cancer. In one embodiment, the invention provides methods for quantifying Akt protein expression or activation levels using an imaging system quantitatively. The imaging system can be used to receive, enhance, and process images of cells or tissue samples, that have been stained with AKT protein-specific stains, in order to determine the amount or activation level of AKT protein expressed in the cells or tissue samples from such an animal. In embodiments of the methods of the invention, a calibration curve of AKT1 and AKT2 protein expression can be generated for at least two cell lines expressing differing amounts of AKT protein. The calibration curve can then used to quantitatively determine the amount of AKT protein that is expressed in a cell or tissue sample. Analogous calibration curves can be made for activated AKT proteins using reagents specific for the activation features. It can also be used to determine changes in amounts and activation state of AKT before and after clinical cancer treatment.

In one particular embodiment of the methods of the invention, AKT protein expression in a cell or tissue sample can be quantified using an enzyme-linked immunoabsorbent assay (ELISA) to determine the amount of AKT protein in a sample. Such methods are described, for example, in U.S. Patent Publication No. 2002/0015974.

In other embodiments enzyme immunoassays can be used to detect the Akt kinase. In such assays, an enzyme is conjugated to the second antibody, generally by means of glutaraldehyde or periodate. The substrates to be used with the specific enzymes are generally chosen for the production of, upon hydrolysis by the corresponding enzyme, a detectable colour change. It is also possible to employ fluorogenic substrates, which yield a fluorescent product rather than the chromogenic substrates. The enzyme-labeled antibody can be added to the first antibody-antigen complex, allowed to bind, and then the excess reagent washed away. A solution containing the appropriate substrate can then be added to the complex of antibody-antigen-antibody. The substrate can react with the enzyme linked to the second antibody, giving a qualitative visual signal, which may be further quantitated, usually spectrophotometrically, to give an indication of the amount of antigen which was present in the sample. Alternately, fluorescent compounds, such as fluorescein, rhodamine and the lanthanide, europium (EU), can be chemically coupled to antibodies without altering their binding capacity. When activated by illumination with light of a particular wavelength, the fluorochrome-labeled antibody adsorbs the light energy, inducing a state to excitability in the molecule, followed by emission of the light at a characteristic colour visually detectable with a light microscope. The fluorescent-labeled antibody is allowed to bind to the first antibody-antigen complex. After washing off the unbound reagent, the remaining tertiary complex is then exposed to light of an appropriate wavelength. The fluorescence observed indicates the presence of the antigen of interest. Immunofluorometric assays (IFMA) are well established in the art and are particularly useful for the present method. However, other reporter molecules, such as radioisotope, chemiluminescent or bioluminescent molecules can also be employed.

In a particular embodiment, antibodies to Akt kinase can also be used in ELISA-mediated detection of Akt kinase especially in serum or other circulatory fluid. This can be accomplished by immobilizing anti-Akt kinase antibodies to a solid support and contacting these with a biological extract such as serum, blood, lymph or other bodily fluid, cell extract or cell biopsy. Labeled anti-Akt kinase antibodies can then be used to detect immobilized Akt kinase. This assay can be varied in any number of ways and all variations are encompassed by the present invention and known to one skilled in the art. This approach can enable rapid detection and quantitation of Akt kinase levels using, for example, a serum-based assay.

In one embodiment, an Akt ELISA assay kit may be used in the present invention. For example, a Cellular Activation of Signaling ELISA kit for Akt S473 from SuperArray Bioscience can be utilized in the present invention. In one embodiment, the antibody can be an anti-pan antibody that recognizes Akt S473. ELISA assay kit containing an anti-Akt antibody and additional reagents, including, but not limited to, washing buffer, antibody dilution buffer, blocking buffer, cell staining solution, developing solution, stop solution, secondary antibodies, and distilled water.

Nucleotide Detection

In another embodiment, a method to detect Akt kinases is provided by detecting the level of expression in a cell of a polynucleotide encoding an Akt kinase. Expression of the polynucleotide can be determined using any suitable technique known to one skilled in the art. In one embodiment, a labeled polynucleotide encoding an Akt kinase can be utilized as a probe in a Northern blot of an RNA extract obtained from the cell. In other embodiments, a nucleic acid extract from an animal can be utilized in concert with oligonucleotide primers corresponding to sense and antisense sequences of a polynucleotide encoding the kinase, or flanking sequences thereof; in a nucleic acid amplification reaction such as RT PCR. A variety of automated solid-phase detection techniques are also available to one skilled in the art, for example, as described by Fodor et al. (Science, 1991. 251: p. 767-777) and Kazal et al. (Nature Medicine, 1996. 2: p. 753-759).

In other embodiments, methods are provided to detect Akt kinase encoding RNA transcripts. The RNA can be isolated from a cellular sample suspected of containing Akt kinase RNA, e.g. total RNA isolated from human cancer tissue. RNA can be isolated by methods known in the art, e.g. using TRIZOL reagent (GIBCO-BRL/Life Technologies, Gaithersburg, Md.). Oligo-dT, or random-sequence oligonucleotides, as well as sequence-specific oligonucleotides can be employed as a primer in a reverse transcriptase reaction to prepare first-strand cDNAs from the isolated RNA. Resultant first-strand cDNAs can then amplified with sequence-specific oligonucleotides in PCR reactions to yield an amplified product.

Polymerase chain reaction or "PCR" refers to a procedure or technique in which amounts of a preselected fragment of nucleic acid, RNA and/or DNA, are amplified as described, for example, in U.S. Pat. No. 4,683,195. Generally, sequence information from the ends of the region of interest or beyond is employed to design oligonucleotide primers. These primers will be identical or similar in sequence to opposite strands of the template to be amplified. PCR can be used to amplify specific RNA sequences and cDNA transcribed from total cellular RNA. See generally Mullis et al. (Quant Biol, 1987. 51: p. 263; Erlich, eds., PCR Technology, 1989, Stockton Press, NY). Thus, amplification of specific nucleic acid sequences by PCR relies upon oligonucleotides or "primers" having conserved nucleotide sequences wherein the conserved sequences are deduced from alignments of related gene or protein sequences, e.g. a sequence comparison of mammalian Akt kinase genes. For example, one primer is prepared which is predicted to anneal to the antisense strand and another primer prepared which is predicted to anneal to the sense strand of a cDNA molecule which encodes a Akt kinase. To detect the amplified product, the reaction mixture is typically subjected to agarose gel electrophoresis or other convenient separation technique and the relative presence of the Akt kinase specific amplified DNA detected. For example, Akt kinase amplified DNA may be detected using Southern hybridization with a specific oligonucleotide probe or comparing its electrophoretic mobility with DNA standards of known molecular weight. Isolation, purification and characterization of the amplified Akt kinase DNA can be accomplished by excising or eluting the fragment from the gel (for example, see references Lawn et al., Nucleic Acids Res, 1981. 2: p. 6103; Goeddel et al., Nucleic Acids Res, 1980. 8: p. 4057), cloning the amplified product into a cloning site of a suitable vector, such as the pCRII vector (Invitrogen), sequencing the cloned insert and comparing the DNA sequence to the known sequence of LIM kinase. The relative amounts of LIM kinase mRNA and cDNA can then be determined.

In one embodiment, real-time PCR can be used to determine transcriptional levels of Akt nucleotides. Determination of transcriptional activity also includes a measure of potential translational activity based on available mRNA transcripts. Real-time PCR as well as other PCR procedures use a number of chemistries for detection of PCR product including the binding of DNA binding fluorophores, the 5' endonuclease, adjacent liner and hairpin oligoprobes and the self-fluorescing amplicons. These chemistries and real-time PCR in general are discussed, for example, in Mackay et al., Nucleic Acids Res, 2002. 30(6): p. 1292-1305; Walker, J Biochem Mol Toxicology, 2001. 15(3): p. 121-127; Lewis et al., J Pathol, 2001. 195: p. 66-71.

In an alternate embodiment, the aberrant expression of Akt can be identified by contacting a nucleotide sequences isolated from a biological sample with an oligonucleotide probe having a sequence complementary to an Akt sequences selected from the nucleotide sequences of FIG. 6a-c, 7a-d, or 8a-c, or fragment thereof, and then detecting the sequence by hybridizing the probe to the sequence, and comparing the results to a normal sample. The hybridization of the probe to the biological sample can be detected by labeling the probe using any detectable agent. The probe can be labeled for example, with a radioisotope, or with biotin, fluorescent dye, electron-dense reagent, enzyme, hapten or protein for which antibodies are available. The detectable label can be assayed by any desired means, including spectroscopic, photochemical, biochemical, immunochemical, radioisotopic, or chemical means. The probe can also be detected using techniques such as an oligomer restriction technique, a dot blot assay, a reverse dot blot assay, a line probe assay, and a 5' nuclease assay. Alternatively, the probe can be detected using any of the generally applicable DNA array technologies, including macroarray, microarray and DNA microchip technologies. The oligonucleotide probe typically includes approximately at least 14, 15, 16, 18, 20, 25 or 28 nucleotides that hybridize to the nucleotides selected from FIGS. 6a-c, 7a-d, and 8a-c, or a fragment thereof. It is generally not preferred to use a probe that is greater than approximately 25 or 28 nucleotides in length. The oligonucleotide probe is designed to identify an Akt nucleotide sequence.

Kinase Assays

The activity of the Akt kinases can be measured using any suitable kinase assay known in the art. For example, and not by way of limitation, the methods described in Hogg et al (Oncogene, 1994. 9: p. 98-96), Mills et al (J Biol Chem, 1992. 267: p. 16000-006) and Tomizawa et al. (FEBS Lett, 2001. 492: p. 221-7), Schmandt et al. (J Immunol, 1994. 152: p. 96-105) can be used. Further serine, threonine and tyrosine kinase assays are described in Ausubel et al. (Short Protocols in Molecular Biology, 1999, unit 17.6).

Akt kinase assays can generally use an Akt polypeptide, a labeled donor substrate, and a receptor substrate that is either specific or non-specific for Akt. In such assays Akt transfers a labeled moiety from the donor substrate to the receptor substrate, and kinase activity is measured by the amount of labeled moiety transferred from the donor substrate to the receptor substrate. Akt polypeptide can be produced using various expression systems, can be purified from cells, can be in the form of a cleaved or uncleaved recombinant fusion protein and/or can have non-Akt polypeptide sequences, for example a His tag or .beta.-galactosidase at its N- or C-terminus. Akt activity can be assayed in cancerous cells lines if the cancerous cell lines are used as a source of the Akt to be assayed. Suitable donor substrates for Akt assays include any molecule that is susceptible to dephosphorylation by Akt, such as, for example include .gamma.-labeled ATP and ATP analogs, wherein the label is $^{33}P$, $^{32}P$, $^{35}S$ or any other radioactive isotope or a suitable fluorescent marker. Suitable recipient substrates for Akt assays include any polypeptide or other molecule that is susceptible to phosphorylation by Akt. Recipient substrates can be derived from fragments of in vivo targets of Akt. Recipient substrates fragments can be 8 to 50 amino acids in length, usually 10 to 30 amino acids and particularly of about 10, 12, 15, 18, 20 and 25 amino acids in length. Further recipient substrates can be determined empirically using a set of different polypeptides or other molecules. Targets of Recipient substrates for TTK can be capable of being purified from other components of the reaction once the reaction has been performed. This purification is usually done through a molecular interaction, where the recipient substrates is biotinylated and purified through its interaction with streptavidin, or a specific antibody is available that can specifically recognize the recipient substrates. The reaction can be performed in a variety of conditions, such as on a solid support, in a gel, in solution or in living cells. The choice of detection methods depends on type of label used for the donor molecule and may include, for example, measurement of incorporated radiation or fluorescence by autoradiography, scintillation, scanning or fluorography.

6. METHODS OF TREATMENT

The compounds and pharmaceutical compositions provided herein can be used in the treatment of a condition including tumors, cancer, and other disorders associated with abnormal cell proliferation. In one embodiment, the compounds of the present invention can be used to treat a carcinoma, sarcoma, lymphoma, leukemia, and/or myeloma. In other embodiments of the present invention, the compounds disclosed herein can be used to treat solid tumors.

The compounds of the present invention invention can be used for the treatment of cancer, such as, but not limited to, cancer of the following organs or tissues: breast, prostate, lung, bronchus, colon, urinary, bladder, non-Hodgkin lymphoma, melanoma, kidney, renal, pancreas, pharnx, thyroid, stomach, brain, multiple myeloma, esophagus, liver, intrahepatic bile duct, cervix, larynx, acute myeloid leukemia, chronic lymphatic leukemia, soft tissue, such as heart, Hodgkin lymphoma, testis, small intestine, chronic myeloid leukemia, acute lymphatic leukemia, anus, anal canal, anorectal, thyroid, vulva, gallbladder, pleura, eye, nose nasal cavity, middle ear, nasopharnx, ureter, peritoneum, omentum, mesentery, and gastrointestineal, high grade glioma, glioblastoma, colon, rectal, pancreatic, gastric cancers, hepatocellular carcinoma; head and neck cancers, carcinomas; renal cell carcinoma; adenocarcinoma; sarcomas; hemangioendothelioma; lymphomas; leukemias, mycosis fungoides. In additional embodiments, the compounds of the present invention can be used to treat skin diseases including, but not limited to, the malignant diseases angiosarcoma, hemangioendothelioma, basal cell carcinoma, squamous cell carcinoma, malignant melanoma and Kaposi's sarcoma, and the non-malignant diseases or conditions such as psoriasis, lymphangiogenesis, hemangioma of childhood, Sturge-Weber syndrome, verruca vulgaris, neurofibromatosis, tuberous sclerosis, pyogenic granulomas, recessive dystrophic epidermolysis bullosa, venous ulcers, acne, rosacea, eczema, molluscum contagious, seborrheic keratosis, and actinic keratosis.

Compositions including the compounds of the invention can be used to treat these cancers and other cancers at any stage from the discovery of the cancer to advanced stages. In addition, compositions including compounds of the invention can be used in the treatment of the primary cancer and metastases thereof.

In other embodiments of the invention, the compounds described herein can be used for the treatment of cancer, including, but not limited to the cancers listed in Table 2 below.

TABLE 2

| Types of Cancer | |
| --- | --- |
| Acute Lymphoblastic Leukemia, Adult | Hairy Cell Leukemia |
| Acute Lymphoblastic Leukemia, Childhood | Head and Neck Cancer |
| | Hepatocellular (Liver) Cancer, Adult (Primary) |
| Acute Myeloid Leukemia, Adult | |
| Acute Myeloid Leukemia, Childhood | Hepatocellular (Liver) Cancer, Childhood (Primary) |
| Adrenocortical Carcinoma | |
| Adrenocortical Carcinoma, Childhood | Hodgkin's Lymphoma, Adult |
| AIDS-Related Cancers | Hodgkin's Lymphoma, Childhood |
| AIDS-Related Lymphoma | Hodgkin's Lymphoma During Pregnancy |
| Anal Cancer | Hypopharyngeal Cancer |
| Astrocytoma, Childhood Cerebellar | Hypothalamic and Visual Pathway Glioma, Childhood |
| Astrocytoma, Childhood Cerebral | |
| Basal Cell Carcinoma | Intraocular Melanoma |
| Bile Duct Cancer, Extrahepatic | Islet Cell Carcinoma (Endocrine Pancreas) |
| Bladder Cancer | Kaposi's Sarcoma |
| Bladder Cancer, Childhood | Kidney (Renal Cell) Cancer |
| Bone Cancer, Osteosarcoma/Malignant Fibrous Histiocytoma | Kidney Cancer, Childhood |
| | Laryngeal Cancer |
| Brain Stem Glioma, Childhood | Laryngeal Cancer, Childhood |
| Brain Tumor, Adult | Leukemia, Acute Lymphoblastic, Adult |
| Brain Tumor, Brain Stem Glioma, Childhood | Leukemia, Acute Lymphoblastic, Childhood |
| | Leukemia, Acute Myeloid, Adult |
| Brain Tumor, Cerebellar Astrocytoma, Childhood | Leukemia, Acute Myeloid, Childhood |
| | Leukemia, Chronic Lymphocytic |
| Brain Tumor, Cerebral Astrocytoma/Malignant Glioma, Childhood | Leukemia, Chronic Myelogenous |
| | Leukemia, B Cell |
| | Lip and Oral Cavity Cancer |
| Brain Tumor, Ependymoma, Childhood | Liver Cancer, Adult (Primary) |
| Brain Tumor, Medulloblastoma, Childhood | Liver Cancer, Childhood (Primary) |
| | Lung Cancer, Non-Small Cell |
| Brain Tumor, Supratentorial Primitive Neuroectodermal Tumors, Childhood | Lung Cancer, Small Cell |
| | Lymphoma, AIDS-Related |
| Brain Tumor, Visual Pathway and Hypothalamic Glioma, Childhood | Lymphoma, Burkitt's |
| | Lymphoma, Cutaneous T-Cell, see Mycosis Fungoides and Sézary Syndrome |
| Brain Tumor, Childhood | |
| Breast Cancer | Lymphoma, Hodgkin's, Adult |
| Breast Cancer, Childhood | Lymphoma, Hodgkin's, Childhood |
| Breast Cancer, Male | Lymphoma, Hodgkin's During Pregnancy |
| Bronchial Adenomas/Carcinoids, Childhood | Lymphoma, Non-Hodgkin's, Adult |
| | Lymphoma, Non-Hodgkin's, Childhood |

TABLE 2-continued

| Types of Cancer |
| --- |

Burkitt's Lymphoma
Carcinoid Tumor, Childhood
Carcinoid Tumor, Gastrointestinal
Carcinoma of Unknown Primary
Central Nervous System Lymphoma, Primary
Cerebellar Astrocytoma, Childhood
Cerebral Astrocytoma/Malignant Glioma, Childhood
Cervical Cancer
Childhood Cancers
Chronic Lymphocytic Leukemia
Chronic Myelogenous Leukemia
Chronic Myeloproliferative Disorders
Colon Cancer
Colorectal Cancer, Childhood
Cutaneous T-Cell Lymphoma, see Mycosis Fungoides and Sézary Syndrome
Endometrial Cancer
Ependymoma, Childhood
Esophageal Cancer
Esophageal Cancer, Childhood
Ewing's Family of Tumors
Extracranial Germ Cell Tumor, Childhood
Extragonadal Germ Cell Tumor
Extrahepatic Bile Duct Cancer
Eye Cancer, Intraocular Melanoma
Eye Cancer, Retinoblastoma
Gallbladder Cancer
Gastric (Stomach) Cancer
Gastric (Stomach) Cancer, Childhood
Gastrointestinal Carcinoid Tumor
Germ Cell Tumor, Extracranial, Childhood
Germ Cell Tumor, Extragonadal
Germ Cell Tumor, Ovarian
Gestational Trophoblastic Tumor
Glioma, Adult
Glioma, Childhood Brain Stem
Glioma, Childhood Cerebral Astrocytoma
Glioma, Childhood Visual Pathway and Hypothalamic
Skin Cancer (Melanoma)
Skin Carcinoma, Merkel Cell
Small Cell Lung Cancer
Small Intestine Cancer
Soft Tissue Sarcoma, Adult
Soft Tissue Sarcoma, Childhood
Squamous Cell Carcinoma, see Skin Cancer (non-Melanoma)
Squamous Neck Cancer with Occult Primary, Metastatic
Stomach (Gastric) Cancer
Stomach (Gastric) Cancer, Childhood
Supratentorial Primitive Neuroectodermal Tumors, Childhood
T-Cell Lymphoma, Cutaneous, see Mycosis Fungoides and Sézary Syndrome
Testicular Cancer
Thymoma, Childhood
Thymoma and Thymic Carcinoma
Thyroid Cancer
Thyroid Cancer, Childhood
Transitional Cell Cancer of the Renal Pelvis and Ureter
Trophoblastic Tumor, Gestational
Unknown Primary Site, Carcinoma of, Adult
Unknown Primary Site, Cancer of, Childhood
Unusual Cancers of Childhood
Ureter and Renal Pelvis, Transitional Cell Cancer
Urethral Cancer
Lymphoma, Non-Hodgkin's During Pregnancy
Lymphoma, Primary Central Nervous System
Macroglobulinemia, Waldenström's
Malignant Fibrous Histiocytoma of Bone/Osteosarcoma
Medulloblastoma, Childhood
Melanoma
Melanoma, Intraocular (Eye)
Merkel Cell Carcinoma
Mesothelioma, Adult Malignant
Mesothelioma, Childhood
Metastatic Squamous Neck Cancer with Occult Primary
Multiple Endocrine Neoplasia Syndrome, Childhood
Multiple Myeloma/Plasma Cell Neoplasm
Mycosis Fungoides
Myelodysplastic Syndromes
Myelodysplastic/Myeloproliferative Diseases
Myelogenous Leukemia, Chronic
Myeloid Leukemia, Adult Acute
Myeloid Leukemia, Childhood Acute
Myeloma, Multiple
Myeloproliferative Disorders, Chronic
Nasal Cavity and Paranasal Sinus Cancer
Nasopharyngeal Cancer
Nasopharyngeal Cancer, Childhood
Neuroblastoma
Non-Hodgkin's Lymphoma, Adult
Non-Hodgkin's Lymphoma, Childhood
Non-Hodgkin's Lymphoma During Pregnancy
Non-Small Cell Lung Cancer
Oral Cancer, Childhood
Oral Cavity Cancer, Lip and
Oropharyngeal Cancer
Osteosarcoma/Malignant Fibrous Histiocytoma of Bone
Ovarian Cancer, Childhood
Ovarian Epithelial Cancer
Ovarian Germ Cell Tumor
Ovarian Low Malignant Potential Tumor
Pancreatic Cancer
Pancreatic Cancer, Childhood
Pancreatic Cancer, Islet Cell
Paranasal Sinus and Nasal Cavity Cancer
Parathyroid Cancer
Penile Cancer
Pheochromocytoma
Pineoblastoma and Supratentorial Primitive Neuroectodermal Tumors, Childhood
Pituitary Tumor
Plasma Cell Neoplasm/Multiple Myeloma
Pleuropulmonary Blastoma
Pregnancy and Breast Cancer
Pregnancy and Hodgkin's Lymphoma
Pregnancy and Non-Hodgkin's Lymphoma
Primary Central Nervous System Lymphoma
Prostate Cancer
Rectal Cancer
Renal Cell (Kidney) Cancer
Renal Cell (Kidney) Cancer, Childhood
Renal Pelvis and Ureter, Transitional Cell Cancer
Retinoblastoma
Rhabdomyosarcoma, Childhood
Salivary Gland Cancer
Salivary Gland Cancer, Childhood
Sarcoma, Ewing's Family of Tumors
Sarcoma, Kaposi's
Sarcoma, Soft Tissue, Adult
Sarcoma, Soft Tissue, Childhood
Sarcoma, Uterine
Sezary Syndrome
Skin Cancer (non-Melanoma)
Skin Cancer, Childhood TABLE 2-continued Types of Cancer Uterine Cancer, Endometrial
Uterine Sarcoma
Vaginal Cancer
Visual Pathway and Hypothalamic
Glioma, Childhood
Vulvar Cancer
Waldenström's Macroglobulinemia
Wilms' Tumor In further embodiments of the present invention, the compounds disclosed herein can be used in the treatment of angiogenesis-related diseases.

Antiangiogenic small molecules include thalidomide, which acts in part by inhibiting NFkB, 2-methoxyestradiol, which influences microtubule activation and hypoxia inducing factor (HIF1a) activation, cyclo-oxygenase 2 (COX2) inhibitors, and low doses of conventional chemotherapeutic agents, including cyclophosphamide, taxanes, and vinca alkaloids (vincristine, vinblastine) (D'Amato R. J. et al., Proc. Natl. Acad. Sci. U.S.A., 1994. 91: p. 3964-3968; D'Amato R. J. et al., Proc. Natl. Acad. Sci. U.S.A., 1994. 91: p. 4082-4085). In addition, certain tyrosine kinase inhibitors indirectly decrease angiogenesis by decreasing production of VEGF and other proangiogenic factors by tumor and stromal cells. These drugs include Herceptin, imatinib (Glivec), and Iressa (Bergers G. et al., J Clin Invest, 2003. 111: p. 1287-1295; Ciardiello F. et al., Clin Cancer Res, 2001. 7: p. 1459-1465; Plum S. M. et al., Clin Cancer Res, 2003. 9: p. 4619-4626).

Recently, angiogenesis inhibitors have moved from animal models to human patients. Angiogenesis inhibitors represent a promising treatment for a variety of cancers. Recently, Avastin a high affinity antibody against vascular endothelial growth factor (VEGF), has been shown to prolong life as a single agent in advanced renal cell carcinoma and prolong life in combination with chemotherapy in advanced colon cancer (Yang J. C. et al., New Eng J Med, 2003. 349: p. 427-434; Kabbinavar F. et al., J Clin Onc, 2003. 21: p. 60-65).

Angiogenesis-related diseases include, but are not limited to, inflammatory, autoimmune, and infectious diseases; angiogenesis-dependent cancer, including, for example, solid tumors, blood born tumors such as leukemias, and tumor metastases; benign tumors, for example hemangiomas, acoustic neuromas, neurofibromas, trachomas, and pyogenic granulomas; rheumatoid arthritis; psoriasis; eczema; ocular angiogenic diseases, for example, diabetic retinopathy, retinopathy of prematurity, macular degeneration, corneal graft rejection, neovascular glaucoma, retrolental fibroplasia, rubeosis; Osler-Webber Syndrome; myocardial angiogenesis; plaque neovascularization; telangiectasia; hemophiliac joints; angiofibroma; and wound granulation. In addition, compositions of this invention can be used to treat diseases such as, but not limited to, intestinal adhesions, atherosclerosis, scleroderma, warts, and hypertrophic scars (i.e., keloids). Compositions of this invention can also be used in the treatment of diseases that have angiogenesis as a pathologic consequence such as cat scratch disease (Rochele minalia quintosa), ulcers (*Helobacter pylori*), tuberculosis, and leprosy.

6.1. Treatment of Drug Resistant Tumors or Cancers

The invention provides compounds that can be used to treat drug resistant cancer, including the embodiments of cancers and the triciribine compound and/or the an erlotinib-like compound, for example, gefitinib, erlotinib or a salt thereof.

Multidrug resistance (MDR) occurs in human cancers and can be a significant obstacle to the success of chemotherapy. Multidrug resistance is a phenomenon whereby tumor cells in vitro that have been exposed to one cytotoxic agent develop cross-resistance to a range of structurally and functionally unrelated compounds. In addition, MDR can occur intrinsically in some cancers without previous exposure to chemotherapy agents. Thus, in one embodiment, the present invention provides methods for the treatment of a patient with a drug resistant cancer, for example, multidrug resistant cancer, by administration of TCN, TCN-P or a related compound and an erlotinib-like compound, for example, gefitinib, erlotinib or a salt thereof. In certain embodiments, TCN, TCN-P and related compounds and an erlotinib-like compound, for example, gefitinib, erlotinib or a salt thereof can be used to treat cancers that are resistant to taxol alone, rapamycin, tamoxifen, cisplatin, and/or gefitinib (iressa).

In one embodiment, TCN, TCN-P or a related compound and an erlotinib-like compound, for example, gefitinib, erlotinib or a salt thereof can be used for the treatment of drug resistant cancers of the colon, bone, kidney, adrenal, pancreas, liver and/or any other cancer known in the art or described herein.

6.2. Combination Therapy

In one embodiment, the triciribine compounds and an erlotinib-like compound, for example, gefitinib, erlotinib or a salt thereof can be administered together with other cytotoxic agents. In another embodiment, the triciribine compounds and an erlotinib-like compound, for example, gefitinib, erlotinib or a salt thereof and compositions thereof, when used in the treatment of solid tumors, can be administered the use of radiation.

In another embodiment of the present invention, the the triciribine compounds and an erlotinib-like compound, for example, gefitinib, erlotinib or a salt thereof and compositions disclosed herein can be combined with at least one additional chemotherapeutic agent. The additional agents can be administered in combination or alternation with the compounds disclosed herein. The drugs can form part of the same composition, or be provided as a separate composition for administration at the same time or a different time.

In one embodiment, the triciribine compounds and an erlotinib-like compound, for example, gefitinib, erlotinib or a salt thereof disclosed herein can be combined with antiangiogenic agents to enhance their effectiveness, or combined with other antiangiogenic agents and administered together with other cytotoxic agents. In another embodiment, the triciribine compounds and an erlotinib-like compound, for example, gefitinib, erlotinib or a salt thereof and compositions, when used in the treatment of solid tumors, can be administered with the agents selected from, but not limited to IL-12, retinoids, interferons, angiostatin, endostatin, thalidomide, thrombospondin-1, thrombospondin-2, captopryl, anti-neoplastic agents such as alpha interferon, COMP (cyclophosphamide, vincristine, methotrexate and prednisone), etoposide, mBACOD (methortrexate, bleomycin, doxorubicin, cyclophosphamide, vincristine and dexamethasone), PRO-MACE/MOPP (prednisone, methotrexate (w/leucovin rescue), doxorubicin, cyclophosphamide, etoposide/mechlorethamine, vincristine, prednisone and procarbazine), vincristine, vinblastine, angioinhibins, TNP-470, pentosan polysulfate, platelet factor 4, angiostatin, LM-609, SU-101, CM-101, Techgalan, thalidomide, SP-PG and radiation. In further embodiments, the compounds and compositions disclosed herein can be administered in combination or alternation with, for example, drugs with antimitotic effects, such as those which target cytoskeletal elements, including podophylotoxins or vinca alkaloids (vincristine, vinblastine); antimetabolite drugs (such as 5-fluorouracil, cytarabine, gemcitabine, purine analogues such as pentostatin, methotrexate); alkylating agents or nitrogen mustards (such as nitrosoureas, cyclophosphamide or ifosphamide); drugs which target DNA such as the antracycline drugs adriamycin, doxorubicin, pharmorubicin or epirubicin; drugs which target topoisomerases such as etoposide; hormones and hormone agonists or antagonists such as estrogens, antiestrogens (tamoxifen and related compounds) and androgens, flutamide, leuprorelin, goserelin, cyprotrone or octreotide; drugs which target signal transduction in tumour cells including antibody derivatives such as herceptin; alkylating drugs such as platinum drugs (cis-platin, carbonplatin, oxaliplatin, paraplatin) or nitrosoureas; drugs potentially affecting metastasis of tumours such as matrix metalloproteinase inhibitors; gene therapy and antisense agents; antibody therapeutics; other bioactive compounds of marine origin, notably the didemnins such as aplidine; steroid analogues, in particular dexamethasone; anti-inflammatory drugs, including nonsteroidal agents (such as acetaminophen or ibuprofen) or steroids and their derivatives in particular dexamethasone; anti-emetic drugs, including 5HT-3 inhibitors (such as gramisetron or ondasetron), and steroids and their derivatives in particular dexamethasone. In still further embodiments, the compounds and compositions can be used in combination or alternation with the chemotherapeutic agents disclosed below in Table 3.

TABLE 3

| Chemotherapeutic Agents | |
|---|---|
| 13-cis-Retinoic Acid | Neosar |
| 2-Amino-6-Mercaptopurine | Neulasta |
| 2-CdA | Neumega |
| 2-Chlorodeoxyadenosine | Neupogen |
| 5-fluorouracil | Nilandron |
| 5-FU | Nilutamide |
| 6-TG | Nitrogen Mustard |
| 6-Thioguanine | Novaldex |
| 6-Mercaptopurine | Novantrone |
| 6-MP | Octreotide |
| Accutane | Octreotide acetate |
| Actinomycin-D | Oncospar |
| Adriamycin | Oncovin |
| Adrucil | Ontak |
| Agrylin | Onxal |
| Ala-Cort | Oprevelkin |
| Aldesleukin | Orapred |
| Alemtuzumab | Orasone |
| Alitretinoin | Oxaliplatin |
| Alkaban-AQ | Paclitaxel |

TABLE 3-continued

| Chemotherapeutic Agents | |
|---|---|
| Alkeran | Pamidronate |
| All-transretinoic acid | Panretin |
| Alpha interferon | Paraplatin |
| Altretamine | Pediapred |
| Amethopterin | PEG Interferon |
| Amifostine | Pegaspargase |
| Aminoglutethimide | Pegfilgrastim |
| Anagrelide | PEG-INTRON |
| Anandron | PEG-L-asparaginase |
| Anastrozole | Phenylalanine Mustard |
| Arabinosylcytosine | Platinol |
| Ara-C | Platinol-AQ |
| Aranesp | Prednisolone |
| Aredia | Prednisone |
| Arimidex | Prelone |
| Aromasin | Procarbazine |
| Arsenic trioxide | PROCRIT |
| Asparaginase | Proleukin |
| ATRA | Prolifeprospan 20 with |
| Avastin | Carmustine implant |
| BCG | Purinethol |
| BCNU | Raloxifene |
| Bevacizumab | Rheumatrex |
| Bexarotene | Rituxan |
| Bicalutamide | Rituximab |
| BiCNU | Roveron-A (interferon alfa-2a) |
| Blenoxane | Rubex |
| Bleomycin | Rubidomycin hydrochloride |
| Bortezomib | Sandostatin |
| Busulfan | Sandostatin LAR |
| Busulfex | Sargramostim |
| C225 | Solu-Cortef |
| Calcium Leucovorin | Solu-Medrol |
| Campath | STI-571 |
| Camptosar | Streptozocin |
| Camptothecin-11 | Tamoxifen |
| Capecitabine | Targretin |
| Carac | Taxol |
| Carboplatin | Taxotere |
| Carmustine | Temodar |
| Carmustine wafer | Temozolomide |
| Casodex | Teniposide |
| CCNU | TESPA |
| CDDP | Thalidomide |
| CeeNU | Thalomid |
| Cerubidine | TheraCys |
| cetuximab | Thioguanine |
| Chlorambucil | Thioguanine Tabloid |
| Cisplatin | Thiophosphoamide |
| Citrovorum Factor | Thioplex |
| Cladribine | Thiotepa |
| Cortisone | TICE |
| Cosmegen | Toposar |
| CPT-11 | Topotecan |
| Cyclophosphamide | Toremifene |
| Cytadren | Trastuzumab |
| Cytarabine | Tretinoin |
| Cytarabine liposomal | Trexall |
| Cytosar-U | Trisenox |
| Cytoxan | TSPA |
| Dacarbazine | VCR |
| Dactinomycin | Velban |
| Darbepoetin alfa | Velcade |
| Daunomycin | VePesid |
| Daunorubicin | Vesanoid |
| Daunorubicin hydrochloride | Viadur |
| Daunorubicin liposomal | Vinblastine |
| DaunoXome | Vinblastine Sulfate |
| Decadron | Vincasar Pfs |
| Delta-Cortef | Vincristine |
| Deltasone | Vinorelbine |
| Denileukin diftitox | Vinorelbine tartrate |
| DepoCyt | VLB |
| Dexamethasone | VP-16 |
| Dexamethasone acetate | Vumon |
| dexamethasone sodium phosphate | Xeloda |
| Dexasone | Zanosar |
| Dexrazoxane | Zevalin |

TABLE 3-continued

Chemotherapeutic Agents

| | |
|---|---|
| DHAD | Zinecard |
| DIC | Zoladex |
| Diodex | Zoledronic acid |
| Docetaxel | Zometa |
| Doxil | Gliadel wafer |
| Doxorubicin | Glivec |
| Doxorubicin liposomal | GM-CSF |
| Droxia | Goserelin |
| DTIC | granulocyte - colony stimulating factor |
| DTIC-Dome | |
| Duralone | Granulocyte macrophage colony stimulating factor |
| Efudex | |
| Eligard | Halotestin |
| Ellence | Herceptin |
| Eloxatin | Hexadrol |
| Elspar | Hexalen |
| Emcyt | Hexamethylmelamine |
| Epirubicin | HMM |
| Epoetin alfa | Hycamtin |
| Erbitux | Hydrea |
| *Erwinia* L-asparaginase | Hydrocort Acetate |
| Estramustine | Hydrocortisone |
| Ethyol | Hydrocortisone sodium phosphate |
| Etopophos | Hydrocortisone sodium succinate |
| Etoposide | Hydrocortone phosphate |
| Etoposide phosphate | Hydroxyurea |
| Eulexin | Ibritumomab |
| Evista | Ibritumomab Tiuxetan |
| Exemestane | Idamycin |
| Fareston | Idarubicin |
| Faslodex | Ifex |
| Femara | IFN-alpha |
| Filgrastim | Ifosfamide |
| Floxuridine | IL - 2 |
| Fludara | IL-11 |
| Fludarabine | Imatinib mesylate |
| Fluoroplex | Imidazole Carboxamide |
| Fluorouracil | Interferon alfa |
| Fluorouracil (cream) | Interferon Alfa-2b (PEG conjugate) |
| Fluoxymesterone | Interleukin - 2 |
| Flutamide | Interleukin-11 |
| Folinic Acid | Intron A (interferon alfa-2b) |
| FUDR | Leucovorin |
| Fulvestrant | Leukeran |
| G-CSF | Leukine |
| Gefitinib | Leuprolide |
| Gemcitabine | Leurocristine |
| Gemtuzumab ozogamicin | Leustatin |
| Gemzar | Liposomal Ara-C |
| Gleevec | Liquid Pred |
| Lupron | Lomustine |
| Lupron Depot | L-PAM |
| Matulane | L-Sarcolysin |
| Maxidex | Meticorten |
| Mechlorethamine | Mitomycin |
| Mechlorethamine Hydrochlorine | Mitomycin-C |
| Medralone | Mitoxantrone |
| Medrol | M-Prednisol |
| Megace | MTC |
| Megestrol | MTX |
| Megestrol Acetate | Mustargen |
| Melphalan | Mustine |
| Mercaptopurine | Mutamycin |
| Mesna | Myleran |
| Mesnex | Iressa |
| Methotrexate | Irinotecan |
| Methotrexate Sodium | Isotretinoin |
| Methylprednisolone | Kidrolase |
| Mylocel | Lanacort |
| Letrozole | L-asparaginase |
| | LCR |

In certain embodiments, interferons (IFNs) can be used in combinations with the compounds of the present invention. Suitable intereferons include: interferon alpha-2a, interferon alpha-2b, pegylated interferon alpha, including interferon alpha-2a and interferon alpha 2b, interferon beta, interferon gamma, interferon tau, interferon omega, INFERGEN (interferon alphacon-1) by InterMune, OMNIFERON (natural interferon) by Viragen, ALBUFERON by Human Genome Sciences, REBIF (interferon beta-1a) by Ares-Serono, Omega Interferon by BioMedicine, Oral Interferon Alpha by Amarillo Biosciences, and interferon gamma, interferon tau, and/or interferon gamma-1☐ by InterMune.

In one embodiment TCN, TCN-P or a related compound and an erlotinib-like compound, for example, gefitinib, erlotinib or a salt thereof as disclosed herein can be used in combination or alternation with additional chemotherapeutic agents, such as those described herein or in Table 3, for the treatment of drug resistant cancer, for example multiple drug resistant cancer. Drug resistant cancers can include cancers of the colon, bone, kidney, adrenal, pancreas, liver and/or any other cancer known in the art or described herein. In one embodiment, the additional chemotherapeutic agent can be a P-glycoprotein inhibitor. In certain non-limiting embodiments, the P-glycoprotein inhibitor can be selected from the following drugs: verapamil, cyclosporin (such as cyclosporin A), tamoxifen, calmodulin antagonists, dexverapamil, dexniguldipine, valspodar (PSC 833), biricodar (VX-710), tariquidar (XR9576), zosuquidar (LY335979), laniquidar (R101933), and/or ONT-093.

7. PHARMACEUTICAL COMPOSITIONS

The compositions including triciribine compounds and an erlotinib-like compound, for example, gefitinib, erlotinib or a salt thereof can optionally be administered with a pharmaceutical carrier or excipient. Pharmaceutical carriers suitable for administration of the compounds provided herein include any such carriers known to those skilled in the art to be suitable for the particular mode of administration. The triciribine compounds and in combination with an erlotinib-like compound, for example, gefitinib, erlotinib or a salt thereof may be formulated as the sole pharmaceutically active ingredients in the composition or may be combined.

Compositions including the triciribine compounds and an erlotinib-like compound, for example, gefitinib, erlotinib or a salt thereof may be suitable for oral, rectal, nasal, topical (including buccal and sublingual), vaginal, or parenteral (including subcutaneous, intramuscular, subcutaneous, intravenous, intradermal, intraocular, intratracheal, intracisternal, intraperitoneal, and epidural) administration. Preferably the compositions are administered intravenously.

The compositions may conveniently be presented in unit dosage form and may be prepared by conventional pharmaceutical techniques. Such techniques include the step of bringing into association one or more compositions of the present invention and one or more pharmaceutical carriers or excipients.

The triciribine compounds and and an erlotinib-like compound, for example, gefitinib, erlotinib or a salt thereof and compositions thereof can be formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. In one embodiment, the triciribine compounds described above are formulated into pharmaceutical compositions using techniques and procedures well known in the art (see, e.g., Ansel, Introduction to Pharmaceutical Dosage Forms, Fourth Ed., 1985, p. 126).

In the compositions, effective concentrations of one or more compounds or pharmaceutically acceptable derivatives thereof may be mixed with one or more suitable pharmaceutical carriers. The compounds of the invention may be derivatized as the corresponding salts, esters, enol ethers or esters, acetals, ketals, orthoesters, hemiacetals, hemiketals, acids, bases, solvates, hydrates or prodrugs prior to formulation. The concentrations of the compounds in the compositions are effective for delivery of an amount, upon administration, that treats, prevents, or ameliorates one or more of the symptoms of the target disease or disorder. In one embodiment, the compositions are formulated for single dosage administration. To formulate a composition, the weight fraction of compound is dissolved, suspended, dispersed or otherwise mixed in a selected carrier at an effective concentration such that the treated condition is relieved, prevented, or one or more symptoms are ameliorated.

Compositions suitable for oral administration may be presented as discrete units such as, but not limited to, tablets, caplets, pills or dragees capsules, or cachets, each containing a predetermined amount of one or more of the compositions; as a powder or granules; as a solution or a suspension in an aqueous liquid or a non-aqueous liquid; or as an oil-in-water liquid emulsion or a water-in-oil emulsion or as a bolus, etc.

Liquid pharmaceutically administrable compositions can, for example, be prepared by dissolving, dispersing, or otherwise mixing a triciribine compound and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, solubilizing agents, pH buffering agents, preservatives, flavoring agents, and the like, for example, acetate, sodium citrate, cyclodextrine derivatives, sorbitan monolaurate, triethanolamine sodium acetate, triethanolamine oleate, and other such agents. Methods of preparing such dosage forms are known, or will be apparent, to those skilled in this art; for example, see Remington's Pharmaceutical Sciences, Mack Publishing Company, Easton, Pa.

Compositions of the present invention suitable for topical administration in the mouth include for example, lozenges, having the ingredients in a flavored basis, usually sucrose and acacia or tragacanth; pastilles, having one or more triciribine compounds and an erlotinib-like compound, for example, gefitinib, erlotinib or a salt thereof of the present invention in an inert basis such as gelatin and glycerin, or sucrose and acacia; and mouthwashes, having one or more of the compositions of the present invention administered in a suitable liquid carrie The tablets, pills, capsules, troches and the like can contain one or more of the following ingredients, or compounds of a similar nature: a binder; a lubricant; a diluent; a glidant; a disintegrating agent; a coloring agent; a sweetening agent; a flavoring agent; a wetting agent; an emetic coating; and a film coating. Examples of binders include microcrystalline cellulose, gum tragacanth, glucose solution, acacia mucilage, gelatin solution, molasses, polvinylpyrrolidine, povidone, crospovidones, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

Compositions suitable for topical administration to the skin may be presented as ointments, creams, gels, and pastes, having one or more of the compositions administered in a pharmaceutical acceptable carrier.

Compositions for rectal administration may be presented as a suppository with a suitable base including, for example, cocoa butter or a salicylate.

Compositions suitable for nasal administration, when the carrier is a solid, include a coarse powder having a particle size, for example, in the range of 20 to 500 microns which is administered in the manner in which snuff is taken, (i.e., by rapid inhalation through the nasal passage from a container of the powder held close up to the nose). When the carrier is a liquid (for example, a nasal spray or as nasal drops), one or more of the compositions can be admixed in an aqueous or oily solution, and inhaled or sprayed into the nasal passage.

Compositions suitable for vaginal administration may be presented as pessaries, tampons, creams, gels, pastes, foams or spray formulations containing one or more of the compositions and appropriate carriers.

Compositions suitable for parenteral administration include aqueous and non-aqueous sterile injection solutions which may contain anti-oxidants, buffers, bacteriostats, and solutes which render the formulation isotonic with the blood of the intended recipient; and aqueous and non-aqueous sterile suspensions which may include suspending agents and thickening agents. The compositions may be presented in unit-dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules, and tablets of the kind previously described above.

Pharmaceutical organic or inorganic solid or liquid carrier media suitable for enteral or parenteral administration can be used to fabricate the compositions. Gelatin, lactose, starch, magnesium stearate, talc, vegetable and animal fats and oils, gum, polyalkylene glycol, water, or other known carriers may all be suitable as carrier media.

Compositions including triciribine compounds and an erlotinib-like compound, for example, gefitinib, erlotinib or a salt thereof may be used in combination with one or more pharmaceutically acceptable carrier mediums and/or excipients. As used herein, "pharmaceutically acceptable carrier medium" includes any and all carriers, solvents, diluents, or other liquid vehicles, dispersion or suspension aids, surface active agents, isotonic agents, thickening or emulsifying agents, preservatives, solid binders, lubricants, adjuvants, vehicles, delivery systems, disintegrants, absorbents, preservatives, surfactants, colorants, flavorants, or sweeteners and the like, as suited to the particular dosage form desired.

Additionally, the compositions including triciribine compounds and an erlotinib-like compound, for example, gefitinib, erlotinib or a salt thereof may be combined with pharmaceutically acceptable excipients, and, optionally, sustained-release matrices, such as biodegradable polymers, to form therapeutic compositions. A "pharmaceutically acceptable excipient" includes a non-toxic solid, semi-solid or liquid filler, diluent, encapsulating material or formulation auxiliary of any type.

It will be understood, however, that the total daily usage of the compositions will be decided by the attending physician within the scope of sound medical judgment. The specific therapeutically effective dose level for any particular host will depend upon a variety of factors, including for example, the disorder being treated and the severity of the disorder; activity of the specific composition employed; the specific composition employed, the age, body weight, general health, sex and diet of the patient; the time of administration; route of administration; rate of excretion of the specific compound employed; the duration of the treatment; the triciribine compound and/or the an erlotinib-like compound, for example, gefitinib, erlotinib or a salt thereof used in combination or coincidental with the specific composition employed; and like factors well known in the medical arts. For example, it is well within the skill of the art to start doses of the composition at levels lower than those required to achieve the desired therapeutic effect and to gradually increase the dosage until the desired effect is achieved.

Compositions including triciribine compounds and an erlotinib-like compound, for example, gefitinib, erlotinib or a salt thereof are preferably formulated in dosage unit form for ease of administration and uniformity of dosage. "Dosage unit form" as used herein refers to a physically discrete unit of the composition appropriate for the host to be treated. Each dosage should contain the quantity of composition calculated to produce the desired therapeutic affect either as such, or in association with the selected pharmaceutical carrier medium.

Preferred unit dosage formulations are those containing a daily dose or unit, daily sub-dose, or an appropriate fraction thereof, of the administered ingredient. For example, approximately 1-5 mg per day of a compound disclosed herein can reduce the volume of a solid tumor in mice.

The dosage will depend on host factors such as weight, age, surface area, metabolism, tissue distribution, absorption rate and excretion rate. In one embodiment, approximately 0.5 to 7 grams per day of a triciribine compound disclosed herein may be administered to humans. Optionally, approximately 1 to 4 grams per day of the compound can be administered to humans. In certain embodiments 0.001-5 mg/day is administered to a human. The therapeutically effective dose level will depend on many factors as noted above. In addition, it is well within the skill of the art to start doses of the composition at relatively low levels, and increase the dosage until the desired effect is achieved.

Compositions including triciribine compounds and an erlotinib-like compound, for example, gefitinib, erlotinib or a salt thereof may be used with a sustained-release matrix, which can be made of materials, usually polymers, which are degradable by enzymatic or acid-based hydrolysis or by dissolution. Once inserted into the body, the matrix is acted upon by enzymes and body fluids. A sustained-release matrix for example is chosen from biocompatible materials such as liposomes, polylactides (polylactic acid), polyglycolide (polymer of glycolic acid), polylactide co-glycolide (copolymers of lactic acid and glycolic acid), polyanhydrides, poly(ortho)esters, polypeptides, hyaluronic acid, collagen, chondroitin sulfate, carboxcylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide (co-polymers of lactic acid and glycolic acid).

The triciribine compounds and an erlotinib-like compound, for example, gefitinib, erlotinib or a salt thereof may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically-acceptable and metabolizable lipid capable of forming liposomes can be used. The liposome can contain, in addition to one or more compositions of the present invention, stabilizers, preservatives, excipients, and the like. Examples of lipids are the phospholipids and the phosphatidyl cholines (lecithins), both natural and synthetic. Methods to form liposomes are known in the art.

The triciribine compounds and an erlotinib-like compound, for example, gefitinib, erlotinib or a salt thereof may be formulated as aerosols for application, such as by inhalation. These formulations for administration to the respiratory tract can be in the form of an aerosol or solution for a nebulizer, or as a microfine powder for insufflation, alone or in combination with an inert carrier such as lactose. In such a case, the particles of the formulation will, in one embodiment, have diameters of less than 50 microns, in one embodiment less than 10 microns.

Compositions including the triciribine compounds and an erlotinib-like compound, for example, gefitinib, erlotinib or a salt thereof may be used in combination with other compositions and/or procedures for the treatment of the conditions described above. For example, a tumor may be treated conventionally with surgery, radiation, or chemotherapy combined with one or more compositions of the present invention and then one or more compositions of the present invention may be subsequently administered to the patient to extend the dormancy of micrometastases and to stabilize, inhibit, or reduce the growth of any residual primary tumor.

7.1. Additional Embodiments

The pharmaceutical compositions including triciribine compounds and an erlotinib-like compound, for example, gefitinib, erlotinib or a salt thereof can be formulated according to known methods for preparing pharmaceutically useful compositions. Formulations are described in a number of sources which are well known and readily available to those skilled in the art. For example, Remington's Pharmaceutical Sciences, Mack Publishing Company, Easton, Pa. describes formulations which can be used in connection with the subject invention. Formulations suitable for administration include, for example, aqueous sterile injection solutions, which may contain antioxidants, buffers, bacteriostats, and solutes which render the formulation isotonic with the blood of the intended recipient; and aqueous and nonaqueous sterile suspensions which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the formulations of the subject invention can include other agents conventional in the art having regard to the type of formulation in question.

The methods of the present invention, for example, for inhibiting the growth of a cancerous cell, can be advantageously combined with at least one additional therapeutic method, including but not limited to chemotherapy, radiation therapy, therapy that selectively inhibits Ras oncogenic signaling, or any other therapy known to those of skill in the art of the treatment and management of cancer, such as administration of an anti-cancer agent.

Administration of API-2 (triciribine) as a salt may be carried out. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, alpha-ketoglutarate, and alpha-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The triciribine compounds and an erlotinib-like compound, for example, gefitinib, erlotinib or a salt thereof can be formulated as pharmaceutical compositions and administered to a subject, such as a human or veterinary patient, in a variety of forms adapted to the chosen route of administration, i.e., orally or parenterally, by intravenous, intramuscular, topical or subcutaneous routes.

Thus, the triciribine compounds and an erlotinib-like compound, for example, gefitinib, erlotinib or a salt thereof of the present invention may be systemically administered, e.g., orally, in combination with a pharmaceutically acceptable vehicle (i.e., carrier) such as an inert diluent or an assimilable edible carrier. They may be enclosed in hard or soft shell gelatin capsules, may be compressed into tablets, or may be incorporated directly with the food of the patient's diet. For oral therapeutic administration, the compounds may be combined with one or more excipients and used in the form of ingestible tablets, buccal tablets, troches, capsules, elixirs, suspensions, syrups, wafers, and the like. Such compositions and preparations should contain at least 0.1% of active agent. The percentage of the compositions and preparations may, of course, be varied and may conveniently be between about 2 to about 60% of the weight of a given unit dosage form. The amount of the active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the compounds of the invention, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the compounds of the invention may be incorporated into sustained-release preparations and devices.

The triciribine compounds and an erlotinib-like compound, for example, gefitinib, erlotinib or a salt thereof may also be administered intravenously or intraperitoneally by infusion or injection. Solutions of the active agents or their salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders including the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium including, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating compounds of the invention in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the triciribine compounds and an erlotinib-like compound, for example, gefitinib, erlotinib or a salt thereof may be applied in pure-form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the compounds of the invention can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver the compounds of the invention to the skin are disclosed in Jacquet et al. (U.S. Pat. No. 4,608,392), Geria (U.S. Pat. No. 4,992,478), Smith et al. (U.S. Pat. No. 4,559,157) and Woltzman (U.S. Pat. No. 4,820,508).

Useful dosages of the pharmaceutical compositions of the present invention can be determined by comparing their in vitro activity, and in vivo activity in animal models. Methods for the extrapolation of effective dosages in mice, and other animals, to humans are known to the art; for example, see U.S. Pat. No. 4,938,949.

In one non-limiting embodiment, the concentration of the active agent in a liquid composition, such as a lotion, can be from about 0.1-25 wt-%, or from about 0.5-10 wt.-%. In one embodiment, the concentration in a semi-solid or solid composition such as a gel or a powder can be about 0.1-5 wt.-%, preferably about 0.5-2.5 wt.-%. In one embodiment, single dosages for injection, infusion or ingestion will generally vary between 5-1500 mg, and may be administered, i.e., 1-3 times daily, to yield levels of about 0.1-50 mg/kg, for adults. A non-limiting dosage of the present invention can be between 7.5 to 45 mg per clay, administered orally, with appropriate adjustment for the body weight of an individual.

Accordingly, the present invention includes a pharmaceutical composition including triciribine compounds and an erlotinib-like compound, for example, gefitinib, erlotinib or a salt thereof in combination with a pharmaceutically acceptable carrier. Pharmaceutical compositions adapted for oral, topical or parenteral administration, including an amount of triciribine compounds and an erlotinib-like compound, for example, gefitinib, erlotinib or a salt thereof, constitute a preferred embodiment of the invention. The dose administered to a subject, particularly a human, in the context of the present invention should be sufficient to affect a therapeutic response in the patient over a reasonable time frame. One skilled in the art will recognize that dosage will depend upon a variety of factors including the condition of the animal, the body weight of the animal, as well as the severity and stage of the cancer.

A suitable dose is that which will result in a concentration of the triciribine compounds and an erlotinib-like compound, for example, gefitinib, erlotinib or a salt thereof in tumor tissue which is known to affect the desired response. The preferred dosage is the amount which results in maximum inhibition of cancer cell growth, without unmanageable side effects. Administration of API-2 (or a pharmaceutically acceptable salt thereof) can be continuous or at distinct intervals, as can be determined by a person of ordinary skill in the art.

Mammalian species which benefit from the disclosed methods for the inhibition of cancer cell growth, include, but are not limited to, primates, such as apes, chimpanzees, orangutans, humans, monkeys; domesticated animals (e.g., pets) such as dogs, cats, guinea pigs, hamsters, Vietnamese pot-bellied pigs, rabbits, and ferrets; domesticated farm animals such as cows, buffalo, bison, horses, donkey, swine, sheep, and goats; exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, opossums, raccoons, pandas, hyena, seals, sea lions, elephant seals, otters, porpoises, dolphins, and whales. The terms "patient" and "subject" are used herein interchangeably and are intended to include such human and non-human mammalian species. Likewise, in vitro methods of the present invention can be earned out on cells of such mammalian species.

Patients in need of treatment using the methods of the present invention can be identified using standard techniques known to those in the medical profession.

The following examples are offered by way of illustration and not by way of limitation.

8. EXAMPLES

Example 1: In Vitro Screening

Cell Lines and NCI Diversity Set.

All cell lines can be purchased from ATCC or described previously (Cheng J. Q. et al., Oncogene, 1997. 14: p. 2793-2801; West, K. A. et al., Drug Resist Updat, 2002. 5: p. 234-248; Satyamoorthy K. et al., Cancer Res, 2001. 61: p. 7318-7324). The NCI Structural Diversity Set is a library of 1,992 compounds selected from the approximately 140,000-compound NCI drug depository. In-depth data on the selection, structures, and activities of these diversity set compounds can be found on the NCI Developmental Therapeutics Program web site.

Screening for Inhibition of Akt-Transformed Cell Growth.

AKT2 transformed NIH3T3 cells or LXSN vector-transfected NIH3T3 control cells (Cheng J. Q. et al., Oncogene, 1997. 14: p. 2793-2801) are plated into 96-well tissue culture plate. Following treatment with 5 µM of NCI Diversity Set compound, cell growth can be detected with CellTier 96 One Solution Cell Proliferation kit (Promega). Compounds that inhibit growth in AKT2-transformed but not LXSN-transfected NIH3T3 cells are considered as candidates of Akt inhibitor and subjected to further analysis.

In Vitro Protein Kinase, Cell Survival and Apoptosis Assays.

In vitro kinase is performed as previously described (see, for example, Jiang K. et al., Mol Cell Biol, 2000. 20: p. 139-148). Cell survival is assayed with MTS (Promega). Apoptosis was detected with annexin V, which is performed as previously described (Jiang K. et al., Mol Cell Biol, 2000. 20: p. 139-148). Recombinant Akt and PDK1 are purchased from Upstate Biotechnology Inc.

Results

Identification of Small Molecule Inhibitor of Akt Signaling Pathway, API-2.

Frequent alterations of Akt has been detected in human cancer and disruption of Akt pathway induces apoptosis and inhibits tumor growth (Jetzt A. et al., Cancer Res, 2003. 63: p. 697-706, 2003). Thus, Akt is considered as an attractive molecular target for development of novel cancer therapeutics. To identify small molecule inhibitor(s) of Akt, a chemical library of 1,992-compounds from the NCI (the NCI Diversity Set) is evaluated for agents capable of inhibition of growth in AKT2-transformed but not empty vector LXSN-transfected NIH3T3 cells. Repeated experiments showed that 32 compounds inhibited growth only in AKT2-transformed cells. The most potent of these compounds, API-2 (NCI identifier: NSC 154020), can suppress cell growth at a concentration of 50 nM. FIG. 1A shows the chemical structure of API-2, which is also known as triciribine (Schweinsberg P. D. et al., Biochem Pharmacol, 1981. 30: p. 2521-2526). The fact that API-2 inhibits selectively AKT-2 transformed cells over untransformed parental cells prompted us to determine whether API-2 is an inhibitor of AKT2 kinase. To this end, AKT2 is immunoprecipitated with anti-AKT2 antibody from AKT-2 transformed NIH3T3 cells following treatment with API-2. AKT2 immunoprecipitates were immunoblotted with anti-phospho-Akt antibodies. As shown in FIG. 1B, API-2 significantly inhibited AKT2 phosphorylation at both threonine-309 and serine-474, which are required for full activation of AKT2 (Datta S. R. et al., Genes Dev, 1999. 13: p. 2905-2927). As three isoforms of Akt share high homology and similar structure, the effect of API-2 on their kinase activities is evaluated. HEK293 cells are transfected with HA-Akt1, -AKT2 and AKT3, serum-starved overnight and treated with API-2 for 60 min prior to EGF (50 ng/ml) stimulation. Triple experiments showed that API-2 suppressed EGF-induced kinase activity and phosphorylation of Akt1, AKT2 and AKT3 (FIG. 1C). However, kinase activity of recombinant constitutively active AKT2 (Myr-AKT2) is not inhibited by API-2 in an in vitro kinase reaction (FIG. 1D), suggesting that API-2 does not directly inhibit Akt in vitro and that API-2 neither functions as ATP competitor nor as the substrate competitor that binds to active site of Akt.

API-2 does not Inhibit Known Upstream Activators of Akt.

It has been well documented that Akt is activated by extracellular stimuli and intracellular signal molecules, such as active Ras and Src, through a PI3K-dependent manner. Therefore, API-2 inhibition of Akt could result from targeting upstream molecule(s) of Akt. As PI3K and PDK1 are direct upstream regulators of Akt (Datta S. R. et al., Genes Dev, 1999. 13: p. 2905-2927), whether AP1-2 inhibits PI3K and/or PDK1 is examined. HEK293 cells are serum-starved and then can be treated with API-2 or PI3K inhibitor, wortmannin, for 30 min prior to EGF stimulation. PI3K is immunoprecipitated with anti-p110□□□antibody. The immunoprecipitates are subjected to in vitro PI3K kinase assay using P1-4-P as a substrate. As shown in FIG. 2A, the EGF-induced PI3K activity is inhibited by wortmannin but not by API-2. To evaluate the effect of API-2 on PDK1, an assay in which recombinant PDK1 promotes the threonine-309 phosphorylation of AKT2 peptides is used in the presence of lipid vesicles containing phosphotidylinositol. As shown in FIG. 2B, the assay is potently inhibited by the control PDK1 inhibitor staurosporine (IC50=5 nM). In contrast, API-2 displayed only 21% inhibition of the assay at the highest concentration tested (5.1 μM). To further evaluate the effect of API-2 on PDK1 activation, the autophosphorylation level of PDK1 at serine-241, a residue that is phosphorylated by itself and is critical for its activity is examined (Datta S. R. et al., Genes Dev, 1999. 13: p. 2905-2927), following API-2 treatment of HEK293 cells. Triplicate experiments show that phosphorylation levels of PDK1 are not inhibited by API-2 (FIG. 2B). However, PI3K inhibitor wortmannin can inhibit EGF-stimulated PDK1 (FIG. 2B).

API-2 is Highly Selective for the Akt Over PKC, PKA, SGK, STAT, JNK, p38, and ERK Signaling Pathways.

Akt belongs to AGC (PKA/PKG/PKC) kinase family, which also include PKA, PKC, serum- and glucocorticoid-inducible kinase (SGK), p90 ribosomal S6 kinase, $p70^{S6K}$, mitogen- and stress-activated protein kinase and PKC-related kinase. Among AGC kinase family, protein structures of PKA, PKC and SGK are more close to Akt kinase than other members. Therefore, next examined are the effects of API-2 on the enzymatic activities of these 3 kinases. HEK293 cells are transfected with HA-tagged PKA, PKCα, □or SGK. In vitro kinase assay and immunoblotting analysis show that the kinase activities of PKA and PKC□□are inhibited by PKAI and Ro 31-8220, a PKC inhibitor, respectively, whereas API-2 exhibits no effect on their activities (FIGS. 2C and 2E). Further, serum-induced SGK kinase activity is attenuated by wortmannin but not by API-2 (FIG. 2D). In addition, it is determined whether API-2 has effect on other oncogenic survival pathways. Western blotting analyses with commercially available anti-phospho-antibodies reveals that phosphorylation levels of Stat3, JNK, p38 and Erk1/2 were not affected by API-2 treatment (FIG. 2F). These data indicate that API-2 specifically inhibits Akt signaling pathway.

API-2 Suppresses Cell Growth and Induces Apoptosis in Akt-Overexpressing/Activating Human Cancer Cell Lines.

The ability of API-2 to selectively inhibit the Akt pathway suggests that it should inhibit proliferation and/or induces apoptosis preferentially in those tumor cells with aberrant expression/activation of Akt. As activation of Akt in human malignancies commonly results from overexpression of Akt or PTEN mutations, API-2 is used to treat the cells that express constitutively active Akt, caused by overexpression of AKT2 (OVCAR3, OVCAR8, PANC1 and AKT2-transformed NIH3T3) or mutations of the PTEN gene (PC-3, LNCaP, MDA-MB-468), and cells that do not (OVCAR5, DU-145, T47D, COLO357 and LXSN-NIH3T3) as well as melanoma cells that are activated by IGF-1 to activate Akt or do not respond to growth stimulation by IGF-1 (Satyamoorthy K. et al., Cancer Res, 2001. 61: p. 7318-7324). Immunoblotting analysis showed that phosphorylation levels of Akt are inhibited by API-2 only in the cells expressing elevated Akt or responding to IGF-1 simulation (FIG. 3A). Accordingly, API-2 inhibited cell growth to a much higher degree in Akt-overexpressing/activating cells as compared to those with low levels of Akt. As shown in FIG. 3B, API-2 treatment inhibited cell proliferation by approximately 50-60% in Akt-overexpressing/activating cell lines, LNCaP, PC-3, OVCAR3, OVCA8, PANC1, MDA-MB-468, and WM35, whereas only by about 10-20% in DU145, OVCAR5, COLO357, T47D and WM852 cells, which exhibit low levels of Akt or do not respond to growth stimulation by IGF-1. Moreover, API-2 induces apoptosis by 8-fold (OVCAR3), 6-fold (OVCAR8), 6-fold (PANC1), and 3-fold (AKT2-NIH3T3). No significant difference of apoptosis is observed between API-2 and vehicle (DMSO) treatment in OVCAR5, COLO357 and LXSN-NIH3T3 cells. Thus, API-2 inhibits cell growth and induces apoptosis preferentially in cells that express aberrant Akt.

API-2 Inhibits Downstream Targets of Akt.

It has been shown that Akt exerts its cellular effects through phosphorylation of a number of proteins (Datta S. R. et al., Genes Dev, 1999. 13: p. 2905-2927). More than 20 proteins have been identified as Akt substrates, including the members of Forkhead protein family (FKHR, AFX and FKHRLI), tuberlin/TSC2, $p70^{S6K}$, GSK-3□, $p21^{WAF1/Cip1}$, $p27^{kip1}$, MDM2, Bad, ASK1 and IKK□□etc. It is next examined whether API-2 inhibits downstream targets of Akt. As anti-phospho-tuberlin, -Bad, -AFX, and -GSK-3β antibodies are commercially available, therefore, the effect of API-2 on their phosphorylation induced by Akt was determined. Following API-2 (1 µM) treatment, OVCAR3 cells was lysed and immunoblotted with the individual antiphospho-antibody. FIG. 4A shows that API-2 considerably inhibited the phosphorylation levels of tuberlin leading to stabilization and upregulation of tuberin (Dan, H. C., et al., J Biol Chem, 2002. 277: p. 35364-35370). The phosphorylation levels of Bad, GSK-3β, and AFX are partially attenuated by API-2. These data suggest that API-2 induces cell death and cell growth arrest by inhibiting phosphorylation of its downstream targets. API-2 inhibition of Akt downstream targets at different degrees could be due to the fact that phosphorylation sites of these targets are also regulated by other kinase(s), for instance, Bad serine-136 is phosphorylated by PAK1 in addition to Akt (Schurmann, A., et al. Mol Cell Biol, 2000. 20: p. 453-461).

Example 2: Antitumor Activity in the Nude Mouse Tumor Xenograft Model

Tumor cells can be harvested, suspended in PBS, and can be injected s.c. into the right and left flanks ($2\times10^6$ cells/flank) of 8-week-old female nude mice as reported previously (Sun, J. et al., Cancer Res, 1999. 59: p. 4919-4926, 1999). When tumors reach about 100-150 mm$^3$, animals are randomized and dosed i.p. with 0.2 ml vehicle of the triciribine compound and/or an erlotinib-like compound, for example, gefitinib, erlotinib or a salt thereof, daily. Control animals receive DMSO (20%) vehicle, whereas treated animals can be injected with API-2 (1 mg/kg/day) in 20% DMSO.

API-2 Inhibits the Growth of Tumors in Nude Mice that Overexpress Akt.

Frequent overexpression/activation and/or amplification of AKT1 and AKT2 in human ovarian and pancreatic cancer was shown (Cheng J. Q. and Nicosia S. V., in *Encyclopedic Reference of Cancer*, 2001, Schwab D, Ed. Springer, Berlin Heidelberg and New York, p. 35-7). Inhibition of Akt pathway by inhibitors of PI3K, HSP70, Src and farnesyltransferase resulted in cell growth arrest and induction of apoptosis (Solit D. B. et al., Cancer Res, 2003. 63: p. 2139-2144; Xu, W., et al. Cancer Res, 2003.63: p. 7777-7784). A recent study showed that the tumor growth of xenografts with elevated Akt was also significantly inhibited by intratumoral injection of adenovirus of dominant negative Akt (Jetzt A. et al., Cancer Res, 2003. 63: p. 697-706, 2003). Because API-2 inhibits Akt signaling and induces apoptosis and cell growth arrest only in cancer cells with elevated levels of Akt (FIG. 3), the growth of tumors with elevated levels of Akt should be more sensitive to API-2 than that of tumors with low levels of Akt in nude mice. To this end, s.c. Akt-overexpressing cells (OVCAR3, OVCAR8 and PANC-1) are s.c. implanted into the right flank, and those cell lines that express low levels of Akt (OVCAR5 and COLO357) into the left flank of mice. When the tumors reach an average size of about 100-150 mm$^3$, the animals are randomized and treated i.p. with either vehicle or API-2 (1 mg/kg/day). As illustrated in FIG. 4B, OVCAR-5 and COLO357 tumors treated with vehicle grew to about 800-1,000 mm$^3$ 49 days after tumor implantation. OVCAR3, OVCAR8 and PANC1 tumors treated with vehicle control grew to about 700-900 mm$^3$ 49 days after tumor implantation. API-2 inhibited OVCAR3, OVCAR8 and PANC1 tumor growth by 90%, 88% and 80%, respectively. In contrast, API-2 has little effect on the growth of OVCAR5 and COLO357 cells in nude mice (FIGS. 4B-4D and data not shown). At dose 1 mg/kg/day, API-2 had no effects on blood glucose level, body weight, activity and food intake of mice. In treated tumor samples, Akt activity was inhibited by API-2 without change of total Akt content (FIG. 4E). Taken together, these results indicate that API-2 selectively inhibits the growth of tumors with elevated levels of Akt.

Example 3: TCN Directly Inhibits Wild Type Akt Kinase Activity

API-2 (TCN) can directly inhibit wild type Akt kinase activity induced by PDK1 in vitro (FIG. 1). This result supports that API-2 is a direct Akt inhibitor and that the underlying mechanism may be API-2 binding to PH domain and/or threonine-308 of Akt. An in vitro kinase assay is performed with recombinant of PDK1 and Akt in a kinase buffer containing phosphatidylinositol-3,4,5-P3 (PIP3), API-2 and histone H2B as substrate. After incubation of 30 min, the reactions were separated by SDS-PAGE and exposed in a film.

Example 4: TCN is Effective in Cancer Resistant Cells

The effects of TCN (API-2) are tested in cisplatin, paclitaxel, and tamoxifen resistant A270CP, C-13, OVCAR433 and MCF7/TAM cells. API-2 overcame cisplatin, paclitaxel, and tamoxifen resistance in these cells.

Example 5: TCN Potentiates Growth Inhibition by Trastuzumab and Induces Apoptosis Materials and Methods
Cell Lines and Cell Cultures.
The tumorigenic BT474.ml subline maintained in Dulbecco's modified Eagle's medium: Ham's F-12 medium (1:1) with 8-10% FBS.
Antibodies and Reagents.
Trastuzumab was a gift from Genentech (San Francisco, Calif.). RAD001 (everolimus) was a gift from Novartis (East Hanover, N.J.). QLT0267 and KP 372-1 were gifts from QLT Inc. (Vancouver, BC). Triciribine (6-Amino4-methyl-8-((3-D-ribofuranosyl)-4H,8H-pyrrolo[4,3,2-de]pyrimido [4,5-c] pyridazine) was purchased from Berry & Associates, Inc. (Ann Arbor, Mich.). Edelfosine was purchased from Calbiochem (San Diego, Calif.). A selective Akt inhibitor, 4ADPIB (4-amino-2(3,4-dichloro-phenyl)-N-(1H-indazol-5-yl)-butyramide) (U.S. Pat. No. 6,919,340), was synthesized. PTEN antibodies were from Santa Cruz Biotechnology (Santa Cruz, Calif.). 3-actin antibodies were from Sigma (St. Louis, Mo.). All other antibodies were purchased from Cell Signaling Technology (Danvers, Mass.).
PTEN Antisense and Non-Specific Oligonucleotide Transient Transfection.
Antisense (AS) oligonucleotides specific for PTEN, control non-specific (NS) oligonucleotides and procedures for transfection were followed according to Nagata Y. et al., Cancer Cell, 2004. 6(2): p. 117-27.
Cell Proliferation Assay.
PTEN AS/NS transfected BT474.ml cells were plated 2500 cells/0.32 cm$^2$ well. Cells were treated with inhibitors of the Akt/mTOR pathway alone or in combination with trastuzumab as described for 5 days and viable cells were measured by MTS assay using the CellTiter 96 AQ nonradioactive cell proliferation assay kits according to the manufacturer's protocol (Promega, Madison, Wis.). Treated cells were compared to control DMSO treated BT474.ml cells to calculate percentage of growth inhibition.

APO-BRDU TUNEL Assay.

The PTEN AS and NS transfected BT474.ml cells were plated in 6-well plates (4-6×10⁵ cells/well). Twenty-four hours after plating, the cells were treated as indicated for 72 hours with trastuzumab, TCN and/or RAD001. The floating and adherent cells were collected, labeled and stained using the APO-BRDU™ TUNEL assay kit (Phoenix Flow Systems, San Diego, Calif.) according to the manufacturer's protocol. Data was collected and analyzed using a FACScan flow cytometer and CellQuest Pro 4.02 software (Becton Dickinson, Franklin Lakes, N.J.). At least 10,000 events were examined.

SDS-PAGE and Immunoblot Analysis.

Cells transfected with PTEN AS/NS oligonucleotides were treated as indicated. Immunoblotting was performed as described by Nagata Y. et al., Cancer Cell, 2004. 6(2): p. 117-27.

Results

Triciribine and RAD001 Potentiate Growth Inhibition by Trastuzumab in PTEN-Deficient Cells.

To find a strategy to overcome trastuzumab resistance, particularly resistance caused by PTEN loss, 6 different small molecule inhibitors were tested, which directly or indirectly targeted the PI3K/Akt/mTOR signal transduction pathway, a major pathway activated by overexpression of ErbB2 and the loss of PTEN. The goal was to identify compounds that would exhibit synergistic effects with trastuzumab, preferably at a low dose of the compound in order to minimize toxicity. The drugs chosen targeted Akt, mTOR and integrin-linked kinase (ILK) (FIG. 9A). BT474.ml cells are a tumorigenic subline of the BT474 breast cancer cell line and express high levels of ErbB2. When PTEN levels are decreased by transfection with PTEN antisense oligonucleotides (PTEN AS), BT474.ml breast cancer cells become more resistant to the anti-proliferative effects of trastuzumab than cells with normal levels of PTEN and provide a good experimental model for breast cancers in which trastuzumab resistance is caused by PTEN loss (Nagata Y. et al., Cancer Cell, 2004. 6(2): p. 117-27 and FIGS. 9B and 9C). Nonspecific oligonucleotides (NS) were transfected as controls. Treatment with PTEN AS oligonucleotides effectively lowered PTEN levels (FIGS. 11A and 11B). Neither PTEN AS nor NS control oligonucleotides altered ErbB2 levels in the cells.

PTEN AS and NS-transfected BT474.ml cells were treated with each of the 6 compounds or trastuzumab alone and in combination for 5 days and evaluated cell proliferation as compared to DMSO-treated control. Using growth inhibition as a biological endpoint, we compared the ability of each drug to exhibit cooperative effects with trastuzumab using doses of drug that resulted in ~20-40% growth inhibition when administered alone (FIG. 9A).

Almost all of the compounds displayed growth inhibitory effects, particularly at high concentrations and in cells with intact PTEN (FIG. 9A). However, two of the compounds, triciribine and RAD001, markedly enhanced growth inhibition in the PTEN AS cells when combined with trastuzumab as compared to trastuzumab or either compound alone (FIG. 9A). Triciribine (also called API-2), a compound that inhibits Akt activation, potentiated growth inhibition by trastuzumab over a 20-fold concentration range (FIG. 9B). The mTOR inhibitor RAD001 (everolimus) increased growth inhibition by trastuzumab when RAD001 was administered at low doses (<1 nM) (FIG. 9C). Strikingly, triciribine and RAD001 were able to cooperate with trastuzumab to inhibit cell growth at similar levels in the PTEN AS and NS cells (FIGS. 9B and 9C). In essence, triciribine and RAD001 were able to restore trastuzumab sensitivity to PTEN-deficient cells. Triciribine and RAD001 were also effective as single agents, both in PTEN AS and NS cells, at doses greater than 5 mM and 1.5 nM for triciribine and RAD001, respectively (FIGS. 9B and 9C).

A third compound, the ILK inhibitor QLT0267, potentiated growth inhibition by trastuzumab within a narrow dose range (~5-15 pM)(FIG. 9A). Because the dose range in which QLT0267 exhibited cooperative effects with trastuzumab was narrow, this compound further was not investigated further. At concentrations greater than 20 pM, QLT0267 had no cooperative effect with trastuzumab but significantly inhibited cell growth as a single agent.

Induction of Apoptosis Following Combination Treatment.

To assess if growth inhibition was accompanied by apoptosis, we treated PTEN AS and NS transfected BT474.ml cells with triciribine, RAD001 and trastuzumab, alone or combined, and quantified the levels of apoptosis (FIG. 10). RAD001 did not significantly induce apoptosis alone or in combination with trastuzumab. Although the number of TUNEL-positive, apoptotic cells increased slightly following treatment with trastuzumab or triciribine alone, this increase was not statistically significant. However, the combination of triciribine and trastuzumab, significantly induced apoptosis as compared with all other treatments in both PTEN AS and NS transfected cells (FIG. 10).

Example 6: TCN Inhibits Activation of Akt and mTOR Inhibition of Downstream Signaling Molecules Immunoblot analysis verified that triciribine and RAD001 blocked activation of Akt and mTOR, important signaling molecules activated by ErbB2 and the targets of triciribine and RAD001 respectively. Phosphorylation of Akt on Thr308 and Ser473 was analyzed as an indicator of Akt activity and mTOR activity was assessed by the phosphorylation of p70S6K (70-kDa ribosomal protein S6 kinase), an mTOR target. After triciribine treatment, phosphorylation of Akt on both sites was substantially decreased (FIG. 11A). In PTEN-deficient cells, the levels of Akt phosphorylation following triciribine and trastuzumab combination treatment were similar to those seen in cells with intact PTEN (FIG. 11A, lanes 4&8). Thus, triciribine overcame the adverse effects of PTEN loss by effectively blocking Akt activation. RAD001 dramatically blocked phosphorylation of p70S6K (FIG. 11B). However, RAD001 combined with trastuzumab did not lower p70S6K phosphorylation beyond that seen with RAD001 alone (FIG. 11B). A feedback loop has been recently identified which results in Akt phosphorylation and activation following treatment with mTOR inhibitors, such as RAD001 (O'Reilly K. E. et al., Cancer Res, 2006. 66(3): p. 1500-8). It was also observed that feedback activation of Akt by RAD001 and combination therapy with trastuzumab and RAD001 eliminated Akt phosphorylation by this feedback loop (FIG. 11B, lanes 3 vs. 4), consistent with the notion that Akt activation following mTOR inhibition is dependent on upstream receptor tyrosine kinases (O'Reilly K. E. et al., Cancer Res, 2006. 66(3): p. 1500-8). In summary, both drugs inhibited their predicted target kinases and combination treatment had a larger inhibitory effect on the Akt/mTOR signaling pathway than any single agent, even in PTEN-deficient cells.

Example 7: TCN and Trastuzumab Inhibit Tumor Growth in PTEN-Deficient Tumors Materials and Methods
Xenograft Human Tumor Model in SCID Mice.
Female, 6-week-old, severe combined immunodeficiency (SCID) mice were from Taconic Farms (Hudson, N.Y.). Tumor xenografts were performed as described in Nagata Y. et al., Cancer Cell, 2004. 6(2): p. 117-27. When the xenograft tumors reached the average size of 100-150 mm$^3$, the mice were divided into 6 groups, each with 7 mice and an even distribution of tumor sizes, and treated as follows. PTEN antisense (30 pg) oligonucleotides were administered to each mouse weekly via intratumor injection. One week after PTEN AS oligonucleotide administration was initiated, drug treatment began. Trastuzumab was given at a dose of 0.5 mg/kg twice a week in 200 pL saline through intratumor injection at multiple sites. Triciribine was given at a dose of 0.5 mg/kg/day in 200 pL 20% DMSO saline solution through intraperitoneal (I.P.) injection. RAD001 was given via gavage at a dose of 1 pg/kg in 500 pL 5% glucose water twice a week. 20% DMSO saline solution (200 pL/day) was given through I.P. injection. The tumors were measured twice weekly with calipers and the volume of the tumors was calculated as: volume=length×width$^2$/2.

Statistical Analysis.
One-way ANOVA was performed using GraphPad Prism 3.0 for Windows (Graph Pad Software, San Diego, Calif.).

Results
The earlier biological and molecular data were very promising, however, in vivo studies provide the most stringent test for therapeutic efficacy. Therefore, triciribine and RAD001 were tested in vivo. BT474.ml cell xenografts were injected into the mammary fat pad of 6-week-old SCID mice. After tumors formed, the mice received PTEN AS weekly via intratumor injection. This protocol effectively models PTEN-deficient tumors in vivo (Nagata Y. et al., Cancer Cell, 2004. 6(2): p. H7-27). The mice were randomized into treatment groups receiving triciribine, RAD001, trastuzumab or DMSO alone or in combination. After treatment, the growth patterns of the tumors treated with DMSO, trastuzumab, RAD001, or triciribine alone were similar (FIGS. 12A and 12B). Growth of the tumors was not inhibited and the mice were euthanized after 3 weeks due to large tumor burdens. In contrast, combination treatment with triciribine and trastuzumab dramatically and significantly inhibited tumor growth (FIG. 12A). Many of the tumors actually decreased in size and four of 7 mice had no palpable tumors after 5 weeks of treatment. Following treatment with RAD001 and trastuzumab, tumor growth was relatively slower compared to RAD001 or trastuzumab alone (FIG. 12B). Thus combining trastuzumab with triciribine or RAD001 effectively inhibited ErbB2-overexpressing, PTEN-deficient human breast cancer xenografts in vivo.

This invention has been described with reference to its preferred embodiments. Variations and modifications of the invention will be obvious to those skilled in the art from the foregoing detailed description of the invention. It is intended that all of these variations and modifications be included within the scope of this invention.

---

What is claimed is:

1. A method for treating a subject having a tumor or cancer, which tumor or cancer overexpresses AKT kinase comprising:

a. administering to said subject:

i. at least one compound of formula I selected from the group consisting of the following compounds:

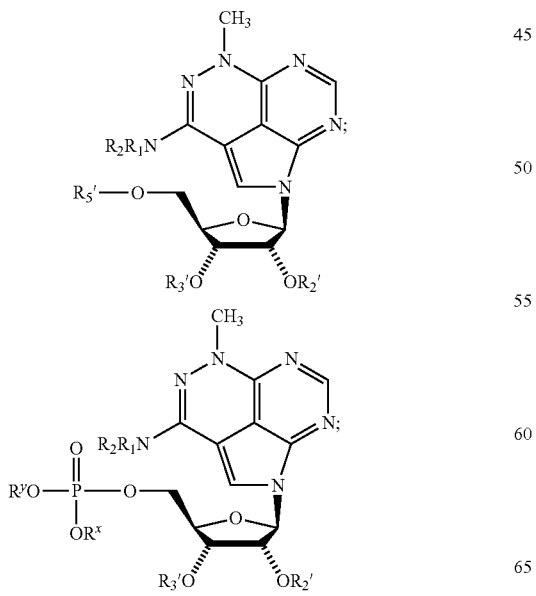

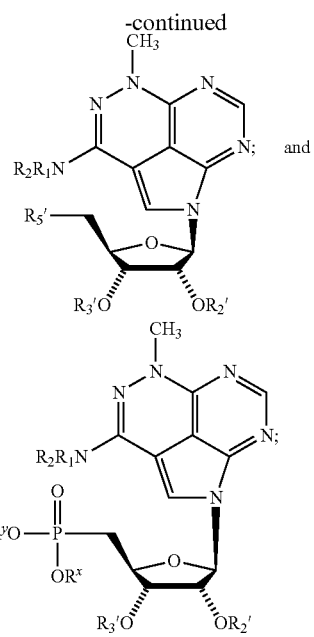

wherein each $R_2'$, $R_3'$, and $R_5'$ is independently hydrogen; optionally substituted phosphate or phosphonate; mono-, di-, or triphosphate; acyl; lower acyl; alkyl; lower alkyl; amide; sulfonate ester; alkyl sulfonate ester; arylalkyl sulfonate ester; sulfonyl; methanesulfonyl; benzyl sulfonyl, wherein the phenyl group of said benzyl is optionally substituted with one or more halo, hydroxyl, amino, alkylamino, arylamino, alkoxy, aryloxy, nitro, cyano, sulfonic acid, sulfate, phosphonic acid, phosphate, or phosphonate; optionally substituted arylsulfonyl; a lipid; phospholipid; an amino acid; a carbohydrate; a peptide; or cholesterol; or other pharmaceutically acceptable leaving group that, in vivo, provides a compound of said formula I wherein $R_2'$, $R_3'$ or $R_5'$ is independently H or mono-, di- or tri-phosphate;

wherein $R^x$ and $R^y$ are independently hydrogen; optionally substituted phosphate; acyl; lower acyl; amide; alkyl; lower alkyl; aromatic; polyoxyalkylene; polyethyleneglycol; optionally substituted arylsulfonyl; a lipid; a phospholipid; an amino acid; a carbohydrate; a peptide; or cholesterol; or other pharmaceutically acceptable leaving group; and wherein $R_1$ and $R_2$ each are independently H, optionally substituted straight chained, branched or cyclic alkyl, lower alkyl, alkenyl, or alkynyl, CO-alkyl, CO-alkenyl, CO-alkynyl, CO-aryl or heteroaryl, CO-alkoxyalkyl, CO-aryloxyalkyl, CO-substituted aryl, sulfonyl, alkylsulfonyl, arylsulfonyl, or aralkylsulfonyl;

ii. one or more epidermal growth factor receptor inhibitors or a salt thereof; and iii. a pharmaceutically acceptable carrier, wherein the amount of compound of formula I administered to said subject is at least 2 mg/m$^2$.

2. The method of claim 1, wherein the compound of formula I is triciribine.

3. The method of claim 1, wherein the compound of formula I is triciribine phosphate.

4. The method of claim 1, wherein the compound of formula I is triciribine phosphonate.

5. The method of claim 1, wherein the compound of formula I is present in a dose amount of at least 20 mg/m$^2$.

6. The method of claim 1, wherein the compound of formula I is present in an amount of at least 10 mg/m$^2$.

7. The method of claim 1, wherein the administration is parenteral administration.

8. The method of claim 7, wherein the parenteral administration is intravenous administration.

9. The method of claim 1, wherein the administration is oral administration.

10. The method of claim 1, suitable for intravenous administration.

11. The method of claim 1, wherein the epidermal growth factor receptor inhibitor compound or salt thereof is present in a dose about 0.1 mg/m$^2$ to about 200 mg/m$^2$.

12. The method of claim 1, wherein the epidermal growth factor receptor inhibitor compound or salt thereof is present in a dose about 1 mg/m$^2$ to about 150 mg/m$^2$.

13. The method of claim 1, wherein the epidermal growth factor receptor inhibitor compound or salt thereof is present in a dose about 10 mg/m$^2$ to about 100 mg/m$^2$.

14. The method of claim 1, wherein the epidermal growth factor receptor inhibitor compound or salt thereof is present in a dose about 25 mg/m$^2$ to about 50 mg/m$^2$.

15. The method of claim 1, wherein the administration of a compound of formula I and epidermal growth factor receptor inhibitor compound or salt thereof is concurrently administered.

16. The method of claim 1, wherein the administration of a compound of formula I is followed by the administration of epidermal growth factor receptor inhibitor compound or salt thereof.

17. The method of claim 1, wherein the administration of epidermal growth factor receptor inhibitor compound or salt thereof is followed by the administration of a compound of formula I.

18. The method of claim 1, wherein the epidermal growth factor receptor inhibitor is gefitinib.

19. The method of claim 1, wherein the epidermal growth factor receptor inhibitor is erlotinib.

* * * * *

UNITED STATES PATENT AND TRADEMARK OFFICE
CERTIFICATE OF CORRECTION

PATENT NO. : 9,655,914 B2
APPLICATION NO. : 14/998352
DATED : May 23, 2017
INVENTOR(S) : Jin Q. Cheng et al.

It is certified that error appears in the above-identified patent and that said Letters Patent is hereby corrected as shown below:

In the Specification

Column 1, Lines 19-24 should read:
-- STATEMENT REGARDING FEDERALLY SPONSORED RESEARCH
This invention was made with government support CA077935 and CA089242 awarded by the National Institutes of Health. The Government has certain rights in this invention. --

Signed and Sealed this
Fifteenth Day of May, 2018

Andrei Iancu
*Director of the United States Patent and Trademark Office*

SEQUENCE LISTING

```
<160> NUMBER OF SEQ ID NOS: 6

<210> SEQ ID NO 1
<211> LENGTH: 1443
<212> TYPE: DNA
<213> ORGANISM: Homo sapiens
<220> FEATURE:
<221> NAME/KEY: CDS
<222> LOCATION: (1)..(1443)

<400> SEQUENCE: 1 atg aac gac gta gcc att gtg aag gag ggc tgg ctg cac aaa cga ggg      48
Met Asn Asp Val Ala Ile Val Lys Glu Gly Trp Leu His Lys Arg Gly
1               5                   10                  15 gaa tat att aaa acc tgg cgg cca cgc tac ttc ctc ctc aag aac gat      96
Glu Tyr Ile Lys Thr Trp Arg Pro Arg Tyr Phe Leu Leu Lys Asn Asp
            20                  25                  30 ggc acc ttt att ggc tac aag gaa cgg cct cag gat gtg gat cag cga     144
Gly Thr Phe Ile Gly Tyr Lys Glu Arg Pro Gln Asp Val Asp Gln Arg
        35                  40                  45 gag tcc cca ctc aac aac ttc tca gtg gca caa tgc cag ctg atg aag     192
Glu Ser Pro Leu Asn Asn Phe Ser Val Ala Gln Cys Gln Leu Met Lys
    50                  55                  60 aca gag cgg cca agg ccc aac acc ttt atc atc cgc tgc ctg cag tgg     240
Thr Glu Arg Pro Arg Pro Asn Thr Phe Ile Ile Arg Cys Leu Gln Trp
65                  70                  75                  80 acc aca gtc att gag cgc acc ttc cat gta gaa acg cct gag gag cgg     288
Thr Thr Val Ile Glu Arg Thr Phe His Val Glu Thr Pro Glu Glu Arg
                85                  90                  95 gaa gaa tgg gcc acc gcc att cag act gtg gcc gat gga ctc aag agg     336
```

|   |   |   |   |   |   |   |   |   |   |   |   |   |   |   |   |   |
|---|---|---|---|---|---|---|---|---|---|---|---|---|---|---|---|---|
| Glu | Glu | Trp | Ala | Thr | Ala | Ile | Gln | Thr | Val | Ala | Asp | Gly | Leu | Lys | Arg | |
|   |   |   | 100 |   |   |   | 105 |   |   |   | 110 |   |   |   |   | |

| cag | gaa | gaa | gag | acg | atg | gac | ttc | cga | tca | ggc | tca | ccc | agt | gac | aac | 384 |
|-----|-----|-----|-----|-----|-----|-----|-----|-----|-----|-----|-----|-----|-----|-----|-----|-----|
| Gln | Glu | Glu | Glu | Thr | Met | Asp | Phe | Arg | Ser | Gly | Ser | Pro | Ser | Asp | Asn | |
|   |   |   | 115 |   |   |   | 120 |   |   |   | 125 |   |   |   |   | |

| tca | ggg | gct | gaa | gag | atg | gag | gtg | tcc | ctg | gcc | aag | ccc | aag | cac | cgt | 432 |
| Ser | Gly | Ala | Glu | Glu | Met | Glu | Val | Ser | Leu | Ala | Lys | Pro | Lys | His | Arg | |
| 130 |   |   |   |   | 135 |   |   |   |   | 140 |   |   |   |   |   | |

| gtg | acc | atg | aac | gag | ttt | gag | tac | ctg | aaa | cta | ctg | ggc | aag | ggc | acc | 480 |
| Val | Thr | Met | Asn | Glu | Phe | Glu | Tyr | Leu | Lys | Leu | Leu | Gly | Lys | Gly | Thr | |
| 145 |   |   |   |   | 150 |   |   |   |   | 155 |   |   |   |   | 160 | |

| ttt | ggg | aaa | gtg | att | ctg | gta | aaa | gag | aag | gcc | aca | ggc | cgc | tac | tat | 528 |
| Phe | Gly | Lys | Val | Ile | Leu | Val | Lys | Glu | Lys | Ala | Thr | Gly | Arg | Tyr | Tyr | |
|   |   |   |   | 165 |   |   |   |   | 170 |   |   |   |   | 175 |   | |

| gcc | atg | aag | atc | ctc | aag | aag | gag | gtc | atc | gtc | gcc | aag | gat | gag | gtt | 576 |
| Ala | Met | Lys | Ile | Leu | Lys | Lys | Glu | Val | Ile | Val | Ala | Lys | Asp | Glu | Val | |
|   |   |   | 180 |   |   |   |   | 185 |   |   |   | 190 |   |   |   | |

| gcc | cac | acg | ctt | act | gaa | aac | cgt | gtc | ctg | cag | aac | tct | agg | cat | ccc | 624 |
| Ala | His | Thr | Leu | Thr | Glu | Asn | Arg | Val | Leu | Gln | Asn | Ser | Arg | His | Pro | |
|   |   | 195 |   |   |   |   | 200 |   |   |   |   | 205 |   |   |   | |

| ttc | ctt | acg | gcc | ctc | aag | tac | tca | ttc | cag | acc | cac | gac | cgc | ctc | tgc | 672 |
| Phe | Leu | Thr | Ala | Leu | Lys | Tyr | Ser | Phe | Gln | Thr | His | Asp | Arg | Leu | Cys | |
|   | 210 |   |   |   |   | 215 |   |   |   |   | 220 |   |   |   |   | |

| ttt | gtc | atg | gag | tat | gcc | aac | ggg | ggc | gag | ctc | ttc | ttc | cac | ctg | tct | 720 |
| Phe | Val | Met | Glu | Tyr | Ala | Asn | Gly | Gly | Glu | Leu | Phe | Phe | His | Leu | Ser | |
| 225 |   |   |   |   | 230 |   |   |   |   | 235 |   |   |   |   | 240 | |

| cga | gag | cgc | gtg | ttc | tcc | gag | gac | cgg | gcc | cgc | ttc | tat | ggt | gcg | gag | 768 |
| Arg | Glu | Arg | Val | Phe | Ser | Glu | Asp | Arg | Ala | Arg | Phe | Tyr | Gly | Ala | Glu | |
|   |   |   |   | 245 |   |   |   |   | 250 |   |   |   |   | 255 |   | |

| att | gtg | tct | gcc | ctg | gac | tac | ttg | cac | tcg | gag | aag | aac | gtg | gtg | tac | 816 |
| Ile | Val | Ser | Ala | Leu | Asp | Tyr | Leu | His | Ser | Glu | Lys | Asn | Val | Val | Tyr | |
|   |   |   | 260 |   |   |   |   | 265 |   |   |   | 270 |   |   |   | |

| cgg | gac | ctg | aag | cta | gag | aac | ctc | atg | ctg | gac | aag | gac | ggg | cac | atc | 864 |
| Arg | Asp | Leu | Lys | Leu | Glu | Asn | Leu | Met | Leu | Asp | Lys | Asp | Gly | His | Ile | |
|   |   | 275 |   |   |   |   | 280 |   |   |   |   | 285 |   |   |   | |

| aag | ata | acg | gac | ttc | ggg | ctg | tgc | aag | gag | ggg | atc | aag | gat | ggt | gcc | 912 |
| Lys | Ile | Thr | Asp | Phe | Gly | Leu | Cys | Lys | Glu | Gly | Ile | Lys | Asp | Gly | Ala | |
|   | 290 |   |   |   |   | 295 |   |   |   |   | 300 |   |   |   |   | |

| act | atg | aag | aca | ttc | tgc | gga | acg | ccg | gag | tac | ctg | gcc | cct | gag | gtg | 960 |
| Thr | Met | Lys | Thr | Phe | Cys | Gly | Thr | Pro | Glu | Tyr | Leu | Ala | Pro | Glu | Val | |
| 305 |   |   |   |   | 310 |   |   |   |   | 315 |   |   |   |   | 320 | |

| ctg | gaa | gac | aac | gac | tac | ggc | cgt | gca | gtg | gac | tgg | tgg | ggg | ctg | ggc | 1008 |
| Leu | Glu | Asp | Asn | Asp | Tyr | Gly | Arg | Ala | Val | Asp | Trp | Trp | Gly | Leu | Gly | |
|   |   |   |   | 325 |   |   |   |   | 330 |   |   |   |   | 335 |   | |

| gtg | gtc | atg | tat | gag | atg | atg | tgt | ggc | cgc | ctg | ccc | ttc | tac | aac | cag | 1056 |
| Val | Val | Met | Tyr | Glu | Met | Met | Cys | Gly | Arg | Leu | Pro | Phe | Tyr | Asn | Gln | |
|   |   |   | 340 |   |   |   |   | 345 |   |   |   |   | 350 |   |   | |

| gac | cac | gag | aag | ctg | ttc | gag | ctg | atc | ctc | atg | gag | gag | atc | cgc | ttc | 1104 |
| Asp | His | Glu | Lys | Leu | Phe | Glu | Leu | Ile | Leu | Met | Glu | Glu | Ile | Arg | Phe | |
|   |   | 355 |   |   |   |   | 360 |   |   |   |   | 365 |   |   |   | |

| ccg | cgc | aca | ctc | ggc | cct | gag | gcc | aag | tcc | ctg | ctc | tcc | ggg | ctg | ctc | 1152 |
| Pro | Arg | Thr | Leu | Gly | Pro | Glu | Ala | Lys | Ser | Leu | Leu | Ser | Gly | Leu | Leu | |
|   | 370 |   |   |   |   | 375 |   |   |   |   | 380 |   |   |   |   | |

| aag | aag | gac | cct | aca | cag | agg | ctc | ggt | ggg | ggc | tct | gag | gat | gcc | aag | 1200 |
| Lys | Lys | Asp | Pro | Thr | Gln | Arg | Leu | Gly | Gly | Gly | Ser | Glu | Asp | Ala | Lys | |
| 385 |   |   |   |   | 390 |   |   |   |   | 395 |   |   |   |   | 400 | |

| gag | atc | atg | cag | cac | cgg | ttc | ttt | gcc | aac | atc | gtg | tgg | cag | gat | gtg | 1248 |
| Glu | Ile | Met | Gln | His | Arg | Phe | Phe | Ala | Asn | Ile | Val | Trp | Gln | Asp | Val | |
|   |   |   |   | 405 |   |   |   |   | 410 |   |   |   |   | 415 |   | |

| | | | | | | | | | | | | | | | |
|---|---|---|---|---|---|---|---|---|---|---|---|---|---|---|---|
| tat | gag | aag | aag | ctg | agc | cca | cct | ttc | aag | ccc | cag | gtc | acc | tct | gag |
| Tyr | Glu | Lys | Lys | Leu | Ser | Pro | Pro | Phe | Lys | Pro | Gln | Val | Thr | Ser | Glu |
| | | | 420 | | | | 425 | | | | 430 | | | | |

1296

| | | | | | | | | | | | | | | | |
|---|---|---|---|---|---|---|---|---|---|---|---|---|---|---|---|
| act | gac | acc | agg | tat | ttc | gat | gag | gag | ttc | aca | gct | cag | atg | atc | acc |
| Thr | Asp | Thr | Arg | Tyr | Phe | Asp | Glu | Glu | Phe | Thr | Ala | Gln | Met | Ile | Thr |
| | | 435 | | | | | 440 | | | | 445 | | | | |

1344

| | | | | | | | | | | | | | | | |
|---|---|---|---|---|---|---|---|---|---|---|---|---|---|---|---|
| atc | acg | ccg | cct | gat | caa | gat | gac | agc | atg | gag | tgt | gtg | gac | agt | gag |
| Ile | Thr | Pro | Pro | Asp | Gln | Asp | Asp | Ser | Met | Glu | Cys | Val | Asp | Ser | Glu |
| 450 | | | | | 455 | | | | 460 | | | | | | |

1392

| | | | | | | | | | | | | | | | |
|---|---|---|---|---|---|---|---|---|---|---|---|---|---|---|---|
| cgg | agg | ccg | cac | ttc | ccc | cag | ttc | tcc | tac | tca | gcc | agt | ggc | aca | gcc |
| Arg | Arg | Pro | His | Phe | Pro | Gln | Phe | Ser | Tyr | Ser | Ala | Ser | Gly | Thr | Ala |
| 465 | | | | 470 | | | | | 475 | | | | | 480 | |

1440 tga    1443

<210> SEQ ID NO 2
<211> LENGTH: 480
<212> TYPE: PRT
<213> ORGANISM: Homo sapiens

<400> SEQUENCE: 2

Met Asn Asp Val Ala Ile Val Lys Glu Gly Trp Leu His Lys Arg Gly
1               5                   10                  15

Glu Tyr Ile Lys Thr Trp Arg Pro Arg Tyr Phe Leu Leu Lys Asn Asp
            20                  25                  30

Gly Thr Phe Ile Gly Tyr Lys Glu Arg Pro Gln Asp Val Asp Gln Arg
        35                  40                  45

Glu Ser Pro Leu Asn Asn Phe Ser Val Ala Gln Cys Gln Leu Met Lys
    50                  55                  60

Thr Glu Arg Pro Arg Pro Asn Thr Phe Ile Ile Arg Cys Leu Gln Trp
65                  70                  75                  80

Thr Thr Val Ile Glu Arg Thr Phe His Val Glu Thr Pro Glu Glu Arg
                85                  90                  95

Glu Glu Trp Ala Thr Ala Ile Gln Thr Val Ala Asp Gly Leu Lys Arg
            100                 105                 110

Gln Glu Glu Glu Thr Met Asp Phe Arg Ser Gly Ser Pro Ser Asp Asn
        115                 120                 125

Ser Gly Ala Glu Glu Met Glu Val Ser Leu Ala Lys Pro Lys His Arg
    130                 135                 140

Val Thr Met Asn Glu Phe Glu Tyr Leu Lys Leu Leu Gly Lys Gly Thr
145                 150                 155                 160

Phe Gly Lys Val Ile Leu Val Lys Glu Lys Ala Thr Gly Arg Tyr Tyr
                165                 170                 175

Ala Met Lys Ile Leu Lys Lys Glu Val Ile Val Ala Lys Asp Glu Val
            180                 185                 190

Ala His Thr Leu Thr Glu Asn Arg Val Leu Gln Asn Ser Arg His Pro
        195                 200                 205

Phe Leu Thr Ala Leu Lys Tyr Ser Phe Gln Thr His Asp Arg Leu Cys
    210                 215                 220

Phe Val Met Glu Tyr Ala Asn Gly Gly Glu Leu Phe Phe His Leu Ser
225                 230                 235                 240

Arg Glu Arg Val Phe Ser Glu Asp Arg Ala Arg Phe Tyr Gly Ala Glu
                245                 250                 255

Ile Val Ser Ala Leu Asp Tyr Leu His Ser Glu Lys Asn Val Val Tyr
            260                 265                 270

Arg Asp Leu Lys Leu Glu Asn Leu Met Leu Asp Lys Asp Gly His Ile
        275                 280                 285

```
Lys Ile Thr Asp Phe Gly Leu Cys Lys Glu Gly Ile Lys Asp Gly Ala
        290                 295                 300

Thr Met Lys Thr Phe Cys Gly Thr Pro Glu Tyr Leu Ala Pro Glu Val
305                 310                 315                 320

Leu Glu Asp Asn Asp Tyr Gly Arg Ala Val Asp Trp Trp Gly Leu Gly
                325                 330                 335

Val Val Met Tyr Glu Met Met Cys Gly Arg Leu Pro Phe Tyr Asn Gln
            340                 345                 350

Asp His Glu Lys Leu Phe Glu Leu Ile Leu Met Glu Glu Ile Arg Phe
        355                 360                 365

Pro Arg Thr Leu Gly Pro Glu Ala Lys Ser Leu Leu Ser Gly Leu Leu
    370                 375                 380

Lys Lys Asp Pro Thr Gln Arg Leu Gly Gly Gly Ser Glu Asp Ala Lys
385                 390                 395                 400

Glu Ile Met Gln His Arg Phe Phe Ala Asn Ile Val Trp Gln Asp Val
                405                 410                 415

Tyr Glu Lys Lys Leu Ser Pro Pro Phe Lys Pro Gln Val Thr Ser Glu
            420                 425                 430

Thr Asp Thr Arg Tyr Phe Asp Glu Glu Phe Thr Ala Gln Met Ile Thr
        435                 440                 445

Ile Thr Pro Pro Asp Gln Asp Asp Ser Met Glu Cys Val Asp Ser Glu
    450                 455                 460

Arg Arg Pro His Phe Pro Gln Phe Ser Tyr Ser Ala Ser Gly Thr Ala
465                 470                 475                 480

<210> SEQ ID NO 3
<211> LENGTH: 1515
<212> TYPE: DNA
<213> ORGANISM: Homo sapiens
<220> FEATURE:
<221> NAME/KEY: CDS
<222> LOCATION: (1)..(1446)

<400> SEQUENCE: 3 atg aat gag gtg tct gtc atc aaa gaa ggc tgg ctc cac aag cgt ggt      48
Met Asn Glu Val Ser Val Ile Lys Glu Gly Trp Leu His Lys Arg Gly
1               5                   10                  15 gaa tac atc aag acc tgg agg cca cgg tac ttc ctg ctg aag agc gac      96
Glu Tyr Ile Lys Thr Trp Arg Pro Arg Tyr Phe Leu Leu Lys Ser Asp
            20                  25                  30 ggc tcc ttc att ggg tac aag gag agg ccc gag gcc cct gat cag act     144
Gly Ser Phe Ile Gly Tyr Lys Glu Arg Pro Glu Ala Pro Asp Gln Thr
        35                  40                  45 cta ccc ccc tta aac aac ttc tcc gta gca gaa tgc cag ctg atg aag     192
Leu Pro Pro Leu Asn Asn Phe Ser Val Ala Glu Cys Gln Leu Met Lys
    50                  55                  60 acc gag agg ccg cga ccc aac acc ttt gtc ata cgc tgc ctg cag tgg     240
Thr Glu Arg Pro Arg Pro Asn Thr Phe Val Ile Arg Cys Leu Gln Trp
65                  70                  75                  80 acc aca gtc atc gag agg acc ttc cac gtg gat tct cca gac gag agg     288
Thr Thr Val Ile Glu Arg Thr Phe His Val Asp Ser Pro Asp Glu Arg
                85                  90                  95 gag gag tgg atg cgg gcc atc cag atg gtc gcc aac agc ctc aag cag     336
Glu Glu Trp Met Arg Ala Ile Gln Met Val Ala Asn Ser Leu Lys Gln
            100                 105                 110 cgg gcc cca ggc gag gac ccc atg gac tac aag tgt ggc tcc ccc agt     384
Arg Ala Pro Gly Glu Asp Pro Met Asp Tyr Lys Cys Gly Ser Pro Ser
        115                 120                 125
```

```
gac tcc tcc acg act gag gag atg gaa gtg gcg gtc agc aag gca cgg         432
Asp Ser Ser Thr Thr Glu Glu Met Glu Val Ala Val Ser Lys Ala Arg
        130                 135                 140 gct aaa gtg acc atg aat gac ttc gac tat ctc aaa ctc ctt ggc aag         480
Ala Lys Val Thr Met Asn Asp Phe Asp Tyr Leu Lys Leu Leu Gly Lys
145                 150                 155                 160 gga acc ttt ggc aaa gtc atc ctg gtg cgg gag aag gcc act ggc cgc         528
Gly Thr Phe Gly Lys Val Ile Leu Val Arg Glu Lys Ala Thr Gly Arg
                165                 170                 175 tac tac gcc atg aag atc ctg cga aag gaa gtc atc att gcc aag gat         576
Tyr Tyr Ala Met Lys Ile Leu Arg Lys Glu Val Ile Ile Ala Lys Asp
            180                 185                 190 gaa gtc gct cac aca gtc acc gag agc cgg gtc ctc cag aac acc agg         624
Glu Val Ala His Thr Val Thr Glu Ser Arg Val Leu Gln Asn Thr Arg
        195                 200                 205 cac ccg ttc ctc act gcg ctg aag tat gcc ttc cag acc cac gac cgc         672
His Pro Phe Leu Thr Ala Leu Lys Tyr Ala Phe Gln Thr His Asp Arg
210                 215                 220 ctg tgc ttt gtg atg gag tat gcc aac ggg ggt gag ctg ttc ttc cac         720
Leu Cys Phe Val Met Glu Tyr Ala Asn Gly Gly Glu Leu Phe Phe His
225                 230                 235                 240 ctg tcc cgg gag cgt gtc ttc aca gag gag cgg gcc cgg ttt tat ggt         768
Leu Ser Arg Glu Arg Val Phe Thr Glu Glu Arg Ala Arg Phe Tyr Gly
                245                 250                 255 gca gag att gtc tcg gct ctt gag tac ttg cac tcg cgg gac gtg gta         816
Ala Glu Ile Val Ser Ala Leu Glu Tyr Leu His Ser Arg Asp Val Val
            260                 265                 270 tac cgc gac atc aag ctg gaa aac ctc atg ctg gac aaa gat ggc cac         864
Tyr Arg Asp Ile Lys Leu Glu Asn Leu Met Leu Asp Lys Asp Gly His
        275                 280                 285 atc aag atc act gac ttt ggc ctc tgc aaa gag ggc atc agt gac ggg         912
Ile Lys Ile Thr Asp Phe Gly Leu Cys Lys Glu Gly Ile Ser Asp Gly
    290                 295                 300 gcc acc atg aaa acc ttc tgt ggg acc ccg gag tac ctg gcg cct gag         960
Ala Thr Met Lys Thr Phe Cys Gly Thr Pro Glu Tyr Leu Ala Pro Glu
305                 310                 315                 320 gtg ctg gag gac aat gac tat ggc cgg gcc gtg gac tgg tgg ggg ctg        1008
Val Leu Glu Asp Asn Asp Tyr Gly Arg Ala Val Asp Trp Trp Gly Leu
                325                 330                 335 ggt gtg gtc atg tac gag atg atg tgc ggc cgc ctg ccc ttc tac aac        1056
Gly Val Val Met Tyr Glu Met Met Cys Gly Arg Leu Pro Phe Tyr Asn
            340                 345                 350 cag gac cac gag cgc ctc ttc gag ctc atc ctc atg gaa gag atc cgc        1104
Gln Asp His Glu Arg Leu Phe Glu Leu Ile Leu Met Glu Glu Ile Arg
        355                 360                 365 ttc ccg cgc acg ctc agc ccc gag gcc aag tcc ctg ctt gct ggg ctg        1152
Phe Pro Arg Thr Leu Ser Pro Glu Ala Lys Ser Leu Leu Ala Gly Leu
    370                 375                 380 ctt aag aag gac ccc aag cag agg ctt ggt ggg ggg ccc agc gat gcc        1200
Leu Lys Lys Asp Pro Lys Gln Arg Leu Gly Gly Gly Pro Ser Asp Ala
385                 390                 395                 400 aag gag gtc atg gag cac agg ttc ttc ctc agc atc aac tgg cag gac        1248
Lys Glu Val Met Glu His Arg Phe Phe Leu Ser Ile Asn Trp Gln Asp
                405                 410                 415 gtg gtc cag aag aag ctc ctg cca ccc ttc aaa cct cag gtc acg tcc        1296
Val Val Gln Lys Lys Leu Leu Pro Pro Phe Lys Pro Gln Val Thr Ser
            420                 425                 430 gag gtc gac aca agg tac ttc gat gat gaa ttt acc gcc cag tcc atc        1344
Glu Val Asp Thr Arg Tyr Phe Asp Asp Glu Phe Thr Ala Gln Ser Ile
```

-continued

```
                435                 440                 445
aca atc aca ccc cct gac cgc tat gac agc ctg ggc tta ctg gag ctg      1392
Thr Ile Thr Pro Pro Asp Arg Tyr Asp Ser Leu Gly Leu Leu Glu Leu
450                 455                 460 gac cag cgg acc cac ttc ccc cag ttc tcc tac tcg gcc agc atc cgc      1440
Asp Gln Arg Thr His Phe Pro Gln Phe Ser Tyr Ser Ala Ser Ile Arg
465                 470                 475                 480 gag tga gcagtctgcc cacgcagagg acgcacgctc gctgccatca ccgctgggtg       1496
Glu
gttttttacc cctgcccgg                                                  1515

<210> SEQ ID NO 4
<211> LENGTH: 481
<212> TYPE: PRT
<213> ORGANISM: Homo sapiens

<400> SEQUENCE: 4

Met Asn Glu Val Ser Val Ile Lys Glu Gly Trp Leu His Lys Arg Gly
1               5                  10                  15

Glu Tyr Ile Lys Thr Trp Arg Pro Arg Tyr Phe Leu Leu Lys Ser Asp
                20                  25                  30

Gly Ser Phe Ile Gly Tyr Lys Glu Arg Pro Glu Ala Pro Asp Gln Thr
            35                  40                  45

Leu Pro Pro Leu Asn Asn Phe Ser Val Ala Glu Cys Gln Leu Met Lys
        50                  55                  60

Thr Glu Arg Pro Arg Pro Asn Thr Phe Val Ile Arg Cys Leu Gln Trp
65                  70                  75                  80

Thr Thr Val Ile Glu Arg Thr Phe His Val Asp Ser Pro Asp Glu Arg
                85                  90                  95

Glu Glu Trp Met Arg Ala Ile Gln Met Val Ala Asn Ser Leu Lys Gln
            100                 105                 110

Arg Ala Pro Gly Glu Asp Pro Met Asp Tyr Lys Cys Gly Ser Pro Ser
        115                 120                 125

Asp Ser Ser Thr Thr Glu Glu Met Glu Val Ala Val Ser Lys Ala Arg
130                 135                 140

Ala Lys Val Thr Met Asn Asp Phe Asp Tyr Leu Lys Leu Leu Gly Lys
145                 150                 155                 160

Gly Thr Phe Gly Lys Val Ile Leu Val Arg Glu Lys Ala Thr Gly Arg
                165                 170                 175

Tyr Tyr Ala Met Lys Ile Leu Arg Lys Glu Val Ile Ile Ala Lys Asp
            180                 185                 190

Glu Val Ala His Thr Val Thr Glu Ser Arg Val Leu Gln Asn Thr Arg
        195                 200                 205

His Pro Phe Leu Thr Ala Leu Lys Tyr Ala Phe Gln Thr His Asp Arg
210                 215                 220

Leu Cys Phe Val Met Glu Tyr Ala Asn Gly Gly Glu Leu Phe Phe His
225                 230                 235                 240

Leu Ser Arg Glu Arg Val Phe Thr Glu Glu Arg Ala Arg Phe Tyr Gly
                245                 250                 255

Ala Glu Ile Val Ser Ala Leu Glu Tyr Leu His Ser Arg Asp Val Val
            260                 265                 270

Tyr Arg Asp Ile Lys Leu Glu Asn Leu Met Leu Asp Lys Asp Gly His
        275                 280                 285

Ile Lys Ile Thr Asp Phe Gly Leu Cys Lys Glu Gly Ile Ser Asp Gly
290                 295                 300
```

```
Ala Thr Met Lys Thr Phe Cys Gly Thr Pro Glu Tyr Leu Ala Pro Glu
305                 310                 315                 320

Val Leu Glu Asp Asn Asp Tyr Gly Arg Ala Val Asp Trp Trp Gly Leu
                325                 330                 335

Gly Val Val Met Tyr Glu Met Met Cys Gly Arg Leu Pro Phe Tyr Asn
            340                 345                 350

Gln Asp His Glu Arg Leu Phe Glu Leu Ile Leu Met Glu Glu Ile Arg
        355                 360                 365

Phe Pro Arg Thr Leu Ser Pro Glu Ala Lys Ser Leu Leu Ala Gly Leu
    370                 375                 380

Leu Lys Lys Asp Pro Lys Gln Arg Leu Gly Gly Gly Pro Ser Asp Ala
385                 390                 395                 400

Lys Glu Val Met Glu His Arg Phe Phe Leu Ser Ile Asn Trp Gln Asp
                405                 410                 415

Val Val Gln Lys Lys Leu Leu Pro Pro Phe Lys Pro Gln Val Thr Ser
            420                 425                 430

Glu Val Asp Thr Arg Tyr Phe Asp Asp Glu Phe Thr Ala Gln Ser Ile
        435                 440                 445

Thr Ile Thr Pro Pro Asp Arg Tyr Asp Ser Leu Gly Leu Leu Glu Leu
    450                 455                 460

Asp Gln Arg Thr His Phe Pro Gln Phe Ser Tyr Ser Ala Ser Ile Arg
465                 470                 475                 480

Glu

<210> SEQ ID NO 5
<211> LENGTH: 1510
<212> TYPE: DNA
<213> ORGANISM: Homo sapiens
<220> FEATURE:
<221> NAME/KEY: CDS
<222> LOCATION: (3)..(1460)

<400> SEQUENCE: 5 gg gct cag agg gga gtc atc atg agc gat gtt acc att gtg aaa gaa      47
   Ala Gln Arg Gly Val Ile Met Ser Asp Val Thr Ile Val Lys Glu
    1               5                  10                  15 ggt tgg gtt cag aag agg gga gaa tat ata aaa aac tgg agg cca aga      95
Gly Trp Val Gln Lys Arg Gly Glu Tyr Ile Lys Asn Trp Arg Pro Arg
                20                  25                  30 tac ttc ctt ttg aag aca gat ggc tca ttc ata gga tat aaa gag aaa     143
Tyr Phe Leu Leu Lys Thr Asp Gly Ser Phe Ile Gly Tyr Lys Glu Lys
            35                  40                  45 cct caa gat gtg gat tta cct tat ccc ctc aac aac ttt tca gtg gca     191
Pro Gln Asp Val Asp Leu Pro Tyr Pro Leu Asn Asn Phe Ser Val Ala
        50                  55                  60 aaa tgc cag tta atg aaa aca gaa cga cca aag cca aac aca ttt ata     239
Lys Cys Gln Leu Met Lys Thr Glu Arg Pro Lys Pro Asn Thr Phe Ile
65                  70                  75 atc aga tgt ctc cag tgg act act gtt ata gag aga aca ttt cat gta     287
Ile Arg Cys Leu Gln Trp Thr Thr Val Ile Glu Arg Thr Phe His Val
80                  85                  90                  95 gat act cca gag gaa agg gaa gaa tgg aca gaa gct atc cag gct gta     335
Asp Thr Pro Glu Glu Arg Glu Glu Trp Thr Glu Ala Ile Gln Ala Val
                100                 105                 110 gca gac aga ctg cag agg caa gaa gag gag aga atg aat tgt agt cca     383
Ala Asp Arg Leu Gln Arg Gln Glu Glu Glu Arg Met Asn Cys Ser Pro
            115                 120                 125 act tca caa att gat aat ata gga gag gaa gag atg gat gcc tct aca     431
```

```
                Thr Ser Gln Ile Asp Asn Ile Gly Glu Glu Met Asp Ala Ser Thr
                        130                 135                 140 acc cat cat aaa aga aag aca atg aat gat ttt gac tat ttg aaa cta        479
Thr His His Lys Arg Lys Thr Met Asn Asp Phe Asp Tyr Leu Lys Leu
145                 150                 155 cta ggt aaa ggc act ttt ggg aaa gtt att ttg gtt cga gag aag gca        527
Leu Gly Lys Gly Thr Phe Gly Lys Val Ile Leu Val Arg Glu Lys Ala
160                 165                 170                 175 agt gga aaa tac tat gct atg aag att ctg aag aaa gaa gtc att att        575
Ser Gly Lys Tyr Tyr Ala Met Lys Ile Leu Lys Lys Glu Val Ile Ile
                180                 185                 190 gca aag gat gaa gtg gca cac act cta act gaa agc aga gta tta aag        623
Ala Lys Asp Glu Val Ala His Thr Leu Thr Glu Ser Arg Val Leu Lys
        195                 200                 205 aac act aga cat ccc ttt tta aca tcc ttg aaa tat tcc ttc cag aca        671
Asn Thr Arg His Pro Phe Leu Thr Ser Leu Lys Tyr Ser Phe Gln Thr
                210                 215                 220 aaa gac cgt ttg tgt ttt gtg atg gaa tat gtt aat ggg ggc gag ctg        719
Lys Asp Arg Leu Cys Phe Val Met Glu Tyr Val Asn Gly Gly Glu Leu
225                 230                 235 ttt ttc cat ttg tcg aga gag cgg gtg ttc tct gag gac cgc aca cgt        767
Phe Phe His Leu Ser Arg Glu Arg Val Phe Ser Glu Asp Arg Thr Arg
240                 245                 250                 255 ttc tat ggt gca gaa att gtc tct gcc ttg gac tat cta cat tcc gga        815
Phe Tyr Gly Ala Glu Ile Val Ser Ala Leu Asp Tyr Leu His Ser Gly
                260                 265                 270 aag att gtg tac cgt gat ctc aag ttg gag aat cta atg ctg gac aaa        863
Lys Ile Val Tyr Arg Asp Leu Lys Leu Glu Asn Leu Met Leu Asp Lys
        275                 280                 285 gat ggc cac ata aaa att aca gat ttt gga ctt tgc aaa gaa ggg atc        911
Asp Gly His Ile Lys Ile Thr Asp Phe Gly Leu Cys Lys Glu Gly Ile
                290                 295                 300 aca gat gca gcc acc atg aag aca ttc tgt ggc act cca gaa tat ctg        959
Thr Asp Ala Ala Thr Met Lys Thr Phe Cys Gly Thr Pro Glu Tyr Leu
305                 310                 315 gca cca gag gtg tta gaa gat aat gac tat ggc cga gca gta gac tgg       1007
Ala Pro Glu Val Leu Glu Asp Asn Asp Tyr Gly Arg Ala Val Asp Trp
320                 325                 330                 335 tgg ggc cta ggg gtt gtc atg tat gaa atg atg tgt ggg agg tta cct       1055
Trp Gly Leu Gly Val Val Met Tyr Glu Met Met Cys Gly Arg Leu Pro
                340                 345                 350 ttc tac aac cag gac cat gag aaa ctt ttt gaa tta ata tta atg gaa       1103
Phe Tyr Asn Gln Asp His Glu Lys Leu Phe Glu Leu Ile Leu Met Glu
        355                 360                 365 gac att aaa ttt cct cga aca ctc tct tca gat gca aaa tca ttg ctt       1151
Asp Ile Lys Phe Pro Arg Thr Leu Ser Ser Asp Ala Lys Ser Leu Leu
                370                 375                 380 tca ggg ctc ttg ata aag gat cca aat aaa cgc ctt ggt gga gga cca       1199
Ser Gly Leu Leu Ile Lys Asp Pro Asn Lys Arg Leu Gly Gly Gly Pro
385                 390                 395 gat gat gca aaa gaa att atg aga cac agt ttc ttc tct gga gta aac       1247
Asp Asp Ala Lys Glu Ile Met Arg His Ser Phe Phe Ser Gly Val Asn
400                 405                 410                 415 tgg caa gat gta tat gat aaa aag ctt gta cct cct ttt aaa cct caa       1295
Trp Gln Asp Val Tyr Asp Lys Lys Leu Val Pro Pro Phe Lys Pro Gln
                420                 425                 430 gta aca tct gag aca gat act aga tat ttt gat gaa gaa ttt aca gct       1343
Val Thr Ser Glu Thr Asp Thr Arg Tyr Phe Asp Glu Glu Phe Thr Ala
        435                 440                 445
```

-continued

| | | | | | | | | | | | | | | |
|---|---|---|---|---|---|---|---|---|---|---|---|---|---|---|
| cag | act | att | aca | ata | aca | cca | cct | gaa | aaa | tat | gat | gag | gat | ggt | atg | 1391 |
| Gln | Thr | Ile | Thr | Ile | Thr | Pro | Pro | Glu | Lys | Tyr | Asp | Glu | Asp | Gly | Met |
| | 450 | | | | | 455 | | | | | 460 | | | | |

| gac | tgc | atg | gac | aat | gag | agg | cgg | ccg | cat | ttc | cct | caa | ttt | tcc | tac | 1439 |
| Asp | Cys | Met | Asp | Asn | Glu | Arg | Arg | Pro | His | Phe | Pro | Gln | Phe | Ser | Tyr |
| 465 | | | | | 470 | | | | | 475 | | | | | |

| tct | gca | agt | gga | cga | gaa | taa | gtctctttca | ttctgctact | tcactgtcat | 1490 |
| Ser | Ala | Ser | Gly | Arg | Glu |
| 480 | | | | 485 | cttcaattta ttactgaaaa                                          1510

<210> SEQ ID NO 6
<211> LENGTH: 485
<212> TYPE: PRT
<213> ORGANISM: Homo sapiens

<400> SEQUENCE: 6

Ala Gln Arg Gly Val Ile Met Ser Asp Val Thr Ile Val Lys Glu Gly
1               5                   10                  15

Trp Val Gln Lys Arg Gly Glu Tyr Ile Lys Asn Trp Arg Pro Arg Tyr
                20                  25                  30

Phe Leu Leu Lys Thr Asp Gly Ser Phe Ile Gly Tyr Lys Glu Lys Pro
            35                  40                  45

Gln Asp Val Asp Leu Pro Tyr Pro Leu Asn Asn Phe Ser Val Ala Lys
        50                  55                  60

Cys Gln Leu Met Lys Thr Glu Arg Pro Lys Pro Asn Thr Phe Ile Ile
65                  70                  75                  80

Arg Cys Leu Gln Trp Thr Thr Val Ile Glu Arg Thr Phe His Val Asp
                85                  90                  95

Thr Pro Glu Glu Arg Glu Glu Trp Thr Glu Ala Ile Gln Ala Val Ala
            100                 105                 110

Asp Arg Leu Gln Arg Gln Glu Glu Glu Arg Met Asn Cys Ser Pro Thr
        115                 120                 125

Ser Gln Ile Asp Asn Ile Gly Glu Glu Glu Met Asp Ala Ser Thr Thr
130                 135                 140

His His Lys Arg Lys Thr Met Asn Asp Phe Asp Tyr Leu Lys Leu Leu
145                 150                 155                 160

Gly Lys Gly Thr Phe Gly Lys Val Ile Leu Val Arg Glu Lys Ala Ser
                165                 170                 175

Gly Lys Tyr Tyr Ala Met Lys Ile Leu Lys Lys Glu Val Ile Ile Ala
            180                 185                 190

Lys Asp Glu Val Ala His Thr Leu Thr Glu Ser Arg Val Leu Lys Asn
        195                 200                 205

Thr Arg His Pro Phe Leu Thr Ser Leu Lys Tyr Ser Phe Gln Thr Lys
    210                 215                 220

Asp Arg Leu Cys Phe Val Met Glu Tyr Val Asn Gly Gly Glu Leu Phe
225                 230                 235                 240

Phe His Leu Ser Arg Glu Arg Val Phe Ser Glu Asp Arg Thr Arg Phe
                245                 250                 255

Tyr Gly Ala Glu Ile Val Ser Ala Leu Asp Tyr Leu His Ser Gly Lys
            260                 265                 270

Ile Val Tyr Arg Asp Leu Lys Leu Glu Asn Leu Met Leu Asp Lys Asp
        275                 280                 285

Gly His Ile Lys Ile Thr Asp Phe Gly Leu Cys Lys Glu Gly Ile Thr
    290                 295                 300

```
Asp Ala Ala Thr Met Lys Thr Phe Cys Gly Thr Pro Glu Tyr Leu Ala
305                 310                 315                 320

Pro Glu Val Leu Glu Asp Asn Asp Tyr Gly Arg Ala Val Asp Trp Trp
                325                 330                 335

Gly Leu Gly Val Val Met Tyr Glu Met Met Cys Gly Arg Leu Pro Phe
                340                 345                 350

Tyr Asn Gln Asp His Glu Lys Leu Phe Glu Leu Ile Leu Met Glu Asp
            355                 360                 365

Ile Lys Phe Pro Arg Thr Leu Ser Ser Asp Ala Lys Ser Leu Leu Ser
        370                 375                 380

Gly Leu Leu Ile Lys Asp Pro Asn Lys Arg Leu Gly Gly Pro Asp
385                 390                 395                 400

Asp Ala Lys Glu Ile Met Arg His Ser Phe Phe Ser Gly Val Asn Trp
                405                 410                 415

Gln Asp Val Tyr Asp Lys Lys Leu Val Pro Pro Phe Lys Pro Gln Val
                420                 425                 430

Thr Ser Glu Thr Asp Thr Arg Tyr Phe Asp Glu Glu Phe Thr Ala Gln
            435                 440                 445

Thr Ile Thr Ile Thr Pro Pro Glu Lys Tyr Asp Glu Asp Gly Met Asp
    450                 455                 460

Cys Met Asp Asn Glu Arg Arg Pro His Phe Pro Gln Phe Ser Tyr Ser
465                 470                 475                 480

Ala Ser Gly Arg Glu
                485
```